United States Patent
Boden et al.

(10) Patent No.: US 7,781,574 B2
(45) Date of Patent: Aug. 24, 2010

(54) CHIMERIC OSTEOGENIC FACTOR CONTAINING PROTEINS CAPABLE OF INCREASED NUCLEAR LOCALIZATION AND METHODS OF USE THEREOF

(75) Inventors: Scott D. Boden, Atlanta, GA (US); Sreedhara Sangadala, Dallas, GA (US)

(73) Assignee: Emory University

( * ) Notice: Subject to any disclaimer, the term of this patent is extended or adjusted under 35 U.S.C. 154(b) by 706 days.

(21) Appl. No.: 11/602,120

(22) Filed: Nov. 20, 2006

(65) Prior Publication Data
US 2010/0119538 A9    May 13, 2010

Related U.S. Application Data

(63) Continuation-in-part of application No. 10/806,915, filed on Mar. 23, 2004.

(60) Provisional application No. 60/456,551, filed on Mar. 24, 2003.

(51) Int. Cl.
*C07H 21/04* (2006.01)
*C12P 21/04* (2006.01)
*C12N 5/00* (2006.01)
*C12N 1/20* (2006.01)
*C12N 15/00* (2006.01)

(52) U.S. Cl. ............... 536/23.4; 536/23.5; 536/23.72; 435/69.7; 435/70.1; 435/71.2; 435/252.1; 435/320.1; 435/325; 435/455

(58) Field of Classification Search ............... None
See application file for complete search history.

(56) References Cited

U.S. PATENT DOCUMENTS

| | | | |
|---|---|---|---|
| 5,504,192 | A | 4/1996 | Gill et al. |
| 5,580,775 | A | 12/1996 | Fremeau, Jr. et al. |
| 6,300,127 | B1 * | 10/2001 | Hair et al. .......... 435/325 |
| 7,045,614 | B1 | 5/2006 | Boden et al. |

2004/0197867 A1 * 10/2004 Titus et al. ............... 435/69.1

OTHER PUBLICATIONS

Boden et al. Use of a Recombinant LMP-1 Fusion Protein to Induce Spine Fusion without the Risks of Gene Therapy. The Spine Journal, 2003, vol. 3, pp. 90S-91S (Proced. NASS 18th Annual Meeting.*
Nagahara et al. Transduction of Full Length TAT Fusion Proteins Into Mammalian Cells: TAT-p27Kip1 Induces Cell Migration. Nature Medicine, 1998, vol. 4, pp. 1449-1452.*
Boden et al., Differential effects and glucocorticoid potentiation of bone morphogenetic protein action during rat osteoblast differentiation in vitro; Endocrinology 1996, vol. 137, No. 8, pp. 3401-3407.
Boden et al., Glucocorticoid-induced differentiation of fetal rat calvarial osteoblasts is mediated by bone morphogenetic protein-6; Endocrinology 1997, vol. 138, No. 7, pp. 2820-2828.
Fujita et al., Runx2 induces osteoblast and chondrocyte differentiation and enhances their migration by coupling with PI3K-Akt signaling; The Journal of Cell Biology, Jul. 5, 2004; vol. 166, No. 1, pp. 85-95.
Ryoo et al., Stage-specific expression of Dlx-5 during osteoblast differentiation : involvement in regulation of osteocalcin gene expression; Molecular Endocrinology 1997, 11:1681-1694.
Viggeswarapu et al., Adenoviral delivery of LIM mineralization protein-1 induces new-bone formation in vitro and in vivo; The Journal of Bone & Surgery Mar. 2001; vol. 83A, No. 3, pp. 364-376.
Baumgartner, et al., "Constitutive expression of phVEGF165 after intramuscular gene transfer promotes collateral vessel development in patients with critical limb ischemia", Circulation 1998;97:1114-1123.
Nishida et al, "Adenovirus-mediated gene transfer to nucleus pulposus cells", Spine 1998; vol. 23, No. 22, pp. 2437-2443.
Kohler et al., "Continuous cultures of fused cells secreting antibody of predefined specificity", Nature 1975; 256, 495-497.

* cited by examiner

*Primary Examiner*—Deborah Crouch

(57) ABSTRACT

Compositions comprising osteogenic factors fused with membrane transduction domains of viral proteins are provided. Also provided are methods of expression and use of such compositions. Further, the methods of making such compositions are also provided. The methods involve transfecting the cells with an isolated nucleic acid comprising a nucleotide sequence encoding a LIM mineralization protein operably linked to a promoter and optionally a membrane transduction domain of a viral protein. Transfection may be accomplished ex vivo or in vivo by direct injection of virus or naked DNA, or by a nonviral vector such as a plasmid. Methods for treating disc disease associated with trauma or disc degeneration are also described.

18 Claims, 26 Drawing Sheets

FIG. 19: LMP-1

FIG. 20: Dlx5

FIG. 21: Runx2

FIG. 22: Osterix

US 7,781,574 B2

CHIMERIC OSTEOGENIC FACTOR CONTAINING PROTEINS CAPABLE OF INCREASED NUCLEAR LOCALIZATION AND METHODS OF USE THEREOF

This application claims priority from U.S. application Ser. No. 10/292,951 filed Nov. 13, 2002 which claims priority to the Provisional Application Ser. No. 60/331,321 filed Nov. 14, 2001. The entirety of that provisional application is incorporated herein by reference. This application is also a continuation-in-part of a U.S. application Ser. No. 10/806,915 filed on Mar. 23, 2004, which claims the benefit of U.S. provisional application No. 60/456,551, filed Mar. 24, 2003.

This application is related to U.S. patent application Ser. No. 09/124,238, filed Jul. 29, 1988, now U.S. Pat. No. 6,300,127, and U.S. patent application Ser. No. 09/959,578, filed Apr. 28, 2000, now U.S. Pat. No. 7,045,614. Each of these applications is incorporated by reference herein in its entirety.

BACKGROUND OF THE INVENTION

1. Field of the Invention

The field of the invention relates generally to methods for expressing LIM mineralization proteins in a host cell. More specifically, the field of the invention relates to expression and purification of intracellular mediators involved in the osteogenic factor signaling cascade during osteoblast differentiation. The field of invention also relates to methods of improving the nuclear localization of osteogenic factors in suitable cells. Finally, the field of invention relates to transfecting host cells such as intervertebral disc cells with a nucleic acid encoding a LIM mineralization protein.

2. Background of the Technology

Osteoblasts are thought to differentiate from pluripotent mesenchymal stem cells. The maturation of an osteoblast results in the secretion of an extracellular matrix which can mineralize and form bone. The regulation of this complex process is not well understood but is thought to involve a group of signaling glycoproteins known as bone morphogenetic proteins (BMPs). These proteins have been shown to be involved with embryonic dorsal-ventral patterning, limb bud development, and fracture repair in adult animals. B. L. Hogan, Genes & Develop., 10, 1580 (1996).

BMPs are members of the Transforming growth factor-beta superfamily (TGF-β) proteins that play a role in maturation of osteoblasts and the bone regulation pathways. TGF-β secreted proteins has a spectrum of activities in a variety of cell types at different stages of differentiation. However, differences in physiological activity between these closely related molecules have not been clarified. D. M. Kingsley, Trends Genet., 10, 16 (1994).

In addition to extracellular signals, such as the BMPs, intracellular signals or regulatory molecules also play a role in the cascade of events leading to formation of new bone. Examples of such regulatory osteogenic molecules include LIM mineralization proteins (LMPs), Runt-Related Transcription Factor (Runx-2), *Drosophila* distalles (Dlx), and Osterix (Osx).

It is common knowledge that the differentiation process of osteoblasts requires a complex coordination of all such osteogenic factors including BMPs, other members of the transforming TGF-β superfamily, LMPs, Dlx, Runx-2, Osx are key osteogenic factors that play critical roles in the BMP pathway.

To better discern the unique physiological role of different factors studies are required to better understand the nature of their interaction. We have performed many studies on the nature of BMP signaling protein pathways. We have recently compared the potency of BMP-6 with that of BMP-2 and BMP-4, for inducing rat calvarial osteoblast differentiation. Boden, et al., Endocrinology, 137, 3401 (1996). We studied this process in first passage (secondary) cultures of fetal rat calvaria that require BMP or glucocorticoid for initiation of differentiation. In this model of membranous bone formation, glucocorticoid (GC) or a BMP will initiate differentiation to mineralized bone nodules capable of secreting osteocalcin, the osteoblast-specific protein. This secondary culture system is distinct from primary rat osteoblast cultures which undergo spontaneous differentiation. In this secondary system, glucocorticoid resulted in a ten-fold induction of BMP-6 mRNA and protein expression which was responsible for the enhancement of osteoblast differentiation. Boden, et al., Endocrinology, 138, 2920 (1997).

Other investigations have also been performed to assess the relationship between other osteogenic factors and BMPs. Bourque et al elaborated on Runx-2 critical role in the differentiation of cells toward an osteoblastic pathway. Bourque et al, Expression of four growth factors during fracture repair. Int. J. Dev. Biol, 1993:37:573-9. Runx2 is a transcription factor that belongs to the Runx family. Komori, T., et al. 1997. Targeted disruption of Cbfa1 results in a complete lack of bone formation owing to maturational arrest of osteoblasts. *Cell.* 89:755-764; Fujita et al (2004) "Runx2 induces osteoblast and chondrocyte differentiation and enhances their migration by coupling with PI3K-Akt signaling." J. Cell Biol. 166:85-95.

Runx2-deficient (Runx2$^{-/-}$) mice completely lack bone formation owing to the absence of osteoblasts. Runx2 determines the osteoblast lineage from multipotent mesenchymal cells, induces osteoblastic differentiation at the early stage, and inhibits it at the late stage. Further, Runx2 has been shown to induce alkaline phosphatase (ALP) activity, expression of bone matrix protein genes, and mineralization in immature mesenchymal cells and osteoblastic cells in vitro. Chondrocyte differentiation is also disturbed in Runx2$^{-/-}$ mice.

Overexpression of Runx2 or the dominant-negative (dn) form of Runx2 (dn-Runx2) in chondrocytes accelerates or decelerates chondrocyte maturation, respectively, indicating that Runx2 is a positive regulatory factor in chondrocyte maturation. Further, introduction of dn-Runx2 inhibited cell condensation in insulin-induced chondrogenesis of ATDC5 cells. Thus, Runx2 plays crucial roles in osteoblast and chondrocyte differentiation.

Dlx proteins have been implicated to play major role in osteogenesis as well. Ryoo, H. M., et al. (1997) "Stage-specific expression of Dlx-5 during osteoblast differentiation: involvement in regulation of osteocalcin gene expression." Mol. Endocrinol. 11, 1681-1694. It has been shown that the mammalian homologs of Dlx 5 and 6 are homeobox genes essential for craniofacial and skeletal development. Dlx5 is a target gene for BMPs that regulate osteogenesis and dorsoventral patterning and targeted gene inactivation of Dlx 5 and 6 results in severe skeletal abnormalities leading to prenatal lethality. Sandhu et al. "Evaluation of rhBMP-2 with an OPLA carrier in a canine posterolateral (transverse process) spinal fusion model." *Spine* 1995; 20:2669-82.

Osx is a novel zinc finger containing transcription factor expressed by osteoblasts and required for endochondral and intra membranous bone formation. Nakashima, K., et al, (2002) "The novel zinc finger-containing transcription factor osterix is required for osteoblast differentiation and bone formation." Cell 108:17-29. Osterix-null mice have normal cartilage development but fail to develop mineralized skeleton. Yasko et al. the Healing of segmental bone defects, induced by recombinant human bone morphogenetic protein (rhBMP-2). A radiographic, histological, and biomechanical study in rats. *J Bone Joint Surg Am,* 1992; 74:659-70.

Another broad class of intracellular regulatory molecules are the LIM proteins, which are so named because they possess a characteristic structural motif known as the LIM domain. Viggeswarapu M, Boden S D et al. (2001) "Adenoviral delivery of LIM mineralization protein-1 induces new-bone formation in vitro and in vivo." J Bone & Joint Surg Am. 83:364-376. The LIM domain is a cysteine-rich structural motif composed of two special zinc fingers that are joined by a 2-amino acid spacer. Some proteins have only LIM domains, while others contain a variety of additional functional domains. LIM proteins form a diverse group, which includes transcription factors and cytoskeletal proteins. The primary role of LIM domains appears to be in mediating protein-protein interactions, through the formation of dimers with identical or different LIM domains, or by binding distinct proteins.

In LIM homeodomain proteins, that is, proteins having both LIM domains and a homeodomain sequence, the LIM domains function as negative regulatory elements. LIM homeodomain proteins are involved in the control of cell lineage determination and the regulation of differentiation, although LIM-only proteins may have similar roles. LIM-only proteins are also implicated in the control of cell proliferation since several genes encoding such proteins are associated with oncogenic chromosome translocations.

Humans and other mammalian species are prone to diseases or injuries that require the processes of bone repair and/or regeneration. For example, treatment of fractures would be improved by new treatment regimens that could stimulate the natural bone repair mechanisms, thereby reducing the time required for the fractured bone to heal. In another example, individuals afflicted with systemic bone disorders, such as osteoporosis, would benefit from treatment regimens that would result in systemic formation of new bone. Such treatment regimens would reduce the incidence of fractures arising from the loss of bone mass that is a characteristic of this disease.

For at least these reasons, extracellular factors, such as the BMPs, have been investigated for the purpose of using them to stimulate formation of new bone in vivo. Despite the early successes achieved with BMPs and other extracellular signaling molecules, their use entails a number of disadvantages.

For example, relatively large doses of purified BMPs are required to enhance the production of new bone, thereby increasing the expense of such treatment methods. Furthermore, extracellular proteins are susceptible to degradation following their introduction into a host animal. In addition, because they are typically immunogenic, the possibility of stimulating an immune response to the administered proteins is ever present.

Due to such concerns, it would be desirable to have available treatment regimens that use an intracellular signaling molecule that can induce new bone formation. Advances in the field of gene therapy now make it possible to introduce into osteogenic precursor cells, that is, cells involved in bone formation, or peripheral blood leukocytes, nucleotide fragments encoding intracellular signals that form part of the bone formation process. Gene therapy for bone formation offers a number of potential advantages: (1) lower production costs; (2) greater efficacy, compared to extracellular treatment regimens, due to the ability to achieve prolonged expression of the intracellular signal; (3) it would by-pass the possibility that treatment with extracellular signals might be hampered due to the presence of limiting numbers of receptors for those signals; (4) it permits the delivery of transfected potential osteoprogenitor cells directly to the site where localized bone formation is required; and (5) it would permit systemic bone formation, thereby providing a treatment regimen for osteoporosis and other metabolic bone diseases.

In addition to diseases of the bone, humans and other mammalian species are also subject to intervertebral disc degeneration, which is associated with, among other things, low back pain, disc herniation, and spinal stenosis. Disc degeneration is associated with a progressive loss of proteoglycan matrix. This may cause the disc to be more susceptible to bio-mechanical injury and degeneration. Accordingly, it would be desirable to have a method of stimulating proteoglycan and/or collagen synthesis by the appropriate cells, such as, for example, cells of the nucleus pulpous, cells of the annulus fibrosis, and cells of the intervertebral disc.

SUMMARY OF THE INVENTION

According to a first aspect of the invention, a method of expressing a LIM mineralization protein in a host mammalian cell is provided. According to this aspect of the invention, the method comprises transfecting the cell with an isolated nucleic acid comprising a nucleotide sequence encoding the LIM mineralization protein operably linked to a promoter. The cell can be a cell capable of producing proteoglycan and/or collagen such that the expression of the LIM mineralization protein stimulates proteoglycan and/or collagen synthesis in the cell. The isolated nucleic acid according to this aspect of the invention can be a nucleic acid which can hybridize under standard conditions to a nucleic acid molecule complementary to the full length of SEQ. ID NO: 25; and/or a nucleic acid molecule which can hybridize under highly stringent conditions to a nucleic acid molecule complementary to the full length of SEQ. ID NO: 26. The cell can be a stem cell, an intervertebral disc cell, a cell of the annulus fibrosus, or a cell of the nucleus pulposus.

According to a second aspect of the invention, a mammalian cell comprising an isolated nucleic acid sequence encoding a LIM mineralization protein is provided. According to this aspect of the invention, purified chimeric nucleotides are also prepared that are expected to exhibit a greater degree of expression relative to those of their parental counterparts. According to this aspect of the invention, the cell can be a stem cell, a cell of the nucleus pulposus, a cell of the annulus fibrosus, an intervertebral disc cell or other types of cell capable of such expression.

According to a third goal of this invention purified recombinant protein constructs were developed. According to this aspect of the invention, chimeric polypeptide sequences are developed for delivery of the bone specific mammalian transcription factors. According to this aspect of the invention, the developed chimeric polypeptide sequences are capable of nuclear localization in a form accessible to interaction with other nuclear proteins.

According to a fourth aspect of the invention, a method of treating intervertebral disc injury or disease is provided. According to this aspect of the invention, the method comprises transfecting an isolated nucleic acid into a mammalian cell capable of producing proteoglycan and/or collagen. The isolated nucleic acid comprises a nucleotide sequence encoding a LIM mineralization protein operably linked to a promoter. The LIM mineralization protein stimulates proteoglycan and/or collagen synthesis in the cell.

According to a fifth aspect of the invention, an intervertebral disc implant is provided. According to this aspect of the invention, the implant comprises a carrier material and a plurality of mammalian cells comprising an isolated nucleic acid sequence encoding a LIM mineralization protein optionally with a nuclear localization signal. Also according to this aspect of the invention, the carrier material comprises a porous matrix of biocompatible material and the mammalian cells are incorporated into the carrier material.

According to a sixth aspect of the invention, a system and a method is developed to meet the demands of proteomics for transient transfection-based mammalian expression. According to this aspect of the invention, a method is developed for identifying LMP-1 protein internal sequencing and assessing post-translational glycosylation in a mammalian expression system wherein the method employs carbohydrate analysis of LMP-1 hydrolysates.

Furthermore, this aspect of the invention introduces a novel purification and detection methods wherein the skilled artisan is now able to purify the recombinant proteins to a level of homogeneity by means of (1) size fractionation of proteins prior to metal affinity chromatography to improve efficiency of affinity resin and (2) identification of tryptic fragments of purified protein.

According to a seventh aspect of the invention, a composition is prepared that comprises a LIM mineralization protein that is substantially free of any carbohydrate moiety.

BRIEF DESCRIPTION OF THE DRAWINGS

The present invention may be better understood with reference to the accompanying drawings in which:

In FIG. 4A, exogenous LMP-1 expression was induced with different doses (MOI) of the Ad-hLMP-1 virus and quantitated with real-time PCR. The data is normalized to HLMP-1 mRNA levels from Ad-LMP-1 MOI 5 for comparison purposes. No HLMP-1 was detected in negative control groups, the no-treatment ("NT") or Ad-LacZ treatment ("LacZ"). HLMP-1 mRNA levels in a dose dependent fashion to reach a plateau of approximately 8 fold with a MOI of 25 and 50.

In FIG. 4B, each result is expressed as mean with SD for three samples.

In FIG. 5, "**" indicates data points for which the P value is <0.01 versus the untreated control.

In FIGS. 6A and 6B, each result is expressed as mean with SD for six samples. In FIGS. 6A and 6B, "**" indicates data points for which the P value is P<0.01.

In FIG. 8, "**" indicates data points for which the P value is <0.01 for infection with AdLMP-1 versus an untreated control.

As seen in FIG. 10, infection of rat annulus cells with Ad-LMP-1 at a MOI of 25 led to a three fold increase in sGAG produced between day 3 and day 6. This increase was blocked by the addition of noggin (a BMP antagonist) at concentration of 3200 ng/ml and 800 ng/m. As shown in FIG. 10, however, noggin did not significantly alter sGAG production in uninfected cells. As can also be seen in FIG. 10, stimulation with rhBMP-2 at 100 ng/ml led to a 3 fold increase in sGAG production between day 3 and day 6 after addition of BMP-2. Noggin at 800 ng/ml also blocked this increase.

As shown in FIG. 11, LMP-1 with the CMV promoter when delivered by the AAV vector is also effective in stimulating glycosaminoglycan synthesis by rat disc cells in monolayer.

ABBREVIATIONS AND DEFINITIONS

Figure 1:
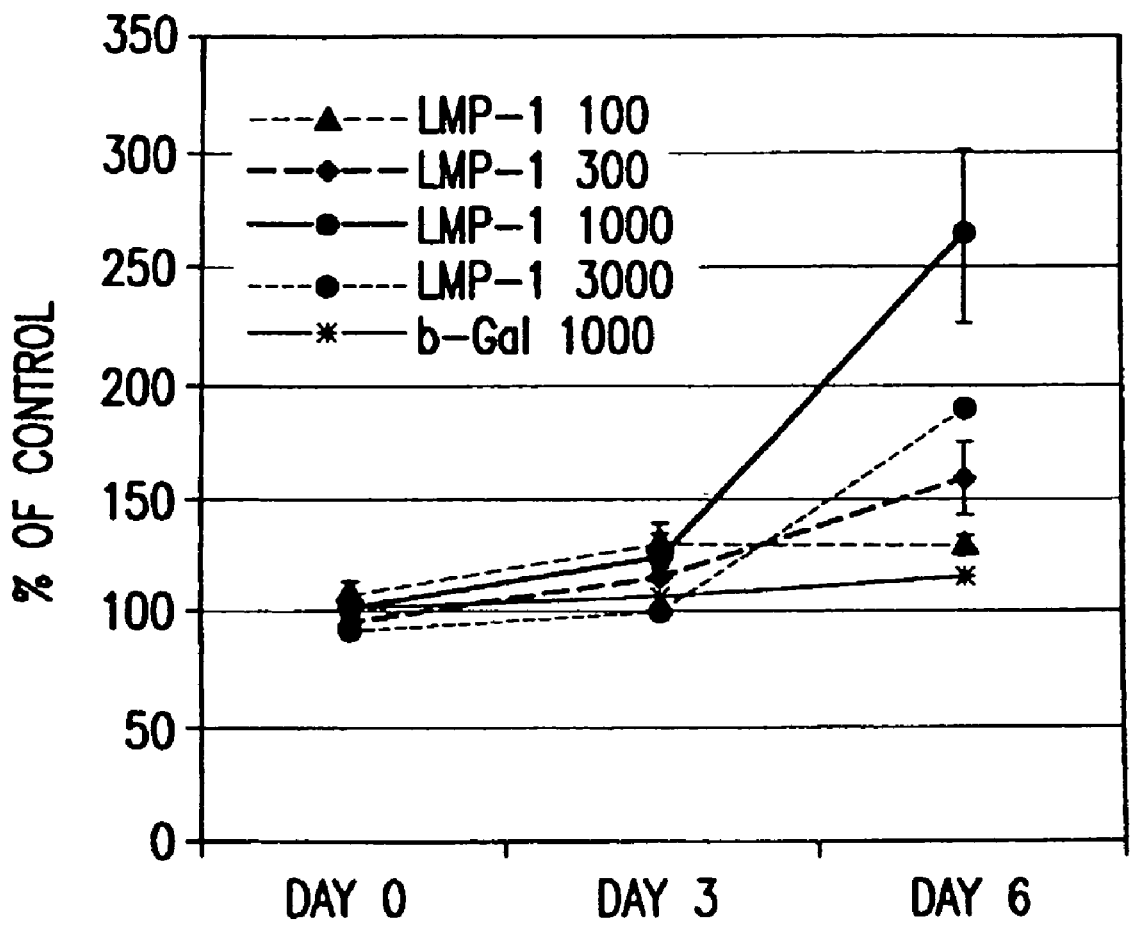
FIG. 1 is a graph showing the production of sulfated glycosaminoglycan (sGAG) after expression of HLMP-1 by rat intervertebral disc cells transfected with different MOIs (SEQ ID NOS 84-86)

BMP, Bone Morphogenetic Protein;
HLMP-1, Human LMP-1, also designated as Human LIM-Protein or HLMP;
HLMP-1s Human LMP-1 Short (truncated) protein,
HLMPU Human LIM Protein Unique Region;
LMP LIM mineralization protein,
LMP-1, LIM mineralization protein-1;
MEM Minimal essential medium;
Trm, Triamcinolone;

β-GlyP; beta-GlyP, Beta-glycerolphosphate;
RACE, Rapid Amplification of cDNA Ends;
RLMP, Rat LIM mineralization protein, also designated as RLMP-1; RLMPU,
Rat LIM Protein Unique Region;
RNAsin, RNase inhibitor;
ROB, Rat Osteoblast;
10-4, Clone containing cDNA sequence for RLMP (SEQ ID NO: 2);
UTR, Untranslated Region;
HLMP-2, Human LMP Splice Variant 2;
HLMP-3, Human LMP Splice Variant 3;
MOI, multiplicity of infection;
sGAG, sulfated glycosaminoglycan;
AdHLMP-1, Recombinant Type 5 Adenovirus comprising nucleotide sequence encoding HLMP-1;
SDS-PAGE, Sodium dodecyl polyacrylamide gel electrophoresis;
FPLC, Fast performance liquid chromatography;
HPLC, High performance liquid chromatography;
Ni-NTA, Nickel-nitrilotriacetic acid;
PMSF, phenylmethylsulfonyl fluoride;
BSA, bovine serum albumin.
MALDI TOF, Matrix Assisted Laser. Desorption Ionization Time of Flight;
MS, Mass spectrometry;
PSD, Post source decay;
IPTG, Isopropyl-βD-thiogalactopyranoside; LB, Luria Broth medium As used herein, the term "isolated/and or purified" refers to in vitro preparation, isolation, and/or purification of a nucleic acid or protein from its natural cellular environment or from association with other components of the cell, so that it is not associated with in vivo substances.

As used herein, the term "recombinant DNA" means any DNA molecule consisting of segments of DNA from different genomes (the entire DNA or cell or virus) which have been joined end-to-end outside of living cells and have the capacity to transfect suitable host cells and be maintained therein. Moreover, the term "recombinant polypeptide, protein or amino acid sequence" means any such molecule that was expressed from a recombinant DNA consisting of segments of DNA that have been joined end-to-end outside of living cells and have the capacity to be transfected into host cells and be maintained therein.

As used herein, the term "chimeric" means that a vector comprises DNA from at least two different species or comprises DNA from the same species which is linked or associated in a manner which does not occur in the "native," or "wild type" of the species.

As used herein, the term "operably linked" means that the nucleic acids are placed in a functional relationship with another nucleic acid sequence.

Transfection can occur either ex vivo or in vivo by direct injection of virus or naked DNA, such as, for example, a plasmid. In certain embodiments, the virus is a recombinant adenovirus, preferably AdHLMP-1

DETAILED DESCRIPTION OF THE PREFERRED EMBODIMENTS

The present invention relates to the transfection of non-osseous cells with nucleic acids encoding LIM mineralization proteins. The present inventors have discovered that transfection of non-osseous and osseous cells such as intervertebral disc cells with nucleic acids encoding LIM mineralization proteins can result in the increased synthesis of proteoglycan, collagen and other intervertebral disc components and tissue. The present invention also provides a method for treating intervertebral disc disease associated with the loss of proteoglycan, collagen, or other intervertebral disc components.

It is to be understood that both the foregoing general description and the following detailed description are exemplary and explanatory and are intended to provide further explanation of the invention as claimed.

A LIM gene (10-4/RLMP) has been isolated from stimulated rat calvarial osteoblast cultures (SEQ. ID NO: 1, SEQ. ID NO: 2). See U.S. Pat. No. 6,300,127. This gene has been cloned, sequenced and assayed for its ability to enhance the efficacy of bone mineralization in vitro. The protein RLMP has been found to affect the mineralization of bone matrix as well as the differentiation of cells into the osteoblast lineage. Unlike other known cytokines (e.g., BMPs), RLMP is not a secreted protein, but is instead an intracellular signaling molecule. This feature has the advantage of providing intracellular signaling amplification as well as easier assessment of transfected cells. It is also suitable for more efficient and specific in vivo applications. Suitable clinical applications include enhancement of bone repair in fractures, bone defects, bone grafting, and normal homeostasis in patients presenting with osteoporosis.

The amino acid sequence of a corresponding human protein, named human LMP-1 ("HLMP-1"), has also been cloned, sequenced and deduced. (SEQ. ID NO: 10). See U.S. Pat. No. 6,300,127. The human protein has been found to demonstrate enhanced efficacy of bone mineralization in vitro and in vivo. The sequence of LMP-1 contains a highly conserved N-terminal PDZ domain and three C-terminal LIM domains. The sequence analysis of LMP-1 predicts two putative N-glycosylation sites. At least one aspect of this invention is to verify whether LMP-1 was expressed in detectable amounts and purify the recombinant LMP-1 for carbohydrate analysis to determine if the LMP-1 expressed in mammalian system undergoes post translational glycosylation.

Additionally, a truncated (short) version of HLMP-1, termed HLMP-1s, has been characterized. See U.S. Pat. No. 6,300,127. This short version resulted from a point mutation in one source of a cDNA clone, providing a stop codon which truncates the protein. HLMP-1s has been found to be fully functional when expressed in cell culture and in vivo.

Using PCR analysis of human heart cDNA library, two alternative splice variants (referred to as HLMP-2 and HLMP-3) have been identified that differ from HLMP-1 in a region between base pairs 325 and 444 in the nucleotide sequence encoding HLMP-1. See U.S. patent application Ser. No. 09/959,578, filed Apr. 28, 2000, now U.S. Pat. No. 7,045,614. The HLMP-2 sequence has a 119 base pair deletion and an insertion of 17 base pairs in this region. Compared to HLMP-1, the nucleotide sequence encoding HLMP-3 has no deletions, but it does have the same 17 base pairs as HLMP-2, which are inserted at position 444 in the HLMP-1 sequence.

LMP is a pluripotent molecule, which regulates or influences a number of biological processes. The different splice variants of LMP are expected to have different biological functions in mammals. They may play a role in the growth, differentiation, and/or regeneration of various tissues. For example, some form of LMP is expressed not only in bone, but also in muscle, tendons, ligaments, spinal cord, peripheral nerves, and cartilage.

According to one aspect, the present invention relates to a method of stimulating proteoglycan and/or collagen synthesis in a mammalian cell by providing an isolated nucleic acid comprising a nucleotide sequence encoding LIM mineralization protein operably linked to a promoter; transfecting said isolated nucleic acid sequence into a mammalian cell capable of producing proteoglycan; and expressing said nucleotide sequence encoding LIM mineralization protein, whereby proteoglycan synthesis is stimulated. The mammalian cell may be a non-osseous cell, such as an intervertebral disc cell, a cell of the annulus fibrosus, or a cell of the nucleus pulposus. Transfection may occur either ex vivo or in vivo by direct injection of virus or naked DNA, such as, for example, a plasmid. In certain embodiments, the virus is a recombinant adenovirus, preferably AdHLMP-1.

Another embodiment of the invention comprises a non-osseous mammalian cell comprising an isolated nucleic acid sequence encoding a LIM mineralization protein. The non-osseous mammalian cell may be a stem cell (e.g., a pluripotent stem cell or a mesenchymal stem cell) or an intervertebral disc cell, preferably a cell of the nucleus pulposus or a cell of the annulus fibrosus.

In a different aspect, the invention is directed to a method of expressing an isolated nucleotide sequence encoding LIM mineralization protein in a non-osseous mammalian cell, comprising: providing an isolated nucleic acid comprising a nucleotide sequence encoding LIM mineralization protein operably linked to a promoter; transfecting said isolated nucleic acid sequence into a non-osseous mammalian cell; and expressing said nucleotide sequence encoding LIM mineralization protein. The non-osseous mammalian cell may be a stem cell or an intervertebral disc cell (e.g., a cell of the nucleus pulposus or annulus fibrosus). Transfection may occur either ex vivo or in vivo by direct injection of virus or naked DNA, such as, for example, a plasmid. The virus can be a recombinant adenovirus, preferably AdHLMP-1.

In yet another embodiment, purified chimeric nucleotides are prepared that will exhibit a greater degree of expression relative to those of their parental counterparts. According to this aspect of the invention, bacterially expressed TAT-fusion-cDNAs of osteogenic factors were prepared that have the potential to either replace BMP-2 in inducing bone formation or to serve as enhancers of BMP-2 efficacy.

According to another aspect of this invention, purified recombinant protein constructs were developed. According to this aspect of the invention, chimeric polypeptide sequences are developed for delivery of the bone specific mammalian transcription factors. According to this aspect of the invention, Osteogenic factors containing TAT domain were obtained and purified. The developed chimeric polypeptide sequences are capable of nuclear localization in a form accessible to interaction with other nuclear proteins.

In yet another aspect of this invention, the application is directed to a method of treating intervertebral disc disease by reversing, retarding or slowing disc degeneration, comprising providing an isolated nucleic acid comprising a nucleotide sequence encoding LIM mineralization protein operably linked to a promoter; transfecting said isolated nucleic acid sequence into a mammalian cell capable of producing proteoglycan; and stimulating proteoglycan synthesis in said cell by expressing said nucleotide sequence encoding LIM mineralization protein, whereby disc degeneration is reversed, halted or slowed. The disc disease may involve lower back pain, disc herniation, or spinal stenosis. The mammalian cell may be a non-osseous cell, such as a stem cell or an intervertebral disc cell (e.g., a cell of the annulus fibrosus, or a cell of the nucleus pulposus).

Transfection may occur either ex vivo or in vivo by direct injection of virus or naked DNA, such as, for example, a plasmid. In certain embodiments, the virus is a recombinant adenovirus, preferably AdHLMP-1.

The present invention relates to novel mammalian LIM proteins, herein designated LIM mineralization proteins, or LMPs. The invention relates more particularly to human LMP, known as HLMP or HLMP-1, or alternative splice variants of human LMP, which are known as HLMP-2 or HLMP-3. The Applicants have discovered that these proteins enhance bone mineralization in mammalian cells grown in vitro. When produced in mammals, LMP also induces bone formation in vivo.

It is well established that uptake of charged molecules or high molecular weight peptides and proteins into live cells is hampered by the lipophilic nature of the plasma membrane. Protein engineering is currently used for the creation of new fusion proteins with desirable traits, which include penetration of exogenously added recombinant proteins into cytosolic and nuclear compartments of cells. In at least one aspect of this invention, we have prepared hybrid proteins that are expressed and further accumulated in both cytoplasmic and nuclear compartments. Preferably, the hybrid protein is a TAT-tagged osteogenic factor, more preferably a TAT-tagged-LMP-1. This is the first time that a recombinant TAT-LMP-1 has been shown to interact with nuclear proteins. Accordingly, such TAT-fusion proteins can be used as molecular bait to identify the intracellular interacting proteins.

With respect to clinical use, ex vivo transfection of bone marrow cells, osteogenic precursor cells, peripheral blood cells, and stem cells (e.g., pluripotent stem cells or mesenchymal stem cells) with nucleic acid that encodes a LIM mineralization protein (e.g., LMP or HLMP), followed by reimplantation of the transfected cells in the donor, is suitable for treating a variety of bone-related disorders or injuries. For example, one can use this method to: augment long bone fracture repair; generate bone in segmental defects; provide a bone graft substitute for fractures; facilitate tumor reconstruction or spine fusion; and provide a local treatment (by injection) for weak or osteoporotic bone, such as in osteoporosis of the hip, vertebrae, or wrist. Transfection with LMP or HLMP-encoding nucleic acid is also useful in: the percutaneous injection of transfected marrow cells to accelerate the repair of fractured long bones; treatment of delayed union or non-unions of long bone fractures or pseudoarthrosis of spine fusions; and for inducing new bone formation in avascular necrosis of the hip or knee.

In addition to ex vivo methods of gene therapy, transfection of a recombinant DNA vector comprising a nucleic acid sequence that encodes LMP or HLMP can be accomplished in vivo. When a DNA fragment that encodes LMP or HLMP is inserted into an appropriate viral vector, for example, an adenovirus vector, the viral construct can be injected directly into a body site were endochondral bone formation is desired. By using a direct, percutaneous injection to introduce the LMP or HLMP sequence stimulation of bone formation can be accomplished without the need for surgical intervention either to obtain bone marrow cells (to transfect ex vivo) or to reimplant them into the patient at the site where new bone is required. Alden, et al., Neurosurgical Focus (1998), have demonstrated the utility of a direct injection method of gene therapy using a cDNA that encodes BMP-2, which was cloned into an adenovirus vector.

It is also possible to carry out in vivo gene therapy by directly injecting into an appropriate body site, a naked, that is, unencapsulated, recombinant plasmid comprising a nucleic acid sequence that encodes HLMP. In this embodiment of the invention, transfection occurs when the naked plasmid DNA is taken up, or internalized, by the appropriate target cells, which have been described. As in the case of in vivo gene therapy using a viral construct, direct injection of naked plasmid DNA offers the advantage that little or no surgical intervention is required. Direct gene therapy, using naked plasmid DNA that encodes the endothelial cell mitogen VEGF (vascular endothelial growth factor), has been successfully demonstrated in human patients. Baumgartner, et al., Circulation, 97, 12, 1114-1123 (1998).

For intervertebral disc applications, ex vivo transfection may be accomplished by harvesting cells from an intervertebral disc, transfecting the cells with nucleic acid encoding LMP in vitro, followed by introduction of the cells into an intervertebral disc. The cells may be harvested from or introduced back into the intervertebral disc using any means known to those of skill in the art, such as, for example, any surgical techniques appropriate for use on the spine. In one embodiment, the cells are introduced into the intervertebral disc by injection.

Also according to the invention, stem cells (e.g., pluripotential stem cells or mesenchymal stem cells) can be transfected with nucleic acid encoding a LIM Mineralization Protein ex vivo and introduced into the intervertebral disc (e.g., by injection).

The cells transfected ex vivo can also be combined with a carrier to form an intervertebral disc implant. The carrier comprising the transfected cells can then be implanted into the intervertebral disc of a subject. Suitable carrier materials are disclosed in Helm, et al., "Bone Graft Substitutes for the Promotion of Spinal Arthrodesis", Neurosurg Focus, Vol. 10 (4): April 2001. The carrier preferably comprises a biocompatible porous matrix such as a demineralized bone matrix (DBM), a biocompatible synthetic polymer matrix or a protein matrix. Suitable proteins include extracellular matrix proteins such as collagen. The cells transfected with the LMP ex vivo can be incorporated into the carrier (i.e., into the pores of the porous matrix) prior to implantation.

Similarly, for intervertebral disc applications where the cells are transfected in vivo, the DNA may be introduced into the intervertebral disc using any suitable method known to those of skill in the art. In one embodiment, the nucleic acid is directly injected into the intervertebral space.

By using an adenovirus vector to deliver LMP into osteogenic cells, transient expression of LMP is achieved. This occurs because adenovirus does not incorporate into the genome of target cells that are transfected. Transient expression of LMP, that is, expression that occurs during the lifetime of the transfected target cells, is sufficient to achieve the objects of the invention. Stable expression of LMP, however, can occur when a vector that incorporates into the genome of the target cell is used as a delivery vehicle. Nishida et al, the teaching of which is incorporated herewith in its entirety, investigated the efficacy of adenovirus-mediate gene transfer to Nucleus Pulposus cells. Neshida et al., Spine, Vol. 23(22): 2437-2442 (15 Nov. 1998).

Nishida et al successfully demonstrate adenovirus-mediated gene transfer to the intervertebral disc with persistent expression of the marker gene for at least 12 weeks in vivo in high titters. In addition, the transfected intervertebral discs in Nishida's experiment did not exhibit typical signs of local immune activity. This result indicates that the avascular environment of intervertebral disc limits the access of immunocompetent cells, thereby preventing immune reactivity and prolonging gene expressions. Due to such results the inventors believe that Retrovirus-based vectors, are also suitable for this purpose.

Stable expression of LMP is particularly useful for treating various systemic bone-related disorders, such as osteoporosis and osteogenesis imperfecta. For this embodiment of the invention, in addition to using a vector that integrates into the genome of the target cell to deliver an LMP-encoding nucleotide sequence into target cells, LMP expression can be placed under the control of a regulatable promoter. For example, a promoter that is turned on by exposure to an exogenous inducing agent, such as tetracycline, is suitable.

It has been shown that uptake of charged molecules or high molecular weight peptides and proteins into live cells is hampered by the lipophilic nature of the plasma membrane. Protein engineering is currently used for the creation of new fusion proteins with desirable traits, which include penetration of exogenously added recombinant proteins into cytosolic and nuclear compartments of cells.

Using this approach, one can stimulate formation of new bone on a systemic basis by administering an effective amount of the exogenous inducing agent. Once a sufficient quantity of bone mass is achieved, administration of the exogenous inducing agent can be discontinued. This process may be repeated as needed to replace bone mass lost, for example, as a consequence of osteoporosis. Antibodies specific for HLMP are particularly suitable for use in methods for assaying the osteoinductive, that is, bone-forming, potential of patient cells. In this way one can identify patients at risk for slow or poor healing of bone repair. Also, HLMP-specific antibodies are suitable for use in marker assays to identify risk factors in bone degenerative diseases, such as, for example, osteoporosis.

Following well known and conventional methods, the genes of the present invention are prepared by ligation of nucleic acid segments that encode LMP to other nucleic acid sequences, such as cloning and/or expression vectors. Methods needed to construct and analyze these recombinant vectors, for example, restriction endonuclease digests, cloning protocols, mutagenesis, organic synthesis of oligonucleotides and DNA sequencing, have been described. For DNA sequencing DNA, the dioxyterminator method is the preferred.

Many treatises on recombinant DNA methods have been published, including Sambrook, et al., Molecular Cloning: A Laboratory Manual, 2nd edition, Cold Spring Harbor Press, (1988), Davis. et al., Basic Methods in Molecular Biology, Elsevier (1986), and Ausubel, et al., Current Protocols in Molecular Biology, Wiley Interscience (1988). These reference manuals are specifically incorporated by reference herein.

Primer-directed amplification of DNA or cDNA is a common step in the expression of the genes of this invention. It is typically performed by the polymerase chain reaction (PCR). PCR is described in U.S. Pat. No. 4,800,159 to Mullis, et al. and other published sources. The basic principle of PCR is the exponential replication of a DNA sequence by successive cycles of primer extension. The extension products of one primer, when hybridized to another primer, becomes a template for the synthesis of another nucleic acid molecule. The primer-template complexes act as substrate for DNA polymerase, which in performing its replication function, extends the primers. The conventional enzyme for PCR applications is the thermostable DNA polymerase isolated from *Thermus aquaticus*, or Taq DNA polymerase.

Numerous variations of the basic PCR method exist, and a particular procedure of choice in any given step needed to construct the recombinant vectors of this invention is readily performed by a skilled artisan. For example, to measure cellular expression of 10-4/RLMP, RNA is extracted and reverse transcribed under standard and well known procedures. The resulting cDNA is then analyzed for the appropriate mRNA sequence by PCR.

The gene encoding the LIM mineralization protein is expressed in an expression vector in a recombinant expression system. Of course, the constructed sequence need not be the same as the original, or its complimentary sequence, but instead may be any sequence determined by the degeneracy of the DNA code that nonetheless expresses an LMP having bone forming activity. Conservative amino acid substitutions, or other modifications, such as the occurrence of an amino-terminal methionine residue, may also be employed.

A ribosome binding site active in the host expression system of choice is ligated to the 5' end of the chimeric LMP coding sequence, forming a synthetic gene. The synthetic gene can be inserted into any one of a large variety of vectors for expression by ligating to an appropriately linearized plasmid. A regulatable promoter, for example, the E. coli lac promoter, is also suitable for the expression of the chimeric coding sequences. Other suitable regulatable promoters include trp, tac, recA, T7 and lambda promoters.

DNA encoding LMP is transfected into recipient cells by one of several standard published procedures, for example, calcium phosphate precipitation, DEAE-Dextran, electroporation or protoplast fusion, to form stable transformants. Calcium phosphate precipitation is preferred, particularly when performed as follows.

DNAs are co precipitated with calcium phosphate according to the method of Graham and Van Der, Virology, 52, 456 (1973), before transfer into cells. An aliquot of 40-50 μg of DNA, with salmon sperm or calf thymus DNA as a carrier, is used for $0.5 \times 10^6$ cells plated on a 100 mm dish. The DNA is mixed with 0.5 ml of 2× Hepes solution (280 mM NaCl, 50 mM Hepes and 1.5 mM $Na_2HPO_4$, pH 7.0), to which an equal volume of $2 \times CaCl_2$ (250 mM $CaCl_2$ and 10 mM Hepes, pH 7.0) is added. A white granular precipitate, appearing after 30-40 minutes, is evenly distributed dropwise on the cells, which are allowed to incubate for 4-16 hours at 37° C. The medium is removed and the cells shocked with 15% glycerol in PBS for 3 minutes. After removing the glycerol, the cells are fed with Dulbecco's Minimal Essential Medium (DMEM) containing 10% fetal bovine serum.

DNA can also be transfected using: the DEAE-Dextran methods of Kimura, et al., Virology, 49:394 (1972) and Sompayrac et al., Proc. Natl. Acad. Sci. USA, 78, 7575 (1981); the electroporation method of Potter, Proc. Natl. Acad. Sci. USA, 81, 7161 (1984); and the protoplast fusion method of Sandri-Goddin et al., Molec. Cell. Biol., 1, 743 (1981).

Phosphoramidite chemistry in solid phase is the preferred method for the organic synthesis of oligodeoxynucleotides and polydeoxynucleotides. In addition, many other organic synthesis methods are available. Those methods are readily adapted by those skilled in the art to the particular sequences of the invention.

The present invention also includes nucleic acid molecules that hybridize under standard conditions to any of the nucleic acid sequences encoding the LIM mineralization proteins of the invention. "Standard hybridization conditions" will vary with the size of the probe, the background and the concentration of the nucleic acid reagents, as well as the type of hybridization, for example, in situ, Southern blot, or hybrization of DNA-RNA hybrids (Northern blot). The determination of "standard hybridization conditions" is within the level of skill in the art. For example, see U.S. Pat. No. 5,580,775 to Fremeau, et al., herein incorporated by reference for this purpose. See also, Southern, J. Mol. Biol., 98:503 (1975), Alwine, et al., Meth. Enzymol., 68:220 (1979), and Sambrook, et al., Molecular Cloning: A Laboratory Manual, 2nd edition, Cold Spring Harbor Press, 7.19-7.50 (1989).

One preferred set of standard hybrization conditions involves a blot that is prehybridized at 42° C. for 2 hours in 50% formamide, 5×SSPE (150 nM NaCl, 10 mM Na $H_2PO_4$ [pH 7.4], 1 mM EDTA [pH 8.0])l 5×Denhardt's solution (20 mg Ficoll, 20 mg polyvinylpyrrolidone and 20 mg BSA per 100 ml water), 10% dextran sulphate, 1% SDS and 100 μg/ml salmon sperm DNA. A $^{32}$P-labeled cDNA probe is added, and hybridization is continued for 14 hours. Afterward, the blot is washed twice with 2×SSPE, 0.1% SDS for 20 minutes at 22° C., followed by a 1 hour wash at 65° C. in 0.1×SSPE, 0.1% SDS. The blot is then dried and exposed to x-ray film for 5 days in the presence of an intensifying screen.

Under "highly stringent conditions," a probe will hybridize to its target sequence if those two sequences are substantially identical. As in the case of standard hybridization conditions, one of skill in the art can, given the level of skill in the art and the nature of the particular experiment, determine the conditions under which only substantially identical sequences will hybridize.

According to one aspect of the present invention, an isolated nucleic acid molecule comprising a nucleic acid sequence encoding a LIM mineralization protein is provided. The nucleic acid molecule according to the invention can be a molecule which hybridizes under standard conditions to a nucleic acid molecule complementary to the full length of SEQ. ID NO: 25 and/or which hybridizes under highly stringent conditions to a nucleic acid molecule complementary to the full length of SEQ. ID NO: 26. More specifically, the isolated nucleic acid molecule according to the invention can encode HLMP-1, HLMP-1s, RLMP, HLMP-2, or HLMP-3.

In still another embodiment, the invention relates to the identification of such proteins based on anti-LMP antibodies. In this embodiment, protein samples are prepared for Western blot analysis by lysing cells and separating the proteins by SDS-PAGE. The proteins are transferred to nitrocellulose by electroblotting as described by Ausubel, et al., Current Protocols in Molecular Biology, John Wiley and Sons (1987). After blocking the filter with instant nonfat dry milk (1 gm in 100 ml PBS), anti-LMP antibody is added to the filter and incubated for 1 hour at room temperature. The filter is washed thoroughly with phosphate buffered saline (PBS) and incubated with horseradish peroxidase (HRPO)-antibody conjugate for 1 hour at room temperature. The filter is again washed thoroughly with PBS and the antigen bands are identified by adding diaminobenzidine (DAB).

Monospecific antibodies are the reagent of choice in the present invention, and are specifically used to analyze patient cells for specific characteristics associated with the expression of LMP. "Monospecific antibody" as used herein is defined as a single antibody species or multiple antibody species with homogenous binding characteristics for LMP. "Homogeneous binding" as used herein refers to the ability of the antibody species to bind to a specific antigen or epitope, such as those associated with LMP, as described above. Monospecific antibodies to LMP are purified from mammalian antisera containing antibodies reactive against LMP or are prepared as monoclonal antibodies reactive with LMP using the technique of Kohler and Milstein. Kohler et al., Nature, 256, 495-497 (1975). The LMP specific antibodies are raised by immunizing animals such as, for example, mice, rats, guinea pigs, rabbits, goats or horses, with an appropriate concentration of LMP either with or without an immune adjuvant.

In this process, pre-immune serum is collected prior to the first immunization. Each animal receives between about 0.1 mg and about 1.0 mg of LMP associated with an acceptable immune adjuvant, if desired. Such acceptable adjuvants include, but are not limited to, Freund's complete, Freund's incomplete, alum-precipitate, water in oil emulsion containing *Corynebacterium parvum* and tRNA adjuvants. The initial immunization consists of LMP in, preferably, Freund's complete adjuvant injected at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20 C.

Monoclonal antibodies (mAb) reactive with LMP are prepared by immunizing inbred mice, preferably Balb/c mice, with LMP. The mice are immunized by the IP or SC route with about 0.1 mg to about 1.0 mg, preferably about 1.0 mg, of LMP in about 0.5 ml buffer or saline incorporated in an equal volume of an acceptable adjuvant, as discussed above. Freund's complete adjuvant is preferred. The mice receive an initial immunization on day 0 and are rested for about 3-30 weeks. Immunized mice are given one or more booster immunizations of about 0.1 to about 10 mg of LMP in a buffer solution such as phosphate buffered saline by the intravenous (IV) route. Lymphocytes from antibody-positive mice, preferably splenic lymphocytes, are obtained by removing the spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1,000 mol. wt., at concentrations from about 30% to about 50%. Fused hybridoma cells are selected by growth in hypoxanthine, thymidine and aminopterin in supplemented Dulbecco's Modified Eagles Medium (DMEM) by procedures known in the art. Supernatant fluids are collected from growth positive wells on about days 14, 18, and 21, and are screened for antibody production by an immunoassay such as solid phase immunoradioassay (SPIRA) using LMP as the antigen. The culture fluids are also tested in the Ouchterlony precipitation assay to determine the isotype of the mAb. Hybridoma cells from antibody positive wells are cloned by a technique such as the soft agar technique of MacPherson, "Soft Agar Techniques Tissue Culture Methods and Applications", Kruse and Paterson (eds.), Academic Press (1973). See, also, Harlow, et al., Antibodies: A Laboratory Manual, Cold Spring Laboratory (1988).

Monoclonal antibodies may also be produced in vivo by injection of pristane-primed Balb/c mice, approximately 0.5 ml per mouse, with about $2\times10^6$ to about $6\times10^6$ hybridoma cells about days after priming. Ascites fluid is collected at approximately 8-12 days after cell transfer and the monoclonal antibodies are purified by techniques known in the art.

In vitro production in anti-LMP mAb is carried out by growing the hydridoma cell line in DMEM containing about 2% fetal calf serum to obtain sufficient quantities of the specific mAb. The mAb are purified by techniques known in the art.

Antibody titers of ascites or hybridoma culture fluids are determined by various serological or immunological assays, which include, but are not limited to, precipitation, passive agglutination, enzyme-linked immunosorbent antibody (ELISA) technique and radioimmunoassay (RIA) techniques. Similar assays are used to detect the presence of the LMP in body fluids or tissue and cell extracts.

It is readily apparent to those skilled in the art that the above described methods for producing monospecific antibodies may be utilized to produce antibodies specific for polypeptide fragments of LMP, full-length nascent LMP polypeptide, or variants or alleles thereof.

In another embodiment, the invention is directed to alternative splice variants of HLMP-1. PCR analysis of human heart cDNA revealed mRNA for two HLMP alternative splice variants, named HLMP-2 and HLMP-3, that differ from HLMP-1 in a region between base pairs 325 and 444 in the HLMP-1 sequence. The HLMP-2 sequence has a 119 base pair deletion and an insertion of 17 base pairs in this region. These changes preserve the reading frame, resulting in a 423 amino acid protein, which compared to HLMP-1, has a net loss of 34 amino acids (40 amino acids deleted plus 6 inserted amino acids). HLMP-2 contains the c-terminal LIM domains that are present in HLMP-1.

Compared to HLMP-1, HLMP-3 has no deletions, but it does have the same 17 base pair insertion at position 444. This insertion shifts the reading frame, causing a stop codon at base pairs 459-461. As a result, HLMP-3 encodes a protein of 153 amino acids. This protein lacks the c-terminal LIM domains that are present in HLMP-1 and HLMP-2. The predicted size of the proteins encoded by HLMP-2 and HLMP-3 was confirmed by western blot analysis.

PCR analysis of the tissue distribution of the three splice variants revealed that they are differentially expressed, with specific isoforms predominating in different tissues. HLMP-1 is apparently the predominant form expressed in leukocytes, spleen, lung, placenta, and fetal liver. HLMP-2 appears to be the predominant isoform in skeletal muscle, bone marrow, and heart tissue. HLMP-3, however, was not the predominant isoform in any tissue examined.

Over-expression of HLMP-3 in secondary rat osteoblast cultures induced bone nodule formation (287±56) similar to the effect seen for glucicorticoid (272±7) and HLMP-1 (232±200). Since HLMP-3 lacks the C-terminal LIM domains, there regions are not required for osteoinductive activity.

Over-expression of HLMP-2, however, did not induce nodule formation (11±3). These data suggest that the amino acids encoded by the deleted 119 base pairs are necessary for osteoinduction. The data also suggest that the distribution of HLMP splice variants may be important for tissue-specific function. Surprisingly, we have shown that HLMP-2 inhibits steroid-induced osteoblast formation in secondary rat osteoblast cultures. Therefore, HLMP-2 may have therapeutic utility in clinical situations where bone formation is not desirable.

On Jul. 22, 1997, a sample of 10-4/RLMP in a vector designated pCMV2/RLMP (which is vector pRc/CMV2 with insert 10-4 clone/RLMP) was deposited with the American Type Culture Collection (ATCC), 12301 Parklawn Drive, Rockville, Md. 20852. The culture accession number for that deposit is 209153. On Mar. 19, 1998, a sample of the vector pHis-A with insert HLPM-1s was deposited at the American Type Culture Collection ("ATCC"). The culture accession number for that deposit is 209698. On Apr. 14, 2000, samples of plasmids pHAhLMP-2 (vector pHisA with cDNA insert derived from human heart muscle cDNA with HLMP-2) and pHAhLMP-3 (vector pHisA with cDNA insert derived from human heart muscle cDNA with HLMP-3) were deposited with the ATCC, 10801 University Blvd., Manassas, Va., 20110-2209, USA, under the conditions of the Budapest treaty. The accession numbers for these deposits are PTA-1698 and PTA-1699, respectively. These deposits, as required by the Budapest Treaty, will be maintained in the ATCC for at least 30 years and will be made available to the public upon the grant of a patent disclosing them. It should be understood that the availability of a deposit does not constitute a license to practice the subject invention in derogation of patent rights granted by government action.

According to another embodiment of the instant invention, inventors have enhance the bioavilablity of osteogenic factors within a cell. Work by Becker-Hapak et al. has shown that the TAT protein of HIV-1 can enter a wide variety of cells efficiently when added exogenously. Becker-Hapak, M., et al. (2001) TAT-mediated protein transduction into mammalian cells. Methods. 24, 247-256. TAT protein added to medium at concentrations of 1 nM can induce biological responses in the nucleus of the target cell, although the mechanisms by which the molecule is taken up and distributed within the cell are unknown. In addition, a cellular entry was demonstrated by chemically cross-linking TAT-peptides to a number of heterologous proteins otherwise impermeable to living cells. See Fawell S, et al. (1994) TAT-mediated delivery of heterologous proteins into cells. Proc. Natl. Acad. Sci. U.S.A. 91:664-668.

Of the different peptide constructs employed, it was found that the most successful was a peptide corresponding to TAT residues 37-72 and 47-59 in HIV TAT protein. See Pepinsky R B, et al. (1994) Specific inhibition of a human papillomavirus E2 trans-activator by intracellular delivery of its repressor. DNA Cell Biol. 13:1011-1019. The ability of the TAT protein to cross the plasma membrane has since been shown to reside primarily in a highly basic region composed of the 9-amino acid residues 49-57 (RKKRRQRRR) (SEQ ID No. 87). see Vogel, B. E., et al. (1993) A novel integrin specificity exemplified by binding of the R vs â 5 integrin to the basic domain of the HIV TAT protein and vitronectin, J. Cell Biol. 121, 461-468; and Wender, P. A. et al. (2000) The design, synthesis, and evaluation of molecules that enable or enhance cellular uptake: Peptoid molecular transporters, Proc. Natl. Acad. Sci. U.S.A. 97, 13003-13008. Unlike the previously described TAT-fusion proteins reported in the art, the inventors of this invention chose regulatory factors that are known to reside in the nuclear compartment and participate in transcriptional induction of bone-specific genes.

In one embodiment of the instant invention, the inventors have developed an efficient systems for delivery of osteogenic factors into the cells. Accordingly, a purified recombinant protein cargo delivered by the TAT-peptide tag was delivered for nuclear localization in such form accessible to interaction with other nuclear proteins. In this aspect of the invention, the inventors applied techniques to deliver signaling molecules as bait to eventually identify and characterize their interacting partners to determine the mode of action of each of these factors.

Transcription factors, in general, are expressed in response to specific extra and/or intracellular signals. These proteins are transiently expressed in low amounts in cells. For extensive studies on their interacting proteins in vitro, it is necessary to isolate them in large quantities. At least one objective of the present embodiment was to engineer, express and purify such factors in large quantities that can be used to develop further tools (antibodies, protein-interaction pull-down assays, protein delivery vehicles etc.) to facilitate our understanding of their mode of action in vivo.

Enrichment of desired recombinant proteins based on their molecular size prior to metal-affinity chromatography greatly improved the ease and purity of recombinant proteins. Using these strategies, the inventors were the first to obtain milligram quantities of pure LMP-1, Dlx5, Runx2 and Osterix suitable for chemical labeling studies.

Labeling of the purified fusion-proteins with FITC allowed us to monitor their entry into cells in a time and concentration dependent manner. Incubation of TAT-proteins for 30 min attained maximum cellular entry when doses of 25 nM and above were added. The inventors have also the first to demonstrate that the presence of the cationic peptide allows the TAT-tagged protein to accumulate both in the cytoplasmic and nuclear fractions in a dose dependent fashion.

Taken collectively, this aspect of the invention provides a quick purification protocol for the purification of HIV derived TAT-domain fused signaling molecules. Accordingly, the purified proteins were able to enter cells in a time and dose-dependent manner. In a more preferred embodiment of this aspect of the invention, inventors confirmed the presence of newly accumulated TAT-protein in cytoplasmic and nuclear compartments. One of ordinary skill in the art in possession of this aspect of the invention can determine the down stream interacting proteins by pull-down assays and binding assays in vitro using conventional methods in the art.

Another aspect of the invention includes the proteins encoded by the nucleic acid sequences. Specifically, according to this aspect of the invention, purified recombinant protein cargo of bone-specific mammalian transcription factors are prepared for delivery into the nucleus. More specifically, protein cargos comprise osteogenic proteins which are delivered by the TAT-peptide tag capable of nuclear localization.

In another embodiment, this invention is directed to cell expression systems and methods of use thereof to meet the demands of proteomics for large scale production of LMP proteins. According to this aspect of the invention, a method is developed to remedy the main drawback of the expression of heterologous proteins in non-mammalian hosts (e.g. bacteria, yeast, baculovirus). Inventors are thus the first to introduce a method for purifying and manufacturing LMP-1 protein by identifying LMP-1 protein internal sequencing and assessing post-translational glycosylation.

Recombinant expression of protein factors has become a powerful tool for a variety of applications ranging from basic research to human therapy. Cultured mammalian cells have become the dominant system for the production of recombinant mammalian proteins for clinical applications because of their capacity for proper protein folding, assembly and post-translational modification.

However, the expression of heterologous proteins in non-mammalian hosts (e.g. bacteria, yeast, baculovirus) results in recombinant proteins that often display poor functional and structural properties due to a lack of proper folding and/or post-translational modifications. High-level mammalian recombinant protein production mostly relies on the establishment of stably expressing cell lines. Such procedures are not only labor-intensive and time consuming, but also precludes the expression of proteins whose biological activities interfere with cell growth.

In this embodiment of the invention, the inventors show that LMP-1 protein is expressed upon plasmid-mediated transformation of mammalian cells by purifying and characterizing the identity of the protein. The inventors have purified the recombinant proteins to a suitable level of homogeneity using a novel purification and detection methods with following features: (1) size fractionation of proteins prior to metal affinity chromatography to improve efficiency of affinity resin and (2) identification of tryptic fragments of purified protein.

The appeal of this approach is the short time span of a few days between DNA delivery and protein harvest. The improvements described in this invention are readily amenable to scale-up procedures.

In yet another embodiment of this invention, inventors determined whether the expressed protein undergoes any post-translational modification. According to this aspect of the invention inventors assess the presence of carbohydrate on LMP-1 polypeptide in any suitable cell expression system which includes prokaryotic (e.g bacteria, blue green algae) and non-mammalian eukaryotic cells (e.g. insect cells, plant cells) as well as mammalian cells (e.g. A-549 cells). The inventions have further characterized the structural and functional role of the carbohydrate moiety in LMP-1 purified in normal human cells.

A549 cells, derived from a human lung adenocarcinoma, are not fully representative of normal human respiratory epithelium but have been a quick and useful in vitro model for protein expression studies. Allen and White, Am. J. Physiol., 274 (Lung Cell. Mol. Physiol. 18): L159-L164, (1998). Kazzaz et al, J. Biol. Chem., 271:15182-15186 (1996). Wong et al. J. Clin. Invest., 99: 2423-2428 (1997). The A-549 cell system has all the eukaryotic protein processing capabilities. It is generally accepted that A-549 cells can fold, modify, traffic and assemble newly synthesized polypeptides to produce highly authentic, soluble end products. The present invention provides that a full length LMP-1 is indeed expressed in A549 cells and milligram quantities of protein can be obtained from mammalian cell cultures.

According to this aspect of the invention, the inventors were able to determine that the protein did not contain carbohydrate as chemical analysis showed little or no N-acetyl glucosamine or N-acetyl galactosamine. These observations suggest to those of ordinary skill in the art that prokaryotic cell systems (e.g. bacteria) as well as non-mammalian eukaryotic cells (e.g. insect and plant cells) are suitable candidates to provide expression systems for determination of the LMP-1 mode of action and further its mass production.

In the final aspect of this invention, compositions of matter comprising LIM mineralization protein that are substantially free of carbohydrate moieties and are manufactured in accord to the instantly described method. Such compositions can further contain physiologically acceptable carrier system for in vivo administration. In assessing the nucleic acids, proteins, or antibodies of the invention, enzyme assays, protein purification, and other conventional biochemical methods are employed. DNA and RNA are analyzed by Southern blotting and Northern blotting techniques, respectively. Typically, the samples analyzed are size fractionated by gel electrophoresis. The DNA or RNA in the gels are then transferred to nitrocellulose or nylon membranes. The blots, which are replicas of sample patterns in the gels, were then hybridized with probes. Typically, the probes are radio-labeled, preferably with $^{32}P$, although one could label the probes with other signal-generating molecules known to those in the art. Specific bands of interest can then be visualized by detection systems, such as autoradiography.

For purposes of illustrating preferred embodiments of the present invention, the following, non-limiting examples are included. These results demonstrate the feasibility of inducing or enhancing the formation of bone using the LIM mineralization proteins of the invention, and the isolated nucleic acid molecules encoding those proteins.

Example 1

Calvarial Cell Culture

Rat calvarial cells, also known as rat osteoblasts ("ROB"), were obtained from 20-day pre-parturition rats as previously described. Boden. et al., Endocrinology, 137, 8, 3401-3407 (1996). Primary cultures were grown to confluence (7 days), trypsinized, and passed into 6-well plates ($1 \times 10^5$ cells/35 mm well) as first subculture cells. The subculture cells, which were confluent at day 0, were grown for an additional 7 days. Beginning on day 0, media were changed and treatments (Trm and/or BMPs) were applied, under a laminar flow hood, every 3 or 4 days. The standard culture protocol was as follows: days 1-7, MEM, 10% FBS, 50 µg/ml ascorbic acid, ±stimulus; days 8-14, BGJb medium, 10% FBS, 5 mM βGlyP (as a source of inorganic phosphate to permit mineralization). Endpoint analysis of bone nodule formation and osteocalcin secretion was performed at day 14. The dose of BMP was chosen as 50 ng/ml based on pilot experiments in this system that demonstrated a mid-range effect on the dose-response curve for all BMPs studied.

Example 2

Antisense Treatment and Cell Culture

To explore the potential functional role of LMP-1 during membranous bone formation, we synthesized an antisense oligonucleotide to block LMP-1 mRNA translation and treated secondary osteoblast cultures that were undergoing differentiation initiated by glucocorticoid. Inhibition of RLMP expression was accomplished with a highly specific antisense oligonucleotide (having no significant homologies to known rat sequences) corresponding to a 25 by sequence spanning the putative translational start site (SEQ. ID NO: 42). Control cultures either did not receive oligonucleotide or they received sense oligonucleotide. Experiments were performed in the presence (preincubation) and absence of lipofectamine. Briefly, 22 µg of sense or antisense RLMP oligonucleotide was incubated in MEM for 45 minutes at room temperature. Following that incubation, either more MEM or pre-incubated lipofectamine/MEM (7% v/v; incubated 45 minutes at room temperature) was added to achieve an oligonucleotide concentration of 0.2 µM. The resulting mixture was incubated for 15 minutes at room temperature. Oligonucleotide mixtures were then mixed with the appropriate medium, that is, MEM/Ascorbate/±Trm, to achieve a final oligonucleotide concentration of 0.1 µM.

Cells were incubated with the appropriate medium (±stimulus) in the presence or absence of the appropriate oligonucleotides. Cultures originally incubated with lipofectamine were re-fed after 4 hours of incubation (37° C.; 5% $CO_2$) with media containing neither lipofectamine nor oligonucleotide. All cultures, especially cultures receiving oligonucleotide, were re-fed every 24 hours to maintain oligonucleotide levels.

LMP-1 antisense oligonucleotide inhibited mineralized nodule formation and osteocalcin secretion in a dose-dependent manner, similar to the effect of BMP-6 oligonucleotide. The LMP-antisense block in osteoblast differentiation could not be rescued by addition of exogenous BMP-6, while the BMP-6 antisense oligonucleotide inhibition was reversed with addition of BMP-6. This experiment further confirmed the upstream position of LMP-1 relative to BMP-6 in the osteoblast differentiation pathway. LMP-1 antisense oligonucleotide also inhibited spontaneous osteoblast differentiation in primary rat osteoblast cultures.

Example 3

Quantitation of Mineralized Bone Nodule Formation

Cultures of ROBs prepared according to Examples 1 and 2 were fixed overnight in 70% ethanol and stained with von Kossa silver stain. A semi-automated computerized video image analysis system was used to quantitate nodule count and nodule area in each well. Boden. et al., Endocrinology, 137, 8, 3401-3407 (1996). These values were then divided to calculate the area per nodule values. This automated process was validated against a manual counting technique and demonstrated a correlation coefficient of 0.92 (p<0.000001). All data are expressed as the mean±standard error of the mean (S.E.M.) calculated from 5 or 6 wells at each condition. Each experiment was confirmed at least twice using cells from different calvarial preparations.

Example 4

Quantitation of Osteocalcin Secretion

OSTEOCALCIN LEVELS IN THE CULTURE MEDIA WERE MEASURED USING A COMPETITIVE radioimmunoassay with a monospecific polygonal antibody (Pab) raised in our laboratory against the C-terminal nonapeptide of rat osteocalcin as described in Nanes. et al., Endocrinology, 127:588 (1990). Briefly, 1 µg of nonapeptide was iodinated with 1 mCi $^{125}$I—Na by the lactoperoxidase method. Tubes containing 200 gl of assay buffer (0.02 M sodium phosphate, 1 mM EDTA, 0.001% thimerosal, 0.025% BSA) received media taken from cell cultures or osteocalcin standards (0-12,000 fmole) at 100 gl/tube in assay buffer. The Pab (1:40,000; 100 µl) was then added, followed by the iodinated peptide (12,000 cpm; 100 µl). Samples tested for non-specific binding were prepared similarly but contained no antibody.

Bound and free PAbs were separated by the addition of 700 µl goat antirabbit IgG, followed by incubation for 18 hours at 4° C. After samples were centrifuged at 1200 rpm for 45 minutes, the supernatants were decanted and the precipitates counted in a gamma counter. Osteocalcin values were reported in fmole/100 µl, which was then converted to pmole/ml medium (3-day production) by dividing those values by 100. Values were expressed as the mean±S.E.M. of triplicate determinations for 5-6 wells for each condition. Each experiment was confirmed at least two times using cells from different calvarial preparations.

Example 5

Effect of Trm and RLMP on Mineralization In Vitro

There was little apparent effect of either the sense or antisense oligonucleotides on the overall production of bone nodules in the non-stimulated cell culture system. When ROBs were stimulated with Trm, however, the antisense oligonucleotide to RLMP inhibited mineralization of nodules by >95%. The addition of exogenous BMP-6 to the oligonucleotide-treated cultures did not rescue the mineralization of RLMP-antisense-treated nodules. Osteocalcin has long been synonymous with bone mineralization, and osteocalcin levels have been correlated with nodule production and mineralization. The RLMP-antisense oligonucleotide significantly decreases osteocalcin production, but the nodule count in antisense-treated cultures does not change significantly. In this case, the addition of exogenous BMP-6 only rescued the production of osteocalcin in RLMP-antisense-treated cultures by 10-15%. This suggests that the action of RLMP is downstream of, and more specific than, BMP-6.

Example 6

Harvest and Purification of RNA

Cellular RNA from duplicate wells of ROBs (prepared according to Examples 1 and 2 in 6-well culture dishes) was harvested using 4M guanidine isothiocyanate (GIT) solution to yield statistical triplicates. Briefly, culture supernatant was aspirated from the wells, which were then overlayed with 0.6 ml of GIT solution per duplicate well harvest. After adding the GIT solution, the plates were swirled for 5-10 seconds (being as consistent as possible). Samples were saved at −70° C. for up to 7 days before further processing.

RNA was purified by a slight modification of standard methods according to Sambrook, et al. Molecular Cloning: a Laboratory Manual, Chapter 7.19, 2nd Edition, Cold Spring Harbor Press (1989). Briefly, thawed samples received 60 µl 2.0 M sodium acetate (pH 4.0), 550 µl phenol (water saturated) and 150 µl chloroform:isoamyl alcohol (49:1). After vortexing, the samples were centrifuged (10000×g; 20 minutes; 4° C.), the aqueous phase transferred to a fresh tube, 600 µl isopropanol was added and the RNA precipitated overnight at −20° C.

Following the overnight incubation, the samples were centrifuged (10000×g; 20 minutes) and the supernatant was aspirated gently. The pellets were resuspended in 400 µl DEPC-treated water, extracted once with phenol:chloroform (1:1), extracted with chloroform:isoamyl alcohol (24:1) and precipitated overnight at −20° C. after addition of 40 µl sodium acetate (3.0 M; pH 5.2) and 1.0 ml absolute ethanol. To recover the cellular RNA, the samples were centrifuged (10000×g; min), washed once with 70% ethanol, air dried for 5-10 minutes and resuspended in 20 µl of DEPC-treated water. RNA concentrations were calculated from optical densities that were determined with a spectrophotometer.

Example 7

Reverse Transcription-Polymerase Chain Reaction 25

Heated total RNA (5 µg in 10.5 µl total volume DEPC-H$_2$O at 65° C. for 5 minutes) was added to tubes containing 4 µl 5×MMLV-RT buffer, 2 µl dNTPs, 2 µl dT17 primer (10 µmol/ml), 0.5 µl RNAsin (40 U/ml) and 1 µl MMLV-RT (200 units/µl). The samples were incubated at 37° C. for 1 hour, then at 95° C. for 5 minutes to inactivate the MMLV-RT. The samples were diluted by addition of 80 µl of water.

Reverse-transcribed samples (5µ) were subjected to polymerase-chain reaction using standard methodologies (50 µl total volume). Briefly, samples were added to tubes containing water and appropriate amounts of PCR buffer, 25 mM MgCl$_2$, dNTPs, forward and reverse primers for glyceraldehyde 3-phosphate dehydrogenase (GAP, a housekeeping gene) and/or BMP-6, $^{32}$P-dCTP, and Taq polymerase. Unless otherwise noted, primers were standardized to run consistently at 22 cycles (94° C., 30"; 58° C., 30"; 72° C., 20").

Example 8

Quantitation of RT-PCR Products by Polyacrylamide Gel Electrophoresis (PAGE) and PhosphorImager Analysis RT-PCR products received 5 μl/tube loading dye, were mixed, heated at 65° C. for 10 min and centrifuged. Ten μl of each reaction was subjected to PAGE (12% polyacrylamide: bis; 15 V/well; constant current) under standard conditions. Gels were then incubated in gel preserving buffer (10% v/v glycerol, 7% v/v acetic acid, 40% v/v methanol, 43% deionized water) for 30 minutes, dried (80° C.) in vacuo for 1-2 hours and developed with an electronically-enhanced phosphorescence imaging system for 6-24 hours. Visualized bands were analyzed. Counts per band were plotted graphically.

Example 9

Differential Display PCR

RNA was extracted from cells stimulated with glucocorticoid (Trm, 1 nM). Heated, DNase-treated total RNA (5 μg in 10.5 μl total volume in DEPC-H$_2$O at 65° C. for 5 minutes) was reverse transcribed as described in Example 7, but H-T$_{11}$M (SEQ. ID. NO: 4) was used as the MMLV-RT primer. The resulting cDNAs were PCR-amplified as described above, but with various commercial primer sets (for example, H-T$_{11}$G (SEQ. ID NO: 4) and H-AP-10 (SEQ. ID NO: 5); GenHunter Corp, Nashville, Tenn.). Radio-labeled PCR products were fractionated by gel electrophoresis on a DNA sequencing gel. After electrophoresis, the resulting gels were dried in vacuo and autoradiographs were exposed overnight. Bands representing differentially-expressed cDNAs were excised from the gel and reamplified by PCR using the method of Conner. et al., Proc. Natl. Acad. Sci. USA, 88, 278 (1983). The products of PCR reamplification were cloned into the vector PCR-11 (TA cloning kit; InVitrogen, Carlsbad, Calif.).

Example 10

Screening of a UMR 106 Rat Osteosarcoma Cell cDNA Library

A UMR 106 library (2.5×10$^{10}$ pfu/ml) was plated at 5×10$^4$ pfu/ml onto agar plates (LB bottom agar) and the plates were incubated overnight at 37° C. Filter membranes were overlaid onto plates for two minutes. Once removed, the filters were denatured, rinsed, dried and UV cross-linked. The filters were then incubated in pre-hyridization buffer (2×PIPES [pH 6.5], 5% formamide, 1% SDS and 100 μg/ml denatured salmon sperm DNA) for 2 h at 42° C. A 260 base-pair radio-labeled probe (SEQ. ID NO: 3; $^{32}$P labeled by random priming) was added to the entire hybridization mix/filters, followed by hybridization for hours at 42° C. The membranes were washed once at room temperature (10 min, 1×SSC, 0.1% SDS) and three times at 55° C. (15 min, 0.1×SSC, 0.1% SDS).

After they were washed, the membranes were analyzed by autoradiography as described above. Positive clones were plaque purified. The procedure was repeated with a second filter for four minutes to minimize spurious positives. Plaque-purified clones were rescued as lambda SK(-) phagemids. Cloned cDNAs were sequenced as described below.

Example 11

Sequencing of Clones

Cloned cDNA inserts were sequenced by standard methods. Ausubel, et al., Current Protocols in Molecular Biology, Wiley Interscience (1988). Briefly, appropriate concentrations of termination mixture, template and reaction mixture were subjected to an appropriate cycling protocol (95° C., 30 sec; 68° C., 30 sec; 72° C., 60 sec; x25). Stop mixture was added to terminate the sequencing reactions. After heating at 92° C. for 3 minutes, the samples were loaded onto a denaturing 6% polyacrylamide sequencing gel (29:1 acrylamide: bisacrylamide). Samples were electrophoresed for about 4 hours at 60 volts, constant current. After electrophoresis, the gels were dried in vacuo and autoradiographed.

The autoradiographs were analyzed manually. The resulting sequences were screened against the databases maintained by the National Center for Biotechnology Information (NIH, Bethesda, Md.; hftp://www.ncbi.nlm.nih.gov-/) using the BLASTN program set with default parameters. Based on the sequence data, new sequencing primers were prepared and the process was repeated until the entire gene had been sequenced. All sequences were confirmed a minimum of three times in both orientations.

Nucleotide and amino acid sequences were also analyzed using the PCGENE software package (version 16.0). Percent homology values for nucleotide sequences were calculated by the program NALIGN, using the following parameters: weight of non-matching nucleotides, 10; weight of non-matching gaps, 10; maximum number of nucleotides considered, 50; and minimum number of nucleotides considered, 50.

For amino acid sequences, percent homology values were calculated using PALIGN. A value of 10 was selected for both the open gap cost and the unit gap cost.

Example 12

Cloning of RLMP cDNA

The differential display PCR amplification products described in Example 9 contained a major band of approximately 260 base pairs. This sequence was used to screen a rat osteosarcoma (UMR 106) cDNA library. Positive clones were subjected to nested primer analysis to obtain the primer sequences necessary for amplifying the full length cDNA. (SEQ. ID NOs: 11, 12, 29, 30 and 31). One of those positive clones selected for further study was designated clone 10-4.

Sequence analysis of the full-length cDNA in clone 10-4, determined by nested primer analysis, showed that clone 10-4 contained the original 260 base-pair fragment identified by differential display PCR.

Clone 10-4 (1696 base pairs; SEQ ID NO: 2) contains an open reading frame of 1371 base pairs encoding a protein having 457 amino acids (SEQ. ID NO: 1). The termination codon, TGA, occurs at nucleotides 1444-1446. The polyadenylation signal at nucleotides 1675-1680, and adjacent poly (A) $^+$tail, was present in the 3' noncoding region. There were two potential N-glycosylation sites, Asn-Lys-Thr and Asn-Arg-Thr, at amino acid positions 113-116 and 257-259 in SEQ. ID NO: 1, respectively. Two potential cAMP- and cGMP-dependent protein kinase phosphorylation sites, Ser and Thr, were found at amino acid positions 191 and 349, respectively. There were five potential protein kinase C phosphorylation sites, Ser or Thr, at amino acid positions 3, 115, 166, 219, 442. One potential ATP/GTP binding site motif A (P-loop), Gly-Gly-Ser-Asn-Asn-Gly-Lys-Thr, was determined at amino acid positions 272-279 of SEQ ID NO: 1.

In addition, two highly conserved putative LIM domains were found at amino acid positions 341-391 and 400-451. The putative LIM domains in this newly identified rat cDNA clone showed considerable homology with the LIM domains of other known LIM proteins. However, the overall homology with other rat LIM proteins was less than 25%. RLMP (also designated 10-4) has 78.5% amino acid homology to the human enigma protein (see U.S. Pat. No. 5,504,192), but only 24.5% and 22.7% amino acid homology to its closest rat homologs, CLP-36 and RIT-18, respectively.

Example 13

Northern Blot Analysis of RLMP Expression

Thirty μg of total RNA from ROBs, prepared according to Examples 1 and 2, was size fractionated by formaldehyde gel electrophoresis in 1% agarose flatbed gels and osmotically transblotted to nylon membranes. The blot was probed with a 600 base pair EcoR1 fragment of full-length 10-4 cDNA labeled with $^{32}$P-dCTP by random priming.

Northern blot analysis showed a 1.7 kb mRNA species that hybridized with the RLMP probe. RLMP mRNA was up-regulated approximately 3.7-fold in ROBs after 24 hours exposure to BMP-6. No up-regulation of RMLP expression was seen in BMP-2 or BMP-4-stimulated ROBs at 24 hours.

Example 14

Statistical Methods

For each reported nodule/osteocalcin result, data from 5-6 wells from a representative experiment were used to calculate the mean.+-.S.E.M. Graphs may be shown with data normalized to the maximum value for each parameter to allow simultaneous graphing of nodule counts, mineralized areas and osteocalcin.

For each reported RT-PCR, RNase protection assay or Western blot analysis, data from triplicate samples of representative experiments, were used to determine the mean.+-.S.E.M. Graphs may be shown normalized to either day 0 or negative controls and expressed as fold-increase above control values.

Statistical significance was evaluated using a one-way analysis of variance with post-hoc multiple comparison corrections of Bonferroni as appropriate. D. V. Huntsberger, "The Analysis of Variance", Elements of Statistical Variance, P. Billingsley (ed.), Allyn & Bacon Inc., Boston, Mass., 298-330 (1977) and SigmaStat, Jandel Scientific, Corte Madera, Calif. Alpha levels for significance were defined as p<0.05.

Example 15

Detection of Rat LIM Mineralization Protein by Western Blot Analysis

Polyclonal antibodies were prepared according to the methods of England, et al., Biochem. Biophys. Acta, 623, 171 (1980) and Timmer, et al., J. Biol. Chem., 268, 24863 (1993).

HeLa cells were transfected with pCMV2/RLMP. Protein was harvested from the transfected cells according to the method of Hair, et al., Leukemia Research, 20, 1 (1996). Western Blot Analysis of native RLMP was performed as described by Towbin, et al., Proc. Natl. Acad. Sci. USA, 76:4350 (1979).

Example 16

Synthesis of the Rat LMP-Unique (RLMPU) Derived Human PCR Product

Based on the sequence of the rat LMP-1 cDNA, forward and reverse PCR primers (SEQ. ID NOS: 15 and 16) were synthesized and a unique 223 base-pair sequence was PCR amplified from the rat LMP-1 cDNA. A similar PCR product was isolated from human MG63 osteosarcoma cell cDNA with the same PCR primers.

RNA was harvested from MG63 osteosarcoma cells grown in T-75 flasks. Culture supernatant was removed by aspiration and the flasks were overlayed with 3.0 ml of GIT solution per duplicate, swirled for 5-10 seconds, and the resulting solution was transferred to 1.5 ml eppendorf tubes (6 tubes with 0.6 ml/tube). RNA was purified by a slight modification of standard methods, for example, see Sambrook, et al., Molecular Cloning: A Laboratory Manual, Chapter 7, page 19, Cold Spring Harbor Laboratory Press (1989) and Boden, et al., Endocrinology, 138, 2820-2828 (1997). Briefly, the 0.6 ml samples received 60 μl 2.0 M sodium acetate (pH 4.0), 550 μl water saturated phenol and 150 μl chloroform:isoamyl alcohol (49:1). After addition of those reagents, the samples were vortexed, centrifuged (10000×g; 20 min; 4 C) and the aqueous phase transferred to a fresh tube. Isopropanol (600, μl) was added and the RNA was precipitated overnight at −20° C. The samples were centrifuged (10000×g; 20 minutes) and the supernatant was aspirated gently. The pellets were resuspended in 400 μl of DEPC-treated water, extracted once with phenol:chloroform (1:1), extracted with chloroform:isoamyl: alcohol (24:1) and precipitated overnight at −20° C. in 40 μl sodium acetate (3.0 M; pH 5.2) and 1.0 ml absolute ethanol. After precipitation, the samples were centrifuged (10000×g; 20 min), washed once with 70% ethanol, air dried for 5-10 minutes and resuspended in 20 μl of DEPC-treated water. RNA concentrations were derived from optical densities.

Total RNA (5 μg in 10.5 μl total volume in DEPC-H$_2$O) was heated at 65° C. for 5 minutes, and then added to tubes containing 4 μl 5×MMLV-RT buffer, 2 μl dNTPS, 2 μl dT17 primer (10 μmol/ml), 0.5 μl RNA sin(40 U/ml) and 1 μl MMLV-RT (200 units/μl). The reactions were incubated at 37° C. for 1 hour. Afterward, the MMLV-RT was inactivated by heating at 95° C. for 5 minutes. The samples were diluted by addition of 80 μl water.

Transcribed samples (5 μl) were subjected to polymerase-chain reaction using standard methodologies (50 μl total volume). Boden, et al., Endocrinology, 138, 2820-2828 (1997); Ausubel, et al., "Quantitation of Rare DNAs by the Polymerase Chain Reaction", Current Protocols in Molecular Biology, Chapter 15.31-1, Wiley & Sons, Trenton, N.J. (1990). Briefly, samples were added to tubes containing water and appropriate amounts of PCR buffer (25 mM MgCl$_2$, dNTPs, forward and reverse primers (for RLMPU; SEQ. ID NOS: 15 and 16), $^{32}$P-dCTP, and DNA polymerase. Primers were designed to run consistently at 22 cycles for radioactive band detection and 33 cycles for amplification of PCR product for use as a screening probe (94° C., 30 sec, 58° C., 30 sec; 72° C., 20 sec).

Sequencing of the agarose gel-purified MG63 osteosarcoma-derived PCR product gave a sequence more than 95% homologous to the RLMPU PCR product. That sequence is designated HLMP unique region (HLMPU; SEQ. ID NO: 6).

Example 17

Screening of Reverse-Transcriptase-Derived MG63 cDNA

Screening was performed with PCR using specific primers (SEQ. ID NOS:16 and 17) as described in Example 7. A 717 base-pair MG63 PCR product was agarose gel purified and sequenced with the given primers (SEQ. ID NOs: 12, 15, 16, 17, 18, 27 and 28). Sequences were confirmed a minimum of two times in both directions. The MG63 sequences were aligned against each other and then against the full-length rat LMP cDNA sequence to obtain a partial human LMP cDNA sequence (SEQ. ID NO: 7).

Example 18

Screening of a Human Heart cDNA Library

Based on Northern blot experiments, it was determined that LMP-1 is expressed at different levels by several different tissues, including human heart muscle. A human heart cDNA library was therefore examined. The library was plated at $5\times10^4$ pfu/ml onto agar plates (LB bottom agar) and plates were grown overnight at 37° C. Filter membranes were overlaid onto the plates for two minutes. Afterward, the filters were denatured, rinsed, dried, UV cross-linked and incubated in pre-hyridization buffer (2×PIPES [pH 6.5]; 5% formamide, 1% SDS, 100 g/ml denatured salmon sperm DNA) for 2 h at 42° C. A radio-labeled, LMP-unique, 223 base-pair probe ($^{32}$P, random primer labeling; SEQ ID NO: 6) was added and hybridized for 18 h at 42° C. Following hybridization, the membranes were washed once at room temperature (10 min, 1×SSC, 0.1% SDS) and three times at 55° C. (15 min, 0.1×SSC, 0.1% SDS). Double-positive plaque-purified heart library clones, identified by autoradiography, were rescued as lambda phagemids according to the manufacturers' protocols (Stratagene, La Jolla, Calif.).

Restriction digests of positive clones yielded cDNA inserts of varying sizes. Inserts greater than 600 base-pairs in length were selected for initial screening by sequencing. Those inserts were sequenced by standard methods as described in Example 11.

One clone, number 7, was also subjected to automated sequence analysis using primers corresponding to SEQ. ID NOS: 11-14, 16 and 27. The sequences obtained by these methods were routinely 97-100% homologous. Clone 7 (Partial Human LMP-1 cDNA from a heart library; SEQ. ID NO: 8) contained a sequence that was more than 87% homologous to the rat LMP cDNA sequence in the translated region.

Example 19

Determination of Full-Length Human LMP-1 cDNA

Overlapping regions of the MG63 human osteosarcoma cell cDNA sequence and the human heart cDNA clone 7 sequence were used to align those two sequences and derive a complete human cDNA sequence of 1644 base-pairs. NALIGN, a program in the PCGENE software package, was used to align the two sequences. The overlapping regions of the two sequences constituted approximately 360 base-pairs having complete homology except for a single nucleotide substitution at nucleotide 672 in the MG63 cDNA (SEQ. ID NO: 7) with clone 7 having an "A" instead of a "G" at the corresponding nucleotide 516 (SEQ. ID NO: 8).

The two aligned sequences were joined using SEQIN, another subprogram of PCGENE, using the "G" substitution of the MG63 osteosarcoma cDNA clone. The resulting sequence is shown in SEQ. ID NO: 9. Alignment of the novel human-derived sequence with the rat LMP-1 cDNA was accomplished with NALIGN. The full-length human LMP-1 cDNA sequence (SEQ. ID NO: 9) is 87.3% homologous to the translated portion of rat LMP-1 cDNA sequence.

Example 20

Determination of Amino Acid Sequence of Human LMP-1

The putative amino acid sequence of human LMP-1 was determined with the PCGENE subprogram TRANSL. The open reading frame in SEQ. ID NO: 9 encodes a protein comprising 457 amino acids (SEQ. ID NO: 10). Using the PCGENE subprogram PALIGN, the human LMP-1 amino acid sequence was found to be 94.1% homologous to the rat LMP-1 amino acid sequence.

Example 21

Determination of the 5' Untranslated Region of the Human LMP cDNA

MG63 5' cDNA was amplified by nested RT-PCR of MG63 total RNA using a 5' rapid amplification of cDNA ends (5' RACE) protocol. This method included first strand cDNA synthesis using a lock-docking oligo (dT) primer with two degenerate nucleotide positions at the 3' end (Chenchik. et al., CLONTECHniques, X:5 (1995); Borson, et al., PC Methods Applic., 2, 144 (1993)). Second-strand synthesis is performed according to the method of Gubler, et al., Gene, 2, 263 (1983), with a cocktail of *Escherichia coli* DNA polymerase 1, RNase H, and *E. coli* DNA ligase. After creation of blunt ends with T4 DNA polymerase, double-stranded cDNA was ligated to the fragment (5'-CTAATACGACTCACTATAGGGCTC-GAGCGGCCGCCCGGGCAGGT-3') (SEQ. ID NO: 19). Prior to RACE, the adaptor-ligated cDNA was diluted to a concentration suitable for Marathon RACE reactions (1:50). Adaptor-ligated double-stranded cDNA was then ready to be specifically cloned.

First-round PCR was performed with the adaptor-specific oligonucleotide, 5'-CCATCCTAATACGACTCACTAT-AGGGC-3' (AP1) (SEQ. ID NO: 20) as sense primer and a Gene Specific Primer (GSP) from the unique region described in Example 16 (HLMPU). The second round of PCR was performed using a nested primers GSP1—HLMPU (antisense/reverse primer) (SEQ. ID NO: 23) and GSP2—HLMPUF (SEQ. ID NO: 24) (see Example 16; sense/forward primer). PCR was performed using a commercial kit (Advantage cDNA PCR core kit; CloneTech Laboratories Inc., Palo Alto, Calif.) that utilizes an antibody-mediated, but otherwise standard, hot-start protocol. PCR conditions for MG63 cDNA included an initial hot-start denaturation (94° C., 60 sec) followed by: 94° C., 30 sec; 60° C., 30 sec; 68° C., 4 min; cycles. The firstround PCR product was approximately 750 base-pairs in length whereas the nested PCR product was approximately 230 base-pairs. The first-round PCR product was cloned into linearized pCR 2.1 vector (3.9 Kb). The inserts were sequenced in both directions using M13 Forward and Reverse primers (SEQ. ID NO: 11; SEQ. ID NO: 12).

Example 22

Determination of Full-Length Human LMP-1 cDNA with 5' UTR

Overlapping MG63 human osteosarcoma cell cDNA 5'-UTR sequence (SEQ. ID NO: 21), MG63 717 base-pair sequence (Example 17; SEQ. ID NO: 8) and human heart cDNA clone 7 sequence (Example 18) were aligned to derive a novel human cDNA sequence of 1704 base-pairs (SEQ. ID NO: 22). The alignment was accomplished with NALIGN, (both PCGENE and Omiga 1.0; Intelligenetics). Over-lapping sequences constituted nearly the entire 717 base-pair region (Example 17) with 100% homology. Joining of the aligned sequences was accomplished with SEQIN.

Example 23

Construction of LIM Protein Expression Vector

The construction of pHIS-5ATG LMP-1s expression vector was carried out with the sequences described in Examples 17 and 18. The 717 base-pair clone (Example 17; SEQ. ID NO: 7) was digested with ClaI and EcoRV. A small fragment (~250 base-pairs) was gel purified. Clone 7 (Example 18; SEQ. ID NO: 8) was digested with ClaI and XbaI and a 1400 base-pair fragment was gel purified. The isolated 250 base-pair and 1400 base-pair restriction fragments were ligated to form a fragment of ~1650 base-pairs.

Due to the single nucleotide substitution in Clone 7 (relative to the 717 base-pair PCR sequence and the original rat sequence) a stop codon at translated base-pair 672 resulted. Because of this stop codon, a truncated (short) protein was encoded, hence the name LMP-1s. This was the construct used in the expression vector (SEQ. ID NO: 32). The full length cDNA sequence with 5' UTR (SEQ. ID NO: 33) was created by alignment of SEQ. ID NO: 32 with the 5' RACE sequence (SEQ. ID NO: 21). The amino acid sequence of LMP-1s (SEQ. ID NO: 34) was then deduced as a 223 amino acid protein and confirmed by Western blot (as in Example 15) to run at the predicted molecular weight of ~23.7 kD.

The pHis-ATG vector (InVitrogen, Carlsbad, Calif.) was digested with EcoRV and XbaI. The vector was recovered and the 650 base-pair restriction fragment was then ligated into the linearized pHis-ATG. The ligated product was cloned and amplified. The pHis-ATG-LMP-1s Expression vector, also designated pHIS-A with insert HLMP-1s, was purified by standard methods.

Example 24

Induction of Bone Nodule Formation and Mineralization In Vitro with LMP Expression Vector Rat Calvarial cells were isolated and grown in secondary culture according to Example 1. Cultures were either unstimulated or stimulated with glucocorticoid (GC) as described in Example 1. A modification of the Superfect Reagent (Qiagen, Valencia, Calif.) transfection protocol was used to transfect 3 µg/well of each vector into secondary rat calvarial osteoblast cultures according to Example 25. Mineralized nodules were visualized by Von Kossa staining, as described in Example 3.

Human LMP-1s gene product over expression alone induced bone nodule formation (~203 nodules/well) in vitro. Levels of nodules were approximately 50% of those induced by the GC positive control (~412 nodules/well). Other positive controls included the pHisA-LMP-Rat expression vector (~152 nodules/well) and the pCMV2/LMP-Rat-Fwd Expression vector (~206 nodules/well), whereas the negative controls included the pCMV2/LMP-Rat-Rev. expression vector (~2 nodules/well) and untreated (NT) plates (~4 nodules/well). These data demonstrate that the human cDNA was at least as osteoinductive as the rat cDNA. The effect was less than that observed with GC stimulation, most likely due to sub-optimal doses of Expression vector.

Example 25

LMP-Induced Cell Differentiation In Vitro and In Vivo

The rat LMP cDNA in clone 10-4 (see Example 12) was excised from the vector by double-digesting the clone with NotI and ApaI overnight at 37° C. Vector pCMV2 MCS (InVitrogen, Carlsbad, Calif.) was digested with the same restriction enzymes. Both the linear cDNA fragment from clone 10-4 and pCMV2 were gel purified, extracted and ligated with T4 ligase. The ligated DNA was gel purified, extracted and used to transform *E. coli* JM109 cells for amplification. Positive agar colonies were picked, digested with NotI and ApaI and the restriction digests were examined by gel electrophoresis. Stock cultures were prepared of positive clones.

A reverse vector was prepared in analogous fashion except that the restriction enzymes used were XbaI and HindIII. Because these restriction enzymes were used, the LMP cDNA fragment from clone 10-4 was inserted into pRc/CMV2 in the reverse (that is, non-translatable) orientation. The recombinant vector produced is designated pCMV2/RLMP.

An appropriate volume of pCMV10-4 (60 nM final concentration is optimal [3 µg]; for this experiment a range of 0-600 nM/well [0-30 µg/well] final concentration is preferred) was resuspended in Minimal Eagle Media (MEM) to 450 µl final volume and vortexed for 10 seconds. Superfect was added (7.5 µl/ml final solution), the solution was vortexed for 10 seconds and then incubated at room temperature for 10 minutes. Following this incubation, MEM supplemented with 10% FBS (1 ml/well; 6 ml/plate) was added and mixed by pipetting.

The resulting solution was then promptly pipetted (1 ml/well) onto washed ROB cultures. The cultures were incubated for 2 hours at 37° C. in a humidified atmosphere containing 5% $CO_2$. Afterward, the cells were gently washed once with sterile PBS and the appropriate normal incubation medium was added.

Results demonstrated significant bone nodule formation in all rat cell cultures which were induced with pCMV10-4. For example, pCMV10-4 transfected cells produced 429 nodules/well. Positive control cultures, which were exposed to Trm, produced 460 nodules/well. In contrast, negative controls, which received no treatment, produced 1 nodule/well. Similarly, when cultures were transfected with pCMV10-4 (reverse), no nodules were observed.

For demonstrating de novo bone formation in vivo, marrow was aspirated from the hind limbs of 4-5 week old normal rats (µ/+; heterozygous for recessive athymic condition). The aspirated marrow cells were washed in alpha MEM, centrifuged, and RBCs were lysed by resuspending the pellet in 0.83% $NH_4Cl$ in 10 mM Tris (pH 7.4). The remaining marrow cells were washed 3× with MEM and transfected for 2 hours with 9 µg of pCMV-LMP-1s (forward or reverse orientation)

per 3×10^6 cells. The transfected cells were then washed 2× with MEM and resuspended at a concentration of 3×10^7 cells/ml.

The cell suspension (100 μl) was applied via sterile pipette to a sterile 2×5 mm type I bovine collagen disc (Sulzer Orthopaedics, Wheat Ridge, Colo.). The discs were surgically implanted subcutaneously on the skull, chest, abdomen or dorsal spine of 4-5 week old athymic rats (rnu/rnu). The animals were sacrificed at 3-4 weeks, at which time the discs or surgical areas were excised and fixed in 70% ethanol. The fixed specimens were analyzed by radiography and undecalcified histologic examination was performed on 5 μm thick sections stained with Goldner Trichrome. Experiments were also performed using devitalized (guanidine extracted) demineralized bone matrix (Osteotech, Shrewsbury, N.J.) in place of collagen discs.

Radiography revealed a high level of mineralized bone formation that conformed to the form of the original collagen disc containing LMP-1s transfected marrow cells. No mineralized bone formation was observed in the negative control (cells transfected with a reverse-oriented version of the LMP-1s cDNA that did not code for a translated protein), and absorption of the carrier appeared to be well underway.

Histology revealed new bone trabeculae lined with osteoblasts in the LMP-1s transfected implants. No bone was seen along with partial resorption of the carrier in the negative controls.

Radiography of a further experiment in which 18 sets (9 negative control pCMV-LMP-REV & 9 experimental pCMV-LMP-1s) of implants were added to sites alternating between lumbar and thoracic spine in athymic rats demonstrated 0/9 negative control implants exhibiting bone formation (spine fusion) between vertebrae. All nine of the pCMV-LMP-1s treated implants exhibited solid bone fusions between vertebrae.

Example 26

Cloning of Human LMP-1 cDNA into TAT-HA Vector

The restriction and modifying enzymes in examples 26-38 were purchased from Promega (Madison, Wis.) and the bacterial host strain, BL21 (DE3) was from Stratagene (La Jolla, Calif.). The TAT-vector was a generous gift from Steven F Dowdy (Howard Hughes Medical Institute, St. Louis, Mo.). The chelating affinity resin (Probond) was purchased from Invitrogen (San Diego, Calif.). The Sephacryl S-100 (HiPrep 16×60) and other chromatographic columns and AKTA FPLC system were from Amersham-Pharmacia Biotech (Piscataway, N.J.). Fluorescent tag, fluorescein isothiocyanate (FITC) was from Pierce (Rockford, Ill.). All other chemicals and reagents, unless otherwise noted, were from Sigma (St. Louis, Mo.) (analytical grade).

*Escherichia coli* BL21 (DE3) host cells were maintained on LB agar plates and grown at 37° C. in the presence of ampicillin at 100 mg/mL. The strains were stored in LB medium containing 15% glycerol at −80° C. All cloning methods including PCR, restriction digestion, ligations, *E. coli* transformation and plasmid DNA preparation were performed according to standard protocols.

Figure 18:
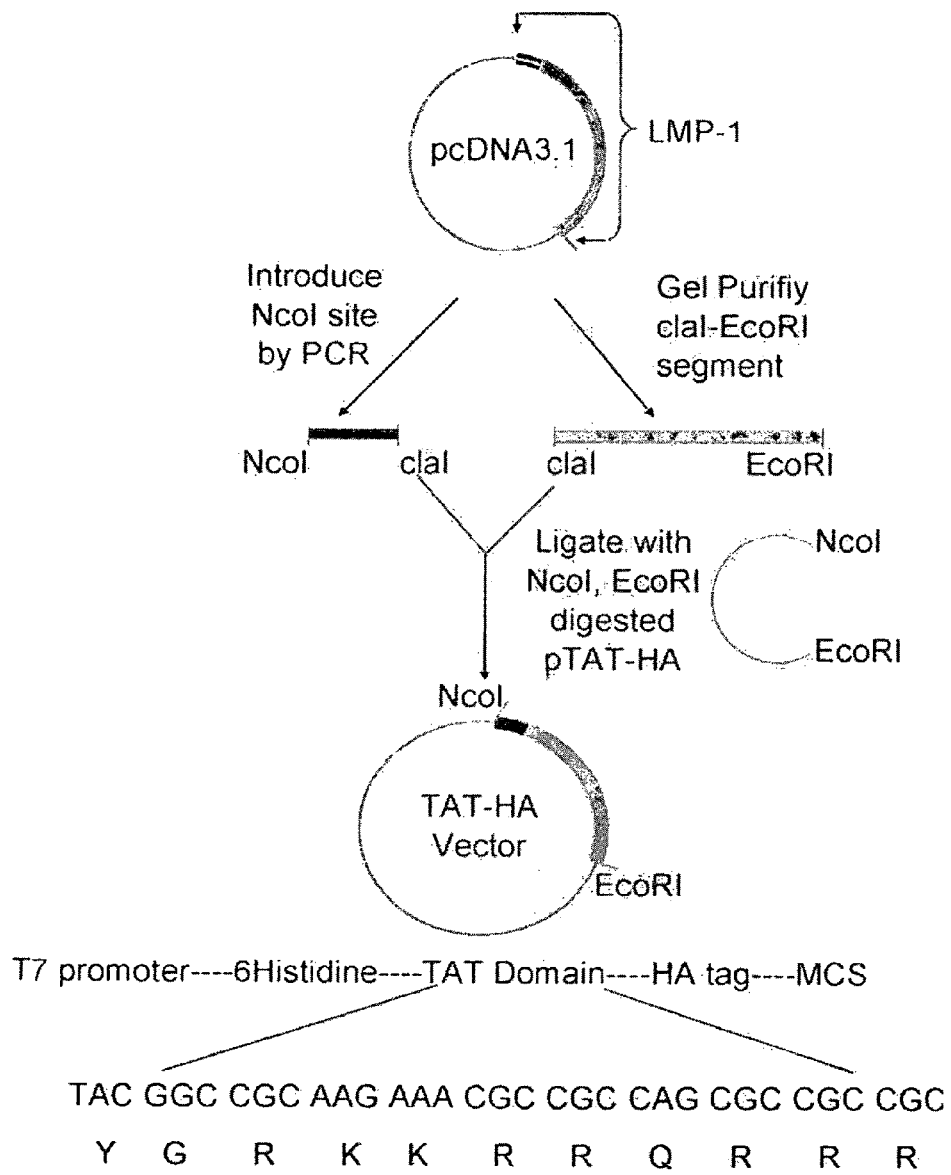
FIG. 18 is a depiction of general strategy for construction and cloning of TAT-cDNA for expression in *E. coli*. The cDNA for signaling factors, LMP-1, Dlx-5, Runx2 or Osterix, were cloned downstream to hexahistidine, TAT-domain and hemaglutinin tags driven by T7 promoter in TAT vector. Collectively the tags add an apparent molecular size of about 5 kDa to each fusion-protein.
Figure 19:
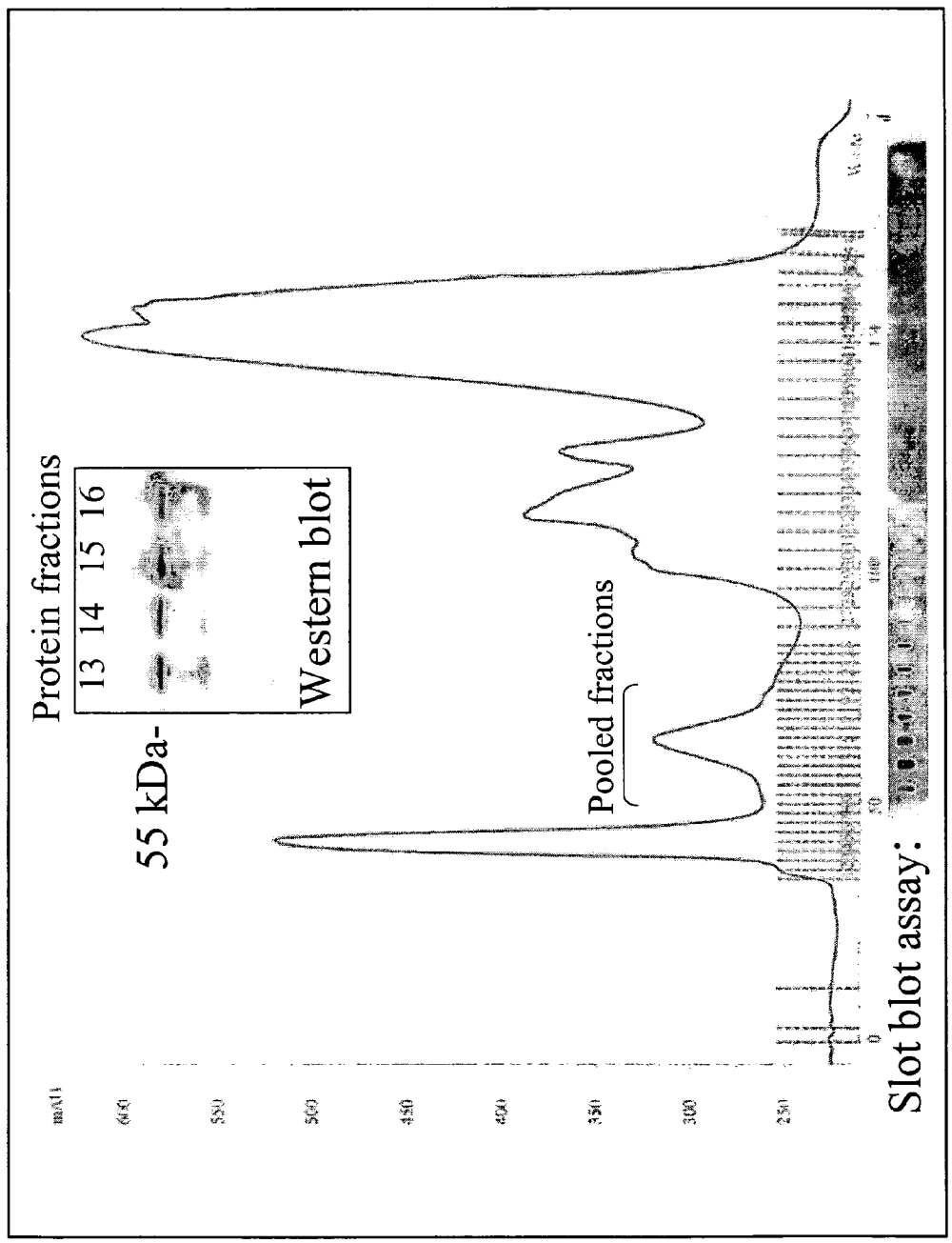
FIG. 19 is a Sephacryl S-100 molecular exclusion chromatographic profiles obtained for the bacterial crude lysates for LMP-1. The clarified bacterial lysate was applied to Sephacryl 5-100 column (HiPrep 16×60) using the AKTA FPLC/Unicorn 3.1 System in 50 mM phosphate buffer, pH 7.5 and 5 M NaCl. After the void volume eluted from the column, fractions (4 ml) were collected. Fractions containing fusion proteins were detected by slot blots and western blots with hemagglutinin-specific antibody and pooled for $Ni^{++}$-affinity enrichment. Inclusion of 5 M NaCl in buffer avoided non-specific aggregation of recombinant proteins on column resin.
Figure 20:
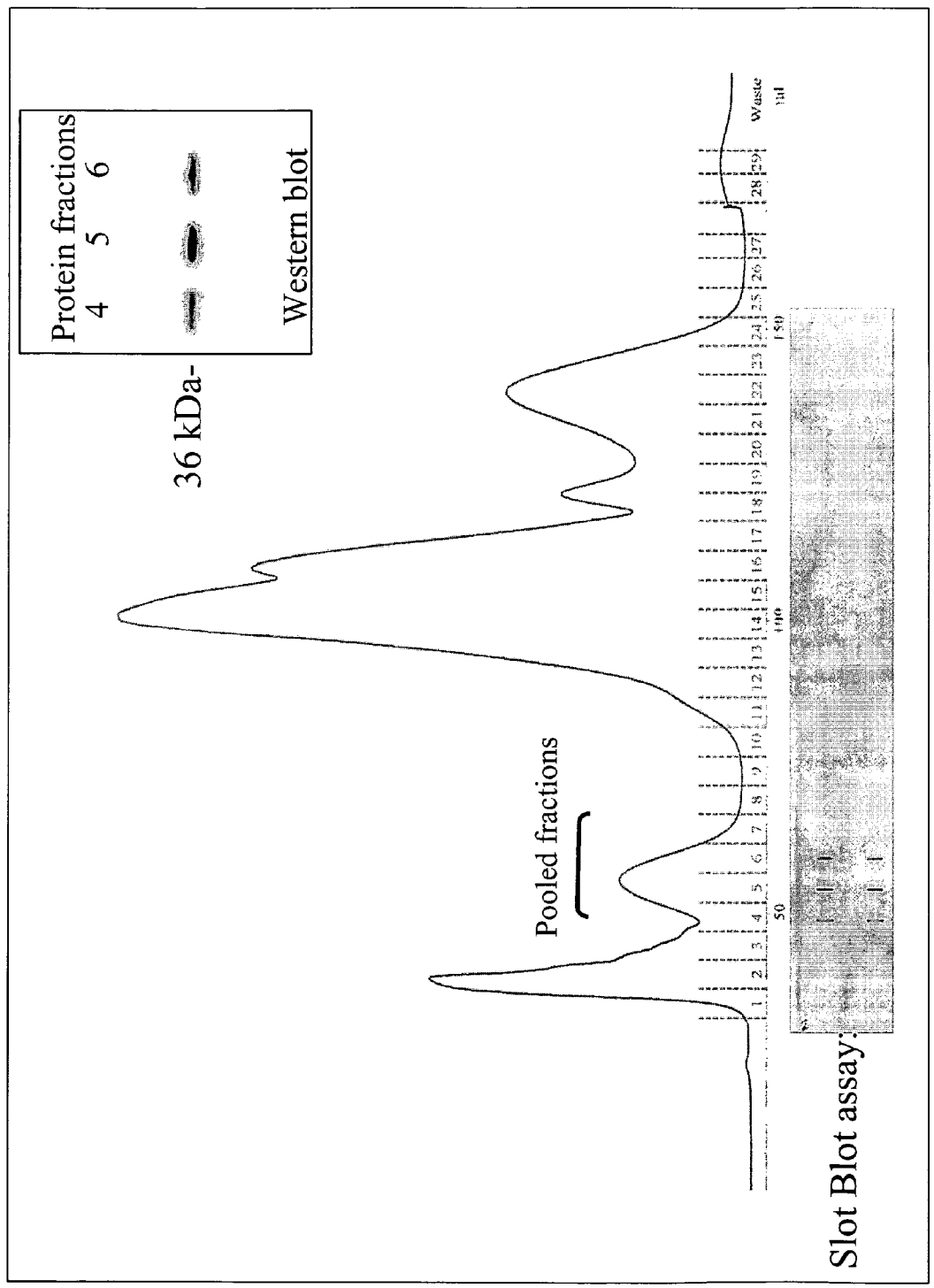
FIG. 20 is a Sephacryl S-100 molecular exclusion chromatographic profiles obtained for the bacterial crude lysates for Dlx5. same method was employed as for LMP-1 in FIG. 19.
Figure 21:
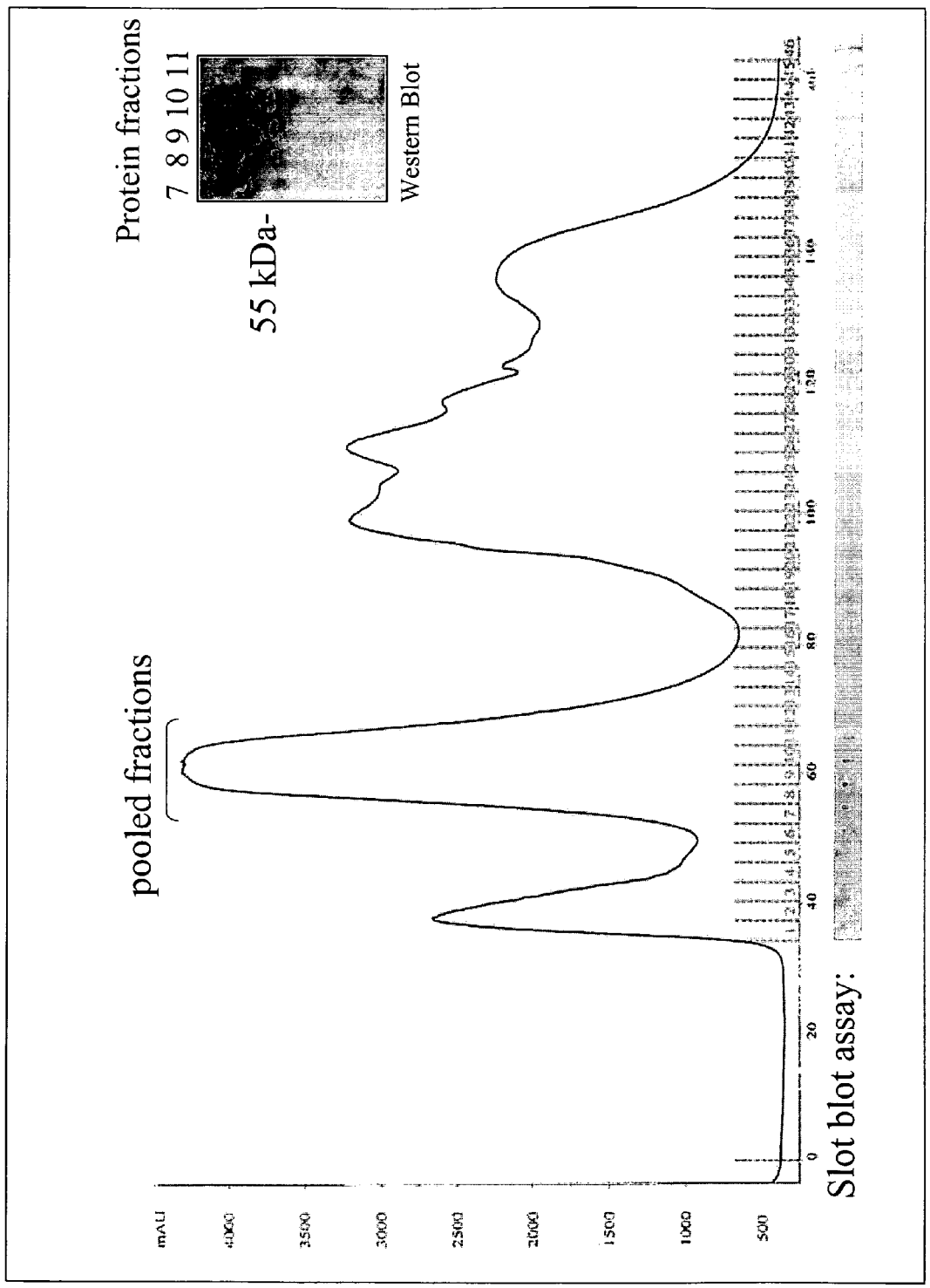
FIG. 21 is a Sephacryl S-100 molecular exclusion chromatographic profiles obtained for the bacterial crude lysates for Runx2. Same method was employed as for FIG. 19.
Figure 22:
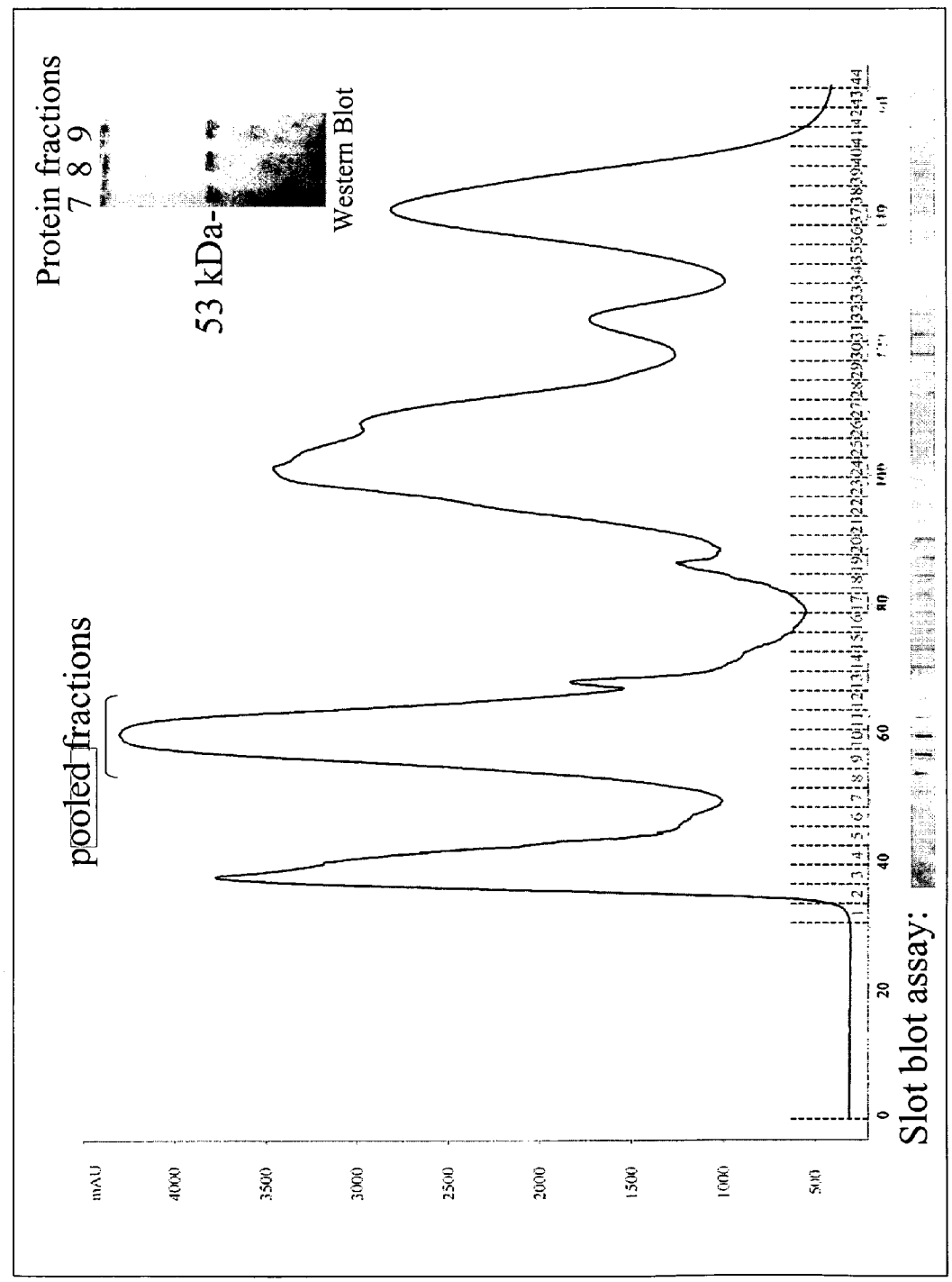
FIG. 22 is a Sephacryl S-100 molecular exclusion chromatographic profiles obtained for the bacterial crude lysates for Osx. Same method was employed as for FIG. 19.
Figure 23:
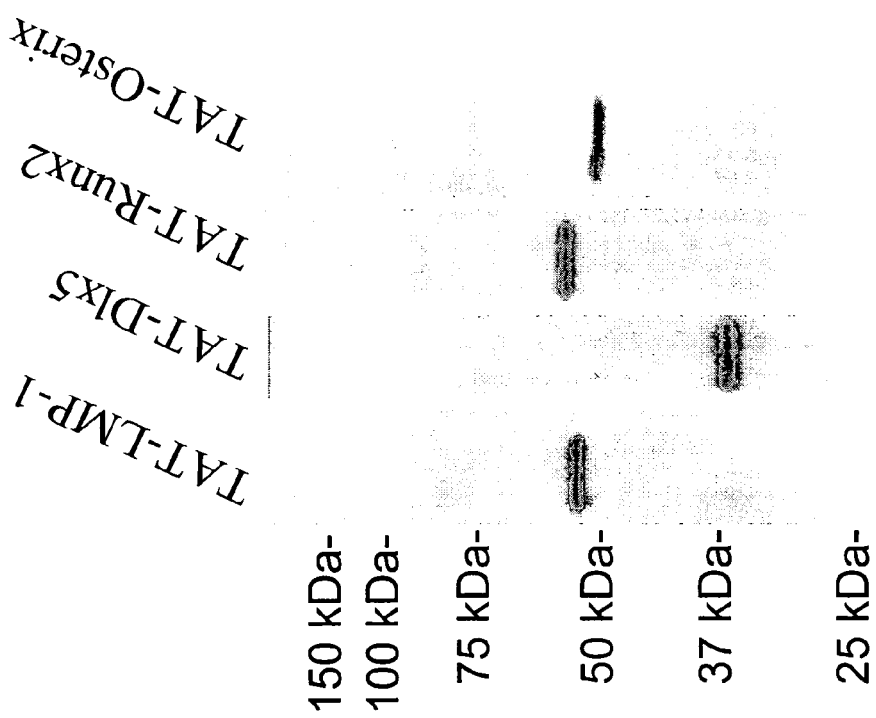
FIG. 23 is a depiction of SDS-PAGE of purified LMP-1, Dlx5, Runx2 and Osterix. Purified protein fractions were concentrated, dialyzed and a 5 ug aliquot of each recombinant protein was loaded. The purity of each preparation was determined by coomassie staining of gels after SDS-PAGE (12% acrylamide). Each of the fusion-protein was the expected size as determined from molecular weight markers as marked.

For human LMP-1 the Polymerase chain reaction (PCR) was performed with forward primer: 5'-CCATGGATTCCT-TCAAAGTAGTGC-3' (SEQ ID NO: 75), reverse primer: 5'-CAGGGCGGGCGGCTGGTAG-3' (SEQ ID NO: 76) using the template cDNA plasmid under the conditions: 95° C. 2 min, (95° C. 30 Sec, 66° C. 30 Sec, 72° C. 1 min)×25, 72° C. 10 min. The PCR product was cloned into the PCRII-TOPO vector (Invitrogen) and the sequence was verified by sequencing both the complimentary strands. The desired clone was digested with NcoI and ClaI. The insert was gel-purified (Fragment A). The pCDNA3.1/hLMP-1 clone was digested with ClaI and EcoRI and the inserts were gel purified (Fragment B). Similarly, pTAT-HA vector was digested with NcoI and EcoRI and the vector was gel purified (Fragment C). The fragments, A, B, and C were ligated to obtain the desired construct (FIG. 18). BL21 (DE3) competent cells were transformed with plasmid by standard methods (Novagen) and the correct clones were selected by restriction analysis followed by DNA sequencing.

Example 27

Cloning of Mouse Dlx5 into TAT-HA Vector

For mouse Dlx5 the PCR was performed with forward primer: 5'-CCATGGCAGGAGTGTTTGACAGAAGAGT-3' (SEQ ID NO: 77)

and reverse primer:

5'-TAATAAAGCGTCCCGGAGGCC-3' (SEQ ID NO: 78)

using the template cDNA plasmid under the conditions: 95° C. for 1 min (94° C. 30 sec, 66° C. 30 sec, 72° C. for 2 min)×35 cycles, 72° C. 10 min. The PCR product was then cloned into PCR 2.1 vector (invitrogen) and the insert sequence was verified by sequencing. The desired clone was digested with NcoI and XhoI, and the insert was recovered from gel (Fragment A). Similarly the pTAT-HA vector was digested with NcoI and XhoI, and the vector was recovered (Fragment B). Ligation of fragment A and B yielded the desired construct. BL21 (DE3) competent cells were transformed with plasmid by standard methods (Novagen) and the correct clones were selected by restriction analysis followed by DNA sequencing.

Example 28

Cloning of Mouse Runx2 into TAT-HA Vector

Two oligonucleotide primers (SEQ ID NOS 79-80) (Runx2-forward primer: 5'-catggcgtcaaacagcctcttcagcg-cagtgacaccgtgtcagcaaagcttcttttgg-3' Runx2-reverse primer: 5' gatcccaaaagaagctttgctgacacg-gtgtcactgcgctgaagaggctgtttgacgc-3') corresponding to the 5' sequence of mouse Runx2 cDNA were designed and annealed together with a NcoI site at the ATG translation start site and a BamH1 site at the 3' end matching that site in the Runx2 cDNA sequence (Fragment A). The pAV-CMV-CB-FAIII-iresGFP clone (Dr. Mirek Kozlowski, Emory University) was digested with BamHI and EcoRV and the insert was recovered (Fragment B).

TAT-HA vector was digested with XhoI, followed by treatment with T4 DNA Polymerase to create a blunt end. The vector was then digested again with NcoI to recover the fragment for ligations (Fragment C). Ligation of fragments A, B and C yielded the desired construct. BL21 (DE3) competent cells were transformed with plasmid by standard methods (Novagen) and the correct clones were selected by restriction analysis followed by DNA sequencing.

Example 29

Cloning of Mouse Osterix cDNA into TAT-HA Vector

Two oligonucleotide primers (SEQ ID NOS 81-82) (Osx-forward primer: 5'-catggcgtcctctctgcttgaggaa-gaagctcactatggctccagtccctggccatgctgactgcagccg-3'
Osx-reverse primer: 5'-gatccggctgcagtcagcatggccaggg-gactggagccatagtgagcttcttcctcaagcagagaggacgc-3'
corresponding to the 5' sequence of mouse Osterix cDNA (which was absent in the pCDNA5UTFlag Osx clone) were designed and annealed together with a NcoI site at the ATG translation start site and a BamHI site at the 3' end, which matched that site in the osterix cDNA clone (Fragment A). The pCDNA5UTFlagOsx clone was digested with BamHI and HindIII, and the insert was recovered (Fragment B). The TAT-HA vector was digested with XhoI, followed by treatment with T4 DNA Polymerase to create a blunt end. The vector was then digested again with NcoI to recover the vector (Fragment C). Ligation of fragment A, B and C yielded the desired construct. BL21 (DE3) competent cells were transformed with plasmid by standard methods (Novagen) and the correct clones were selected by restriction analysis followed by DNA sequencing.

Example 30

Bacterial Culture and Induction of Recombinant Proteins

A single colony of BL21 (DE3) host grown on LB plate (100 ug/ml ampicillin) was inoculated into 10 ml LB broth containing 100 mg/mL Amp and incubated at 37° C. on a rotary shaker shaking at 250 RPM overnight. The culture was used to inoculate 2×500 ml LB broth containing 100 ug/ml Amp in a 2-liter flask (two) and grown at 37° C. until $O.D_{600}$ reached 0.80. Isopentenyl thiogalactoside (IPTG) was added to 200 uM and the culture continued to grow for another 6 hrs at 37° C. Cells were harvested in 250-ml centrifuge tubes, spun at 3000×g at 4° C. (Beckman Rotor #10, 6500 RPM) for 15 min and the pellets were store at −70° C.

Example 31

Sephacryl S-100 Molecular Exclusion Chromatography

Size-exclusion chromatography of the proteins was carried out on a Sephacryl S-100 column connected to the AKTA FPLC System (Amersham Biosciences, Piscataway, N.J.). The column was pre-calibrated with known low- and high-molecular weight protein markers from gel filtration calibration kits (Amersham Biosciences, Piscataway, N.J.) in 50 mM sodium phosphate, 150 mM NaCl, pH 7.0 buffer. The marker proteins were thyroglobulin {molecular weight (Mw) 669 kDa}, ferritin (Mw 440 kDa), catalase (Mw 232 kDa), aldolase (Mw 158 kDa), albumin (Mw 67 kDa), ovalbumin (Mw 43 kDa), chymotrypsinogen A (,Mw 25 kDa), and ribonuclease A (Mw 13.7 kDa).

Bacterial pellets were suspended in 100 ml of ice-cold lysis buffer (20 mM phosphate buffer, pH 7.0 containing 50 mM Tris-HCl, pH 7.5 and 5 M NaCl). The uniform cell suspension was sonicated (Sonicator, Model W-385, Heat systems-Ultrasonics, Inc.) 4×15 sec bursts at minimum power-out put settings in ice with 2 min interval between each burst. The lysate was centrifuged at 10,000 g (Beckman #17 Rotor, 13,000 RPM) at 4° C. and the supernatant was applied onto a Sephacryl S-100 column (HiPrep 16×60) using AKTA FPLC system with Unicorn 3.1 software (Amersham Pharmacia Biotech) at a flow rate of 1 ml/min. Fractions (2-4 ml) were collected immediately after the void volume)($V_0$) (35 ml). Aliquots from each fraction were assayed by slot blotting, SDS-PAGE and western blotting. The strategy for employing slot blotting was to detect the desired fractions quickly (in less than 6 hrs) on large number of fractions so that any protein degradation is minimized by reducing the processing time. Once the positive fractions were identified by slot blots, we employed western blotting to confirm the molecular size of the desired protein.

Example 32

$Ni^{++}$-NTA Agarose Affinity Chromatography

The fractions from molecular exclusion chromatography, identified by western blots were pooled, dialyzed against 20 mM phosphate buffer, pH 7.5 containing Urea (8 M), NaCl (50 mM) and imidazole (20 mM) for metal-ion affinity selection. The dialyzed protein sample was applied to a 10 ml-$Ni^{++}$-nitrilotriacetic acid (NTA) agarose affinity resin (Probond, Invitrogen) previously equilibrated with 4×10 ml of buffer. Non-specific and low-affinity bound proteins were removed from the column with 3×10 ml of 20 mM phosphate buffer, pH 6.0 containing urea (8 M), NaCl (50 mM) and imidazole (20 mM). Affinity-bound proteins were eluted using 3×10 ml 20 mM phosphate buffer, pH 4.0 containing urea (8 M), NaCl (50 mM). The eluates were combined and concentrated using a centriprep YM 50 ultrafiltration device by spinning at 2000×g. Flow-thru, washes, and eluate were concentrated using a centriprep and analyzed by SDSPAGE and western blotting using rabbit polyclonal antibodies specific to the hemagglutinin fusion-tag.

Fractions containing desired proteins were pooled (based on western blot) and then concentrated, de-salted and buffer-exchanged using the centriprep devices (Amicon). Protein samples were stored at −70° C. Fractions containing unwanted contaminant proteins were discarded. Protein quantitation was performed with protein assay reagent (Bio-Rad) using BSA as the standard. The yield of recombinant protein was routinely about 0.5 to 1 mg of pure protein from every 2-liter culture.

Example 33

Fluorescent-Labeling of Recombinant Proteins

Labeling of purified proteins was performed following the standard protocol. Staros, J. V. (1988). Membrane-impermeant crosslinking reagents. Probes of the structure and dynamics of membrane proteins. Acc. Chem. Res. 21:435-441. Briefly, fluorescein isothiocyanate (FITC) was prepared fresh (1 mg/ml) in conjugation buffer (50 mM borate buffer, pH 8.0 containing 0.5 N NaCl). 20 ul of FITC solution was mixed with 100 ul of purified recombinant protein (0.1 mg/100 ul of conjugation buffer) and incubated for 1 h at 37° C. in the dark. Excess or hydrolyzed FITC was removed by gel filtration in a 5-ml desalting column. Labeled protein was buffer exchanged and/or concentrated to the original volume using a centricon device.

Example 34

Determination of the Efficacy of Cell Entry by TAT-Fusion Proteins

Rabbit peripheral blood (3 ml) was obtained by venipuncture and the buffy coat cells were isolated by centrifugation at 1200×g for 10 min. Minamide A, Boden S D, et al. (2003) Mechanism of bone formation with gene transfer of the cDNA encoding for the intracellular protein LMP-1. J Bone & Joint Surg Am. 85A:1030-1039. Buffy coat cells were counted and million cells were incubated with various concentrations of TAT-fusion proteins. Various concentrations (1.0, 2.5, 5.0, 10.0, and 25.0 nM) of the FITC labeled proteins were incubated for 15, 30 and 60 minutes with 1 million rabbit buffy coat cells. After the incubation, the cells were trypsinized and washed one time with PBS and resuspended in 500 ul of PBS. The percentage of the total cells labeled with FITC-specific fluorescence was determined by Flow Cytometry (Becton Dickinson, Franklin, N.J.).

Example 35

Cell Culture

MSCs at passage 2 were purchased from Cambrex Bio Sciences. Cells were grown at 37° C. in 5% $CO_2$ in MSC basal medium supplemented with Singlequots (Cambrex Bio Sciences), split at confluence, and plated at $3 \times 10^4$ cells/well in 6-well dishes at passage 4 in these studies. The next day treatments were applied in the presence of 50 uM L-Ascorbic Acid 2-Phosphate and 5 mM β-glycerol phosphate (Sigma-Aldrich).

Preparation of Nuclear and Cytoplasmic Protein Fractions.

Cell pellets were suspended in buffer A (20 mM HEPES, pH 7.9, 10 mM KCl, 1 mM EGTA, 1 mM EDTA, 0.2% Nonidet P-40, 10% Glycerol, 1 mM PMSF and 1 ug/ml protease inhibitor mix (Sigma)), incubated on ice for 10 min, and centrifuged. Supernatants (cytoplasmic fraction) were collected. Nuclear pellets were suspended in high salt buffer B (buffer A plus 600 mM KCl, 20% glycerol), incubated on ice for 30 min and centrifuged. Supernatants were collected as the nuclear fraction. Samples were aliquoted, the protein concentration determined, and stored at -70° C. until further use.

Example 36

SDS-PAGE and Western Blotting

SDS-PAGE was performed using 10% gels and transferred to nitrocellulose membrane. The membrane was blocked with milk protein, incubated with specific antibody, washed with Tris Buffered Saline containing 0.1% Tween 20 (TEST), incubated with anti-rabbit goat IgG-linked to horseradish peroxidase (NEN), and again washed with TBST. Chemiluminescent substrates were applied to the membrane and the signal was detected by exposing the membrane to X-ray film for 30 sec.

Example 37

$Ni^{++}$-NTA Agarose Affinity Pull-Down Assay

Nuclear proteins were prepared from mesenchymal stem cells as described above. TAT-LMP-1 (50 ug) was incubated for 1 hr at 4° C. with the nuclear proteins (500 ug) with gentle mixing in PBS containing 0.1 M NaCl and 50 mM imidazole. $Ni^{++}$-NTA-affinity beads (Probond, Invitrogen) (a 50 ul of 1:1 slurry in PBS) were added and the mixture was incubated for another 30 min. Non-specific proteins were removed by washing three times with 500 ul of PBS containing 0.1 M NaCl and 50 mM imidazole. Affinity bound proteins were eluted with 250 mM imidazole in PBS followed by a final elution with 50 mM EDTA removing the $Ni^{++}$ from the resin. The imidazole and EDTA eluates were analyzed by SDS-PAGE, staining of blots with colloidal gold stain to visualize total proteins, and western blots using HA-specific antibodies to detect input TAT protein.

Results of the Examples 26-37:

Construction of the expression plasmid with cDNAs for LMP-1, Dlx-5, Runx2, and Osterix.

The cloned cDNAs were transferred from pcDNA 3.1 vectors to the TAT-HA vector. In each case, the desired restriction sites were introduced by oligonucleotides and/or PCR followed by ligation in-frame into the linearized TAT-vector. A general cloning strategy followed for the construction of LMP-1 into TAT-HA vector is shown in FIG. 18.

Insertion of the desired cDNA in the correct coding frame in to the expression vector was confirmed by restriction digestions and sequencing of sense and anti-sense strands of DNA. The positive clones were selected based on the small scale induction of protein and the detection of correct molecular size bands in western blots performed with the HA tag-specific antibody.

Bacterial growth and expression of recombinant proteins.

Under the growth conditions used, none of the recombinant proteins were toxic to bacterial cells. No inclusion bodies which are frequently found with high level expression of proteins was encountered. The bacterial pellets that were stored frozen at -70° C., gave consistently better yield (up to approximately 15%) of soluble protein after cell lysis by ultrasonication than un-frozen pellets. The yields of purified protein for LMP-1, Dlx5, Runx2 and Osx, were 1.0, 0.5, 1.5 and 1.5 mg/L, respectively. All the expressed mammalian genes showed yields that were lower than expected and thus the procedure may warrant use of mammalian-'optimized codon hosts' for future purifications.

As the conditions of protein expression can have a profound effect on the stability of mammalian proteins in bacteria, optimization of expression conditions and strategies will probably further increase the successful expression and purification of mammalian proteins from bacteria. However, the recovered proteins in our current method were highly homogeneous and were sufficiently suitable for all the cell entry and pull down studies.

Purification of Recombinant Proteins.

The presence of hexahistidine tag in the recombinant protein allows use of $Ni^{++}$-affinity resins for purification of the desired protein. However, when the bacterial lysate was applied to $Ni^{++}$-affinity resins directly, the abundance of non-specific bacterial proteins competing with the desired protein for binding did not permit the effective use of the metal affinity resin. In addition, the high concentration of proteins in these samples (over 10 mg/ml) promoted non-specific aggregation and poor performance of the resin. To circumvent this problem, we chose to first perform molecular exclusion chromatography to select desired protein fractions based on molecular size. Addition of this step eliminated about 60-80% of the unwanted proteins before employing $Ni^{++}$-affinity selection of the desired protein.

Although all the chromatographic runs were performed at room temperature for short durations, the integrity of purified proteins was not affected. Fractionation of proteins by gel filtration prior to metal-affinity purification reduced the protein load on Ni$^{++}$-nitrilotriacetic acid (NTA) agarose columns and resulted in greatly improved purity of the proteins eluted from the affinity column. High salt concentrations in the buffers reduced or eliminated non-specific ionic interactions among the proteins, thereby enhancing the efficiency of purification. In addition, the high concentration of NaCl (5.0 N) prevented any weak ionic interaction of proteins with the Sephacryl-100 resin and prevented possible aggregation of proteins on column material. Aliquots (50 ul) of the protein fractions eluting from the column were taken for slot blot assay with antibodies specific for HA-tag epitope to detect the desired recombinant protein.

Figure 26:
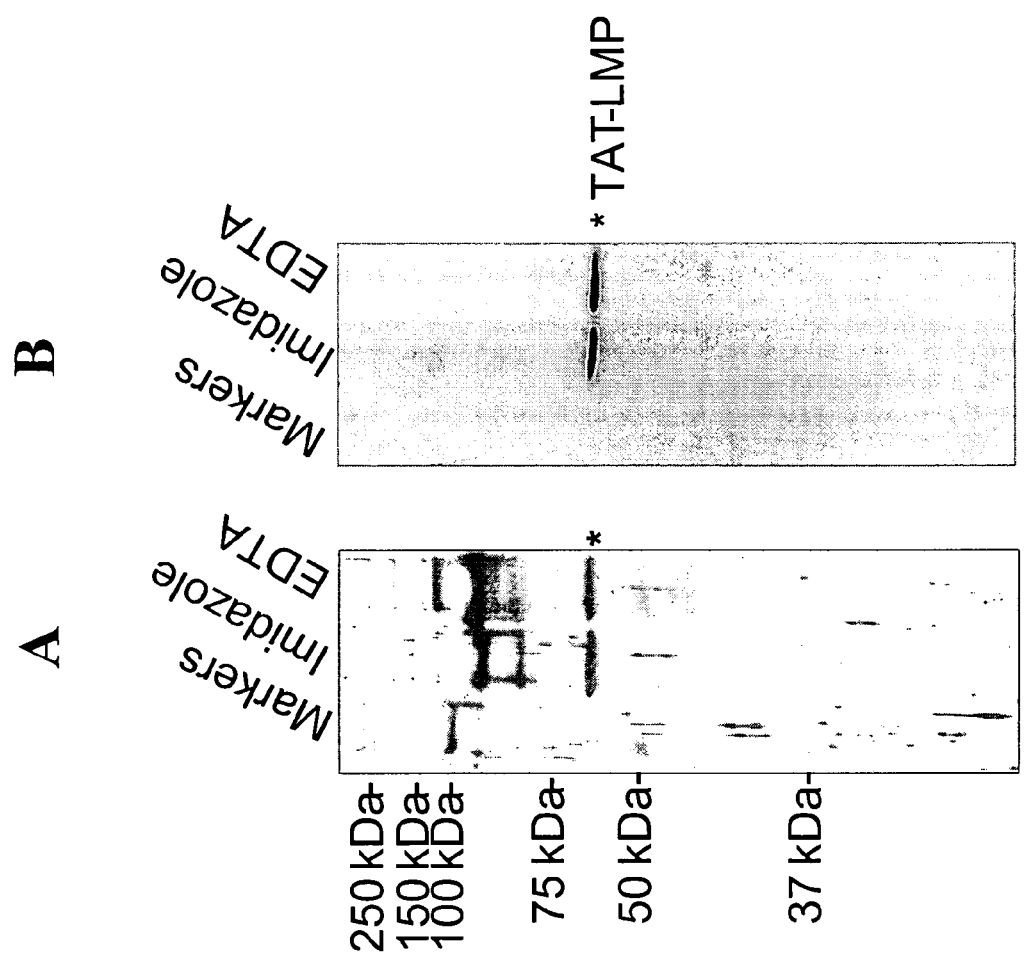
FIG. 26 shows TAT-LMP-1 associates with specific nuclear proteins. A Metal affinity tag pull-down assay was performed as described in methods. The bound proteins were eluted with 250 mM imidazole followed by removal of $Ni^{++}$ with 50 mM EDTA. Protein samples (5 ug) were resolved by SDS-PAGE, transblotted to nitrocellulose membrane. The blotted proteins were stained with colloidal gold for total protein (Panel A) or probed with HA-specific primary antibody followed by horse radish peroxidase (HRP)-labeled second antibody (Panel B). The signal was developed with enhanced chemi-luminescence as described in methods.

The use of slot blots, at this stage, improved efficiency and simplified detection of the desired protein in a large number of fractions from multiple chromatographic runs. Based on these slot blots, a fewer number of fractions that contained the desired protein were then subjected to SDS-PAGE and western blot analysis to confirm the expected molecular size for each protein. The indicated (FIGS. 19-22) fractions were pooled, concentrated and dialyzed for Ni$^{++}$-affinity purification. Ni$^{++}$-affinity selection was very effective and yielded highly homogeneous preparations for each protein (FIG. 26). The optimized two-step purification procedure was quick and, thus, minimizes the chance of oxidation of cysteine residues in the purified protein.

The SDS-PAGE gels and western blots of purified LMP-1, Dlx5, Runx2 and Osterix showed predominantly a single band. The molecular size for each protein corresponded to the expected size of the protein plus the fusion-tags (55, 37, 49, 53 kDa, respectively)(FIG. 26). The hexahistidine-TAT-HA tags contribute 5 kDa to the actual molecular weight of each protein but it may have different effects on the apparent size/shape of each fusion protein. The charged tag extends out and increases the apparent molecular size of the proteins. Premature termination of polypeptides was not observed to any significant degree for each of the expressed recombinant proteins as we did not co-purify significant amounts of truncated forms.

FITC Labeling and Flow Cytometry.

In pilot labeling experiments different ratios (protein:FITC) were used for each recombinant protein as the optimum labeling ratio is unique to each protein. The labeling index was determined for each ratio by calculating the FITC-to-protein molar ratio for optimal labeling by measuring the maximal absorbance of all four proteins (LMP-1, Dlx5, Runx2 and Osx) at wavelengths of 280 and 495 nm, respectively. The specific activity of incorporation was normalized for each protein based on these readings. The optimum labeling indices were 35% for the 10:1 FITC:protein ratio.

The labeled proteins were all effectively separated from free FITC by gel filtration, resulting in little or no background of free label. Rabbit buffy coat cells were incubated with various doses of TAT-fusion protein (1-25 nM) for different durations. The primary reasons for using buffy coat cells are that they are relatively easy to separate and high number of cells can be readily obtained from the blood of human volunteers. To determine the efficacy of TAT-mediated cellular entry of recombinant proteins the rabbit buffy coat cells were extensively washed to remove the excess TAT-protein and analyzed by flow cytometry. This design allows one of ordinary skill in the art to monitor the dose dependent response for each FITC labeled protein. The highest dose tested (25 nM) showed maximum entry (78%) after 30 min incubation.

Figure 24:
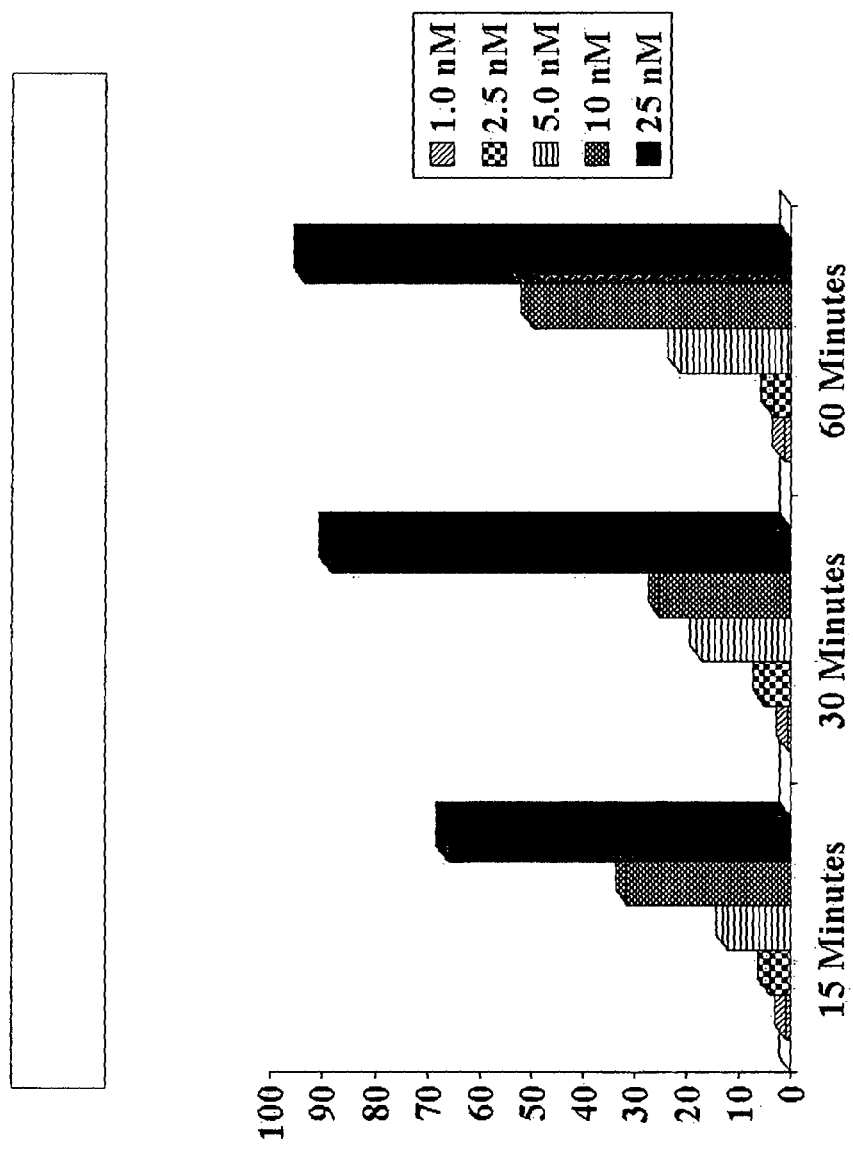
FIG. 24 is a time and Dose-dependent accumulation of FITC labeled TAT-LMP-1 into rabbit buffy coat cells. TAT-LMP-1 was labeled with FITC and incubated with rabbit buffy coat cells. Concentrations ranging from 1.0 to 25 nM of FITC-labeled TAT-LMP-1 was incubated for 15, 30 and 60 min at 37° C. with $10^6$ cells. After washes the % of total cells containing FITC was determined by flow cytometry.

At doses lower than 5 nM, we observed protein entry into less than 1.0% of the cells after 30 min incubation. FIG. 24 shows that TAT-LMP-1-FITC entry into rabbit buffy coat cells is both time and dose dependent. The FITC-labeled Runx2, Osx and Dlx5 also showed time and dose dependent entry into cells (data not shown). The limitation of the flow cytometry method is that it does not distinguish intracellular TAT-protein from TAT-protein adsorbed to the cell surface.

To address this issue, one must reactionate both cytoplasmic and nuclear extracts and determined the presence of TAT-protein in each extract by western blots using HA-specific antibodies.

Detection of TAT-proteins in nuclear and cytoplasmic fractions.

According to this aspect of the invention, the inventors focused on the cellular entry and the intracellular protein interactions of TAT-LMP-1. Mesenchymal stem cells were incubated with various concentrations of TAT-LMP-1 (0.3-300 nM). The cells were harvested after 4 hr and the cytoplasmic and nuclear extracts were prepared as mentioned in methods. Equal aliquots (as determined by protein amounts) of these preparations were subjected to SDS-PAGE. The resolved proteins were blotted onto nitrocellulose and probed with HA-antibody in western blots.

Figure 25:
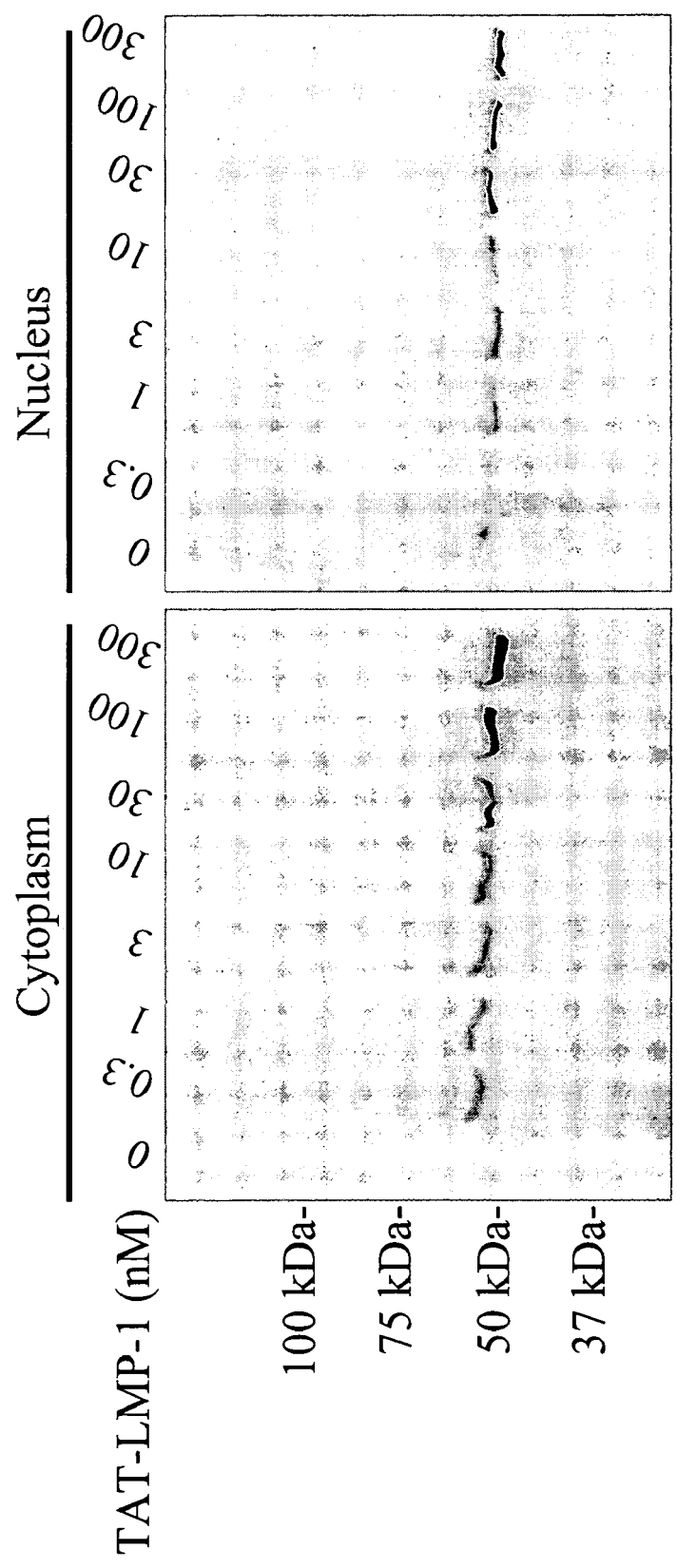
FIG. 25 shows that a TAT-fusion protein was detected in both nuclear and cytoplasmic fractions in MSCs. Equal aliquots of protein (10 ug) were loaded in each lane. The cytoplasmic and nuclear lanes contained samples obtained from cells that were treated with 0.3 to 300 nM TAT-LMP-1. The blots were blocked and probed with rabbit HA-specific antibodies. The signal is detected by HRP-labeled anti-rabbit second antibodies and enhanced chemi-luminescence.

One of ordinary skill in the art can appreciate that a dose dependent increase of TAT-LMP-1 at the expected size (55 kDa) is observed in both cytoplasmic and nuclear fractions when compared to untreated controls (FIG. 25). The higher intensity of the signal observed in cytoplasmic fractions may be due to a higher concentration of TAT-protein in the cytoplasm. The control lanes showed little or no signal confirming that the observed signal is specific to exogenously added TAT-protein. This data also suggested that exogenously added TAT-protein is relatively resistant to cellular proteases and is easily detectable with HA-antibodies in both cytoplasmic and nuclear compartments.

In these western blots, inventors chose HA-antibodies so that they could distinguish the exogenously added protein from the cellular endogenous proteins. The TAT-protein accumulated in both the compartments suggesting that the TAT-domain is capable of transducing through all cellular membranes as suggested in the literature. Inventors were then determined that significant amounts of the excess TAT-protein was present in cell culture supernants.

Detection of Nuclear Proteins in MSCs that Associate with TAT-LMP-1

One defining feature of eukaryotic cells is their spatial and functional division into the nucleus and the cytoplasm by the nuclear envelope. Each of the nuclear osteogenic factors, LMP-1, Dlx5, Runx2 or Osterix, has been postulated to function in a signaling network involving a large number of interacting proteins. The aim of this study was to optimize methods to perform the controlled delivery of these signaling molecules either to promote or disrupt protein interaction events in nuclear compartment resulting in the control of cellular differentiation.

As a pilot study, one of ordinary skill in the art would appreciate that the inventors used TAT-LMP-1 as molecular bait to detect any MSC nuclear proteins with which it interacts. The inventors also observed a large number of proteins binding TAT-LMP-1 with high affinity (FIG. 26). Proteins of molecular size 80 to 90 kDa showed predominant colloidal gold staining suggesting that proteins in this zone are the most likely binding candidates for LMP-1 interaction. Based on these results one of ordinary skill in the art may slightly alter the currently disclosed experimental approach and performed photo-induced biotin transfer experiments to identify target nuclear molecules that interact with TAT-LMP-1.

Example 38

The Synthesis of pHIS-5' ATG LMP-1s Expression Vector from the Sequences Demonstrated in Examples 2 and 3

The 717 base-pair clone (Example 17) was digested with ClaI and EcoRV (New England Biologicals, city, MA). A small fragment (~250 base pairs) was gel purified. Clone No. 7 (Example 18) was digested with ClaI and XbaI. A 1400 base-pair fragment was gel purified from that digest. The isolated 250 base-pair and 1400 base-pair cDNA fragments were ligated by standard methods to form a fragment of ~1650 bp. The pHis-A vector (InVitrogen) was digested with EcoRV and XbaI. The linearized vector was recovered and ligated to the chimeric 1650 base-pair cDNA fragment. The ligated product was cloned and amplified by standard methods, and the pHis-A-5' ATG LMP-1s expression vector, also denominated as the vector pHis-A with insert HLMP-1s, was deposited at the ATCC as previously described.

Example 39

The Induction of Bone Nodule Formation and Mineralization In Vitro with pHis-5' ATG LMP-1s Expression Vector Rat calvarial cells were isolated and grown in secondary culture according to Example 1. Cultures were either unstimulated or stimulated with glucocorticoid (GC) according to Example 1. The cultures were transfected with 3 μg of recombinant pHis-A vector DNA/well as described in Example 25. Mineralized nodules were visualized by Von Kossa staining according to Example 3.

Human LMP-1s gene product overexpression alone (i.e., without GC stimulation) induced significant bone nodule formation (~203 nodules/well) in vitro. This is approximately 50% of the amount of nodules produced by cells exposed to the GC positive control (~412 nodules/well). Similar results were obtained with cultures transfected with pHisA-LMP-Rat Expression vector (~152 nodules/well) and pCMV2/LMP-Rat-Fwd (~206 nodules/well). In contrast, the negative control pCMV2/LMP-Rat-Rev yielded (~2 nodules/well), while approximately 4 nodules/well were seen in the untreated plates. These data demonstrate that the human LMP-1 cDNA was at least as osteoinductive as the rat LMP-1 cDNA in this model system. The effect in this experiment was less than that observed with GC stimulation; but in some the effect was comparable.

Example 40

LMP Induces Secretion of a Soluble Osteoinductive Factor

Overexpression of RLMP-1 or HLMP-1s in rat calvarial osteoblast cultures as described in Example 24 resulted in significantly greater nodule formation than was observed in the negative control. To study the mechanism of action of LIM mineralization protein conditioned medium was harvested at different time points, concentrated to 10×, sterile filtered, diluted to its original concentration in medium containing fresh serum, and applied for four days to untransfected cells.

Conditioned media harvested from cells transfected with RLMP-1 or HLMP-1s at day 4 was approximately as effective in inducing nodule formation as direct overexpression of RLMP-1 in transfected cells. Conditioned media from cells transfected with RLMP-1 or HLMP-1 in the reverse orientation had no apparent effect on nodule formation. Nor did conditioned media harvested from LMP-1 transfected cultures before day 4 induce nodule formation. These data suggest that expression of LMP-1 caused the synthesis and/or secretion of a soluble factor, which did not appear in culture medium in effective amounts until 4 days post transfection.

Since overexpression of rLMP-1 resulted in the secretion of an osteoinductive factor into the medium, Western blot analysis was used to determine if LMP-1 protein was present in the medium. The presence of RLMP-1 protein was assessed using antibody specific for LMP-1 (QDPDEE) and detected by conventional means. LMP-1 protein was found only in the cell layer of the culture and not detected in the medium.

Partial purification of the osteoinductive soluble factor was accomplished by standard 25% and 100% ammonium sulfate cuts followed by DE-52 anion exchange batch chromatography (100 mM or 500 mM NACl). All activity was observed in the high ammonium sulfate, high NaCl fractions. Such localization is consistent with the possibility of a single factor being responsible for conditioning the medium.

Example 41

Transfection of A-549 Cells

The restriction and modifying enzymes used in examples 41-50 were purchased from Promega (Madison, Wis.). The chelating affinity resin (Probond) and the pHisA vector were purchased from Invitrogen (San Diego, Calif.). The Sephacryl S-300 (HiPrep 16×60), other chromatographic columns and the AKTA FPLC system were from Amersham-Pharmacia Biotech (Piscataway, N.J.). All other chemicals and reagents, unless otherwise noted, were from Sigma (St. Louis, Mo.) (analytical grade). *Escherichia coli* DH5alpha cells was the host for propagation of plasmids. DH5alpha cells were maintained on LB agar plates and grown at 37° C. in the presence of ampicillin (100 mg/mL). The strains were maintained in LB medium including 15% glycerol at −80° C.

A-549 cells were grown in F12K medium (Gibco, Grand Island, N.Y.) in a humidified 10% $CO_2$ incubator at 37° C. supplemented with 10% non-heat-inactivated fetal bovine serum (Atlanta Biologicals, Norcross, Ga.). The 1623-bp cDNA for LMP-1 was cloned into the mammalian expression vector pHisA/pcDNA 3.1 following standard methods. The over-expressed LMP-1 contains a 6His-fusion tag at the N-terminus to facilitate affinity purification. The plasmid construct (10 ug/100 mm plate) was incubated for 2 h with A-549 cells using 60 ul of Superfect (Qiagen, Valencia, Calif.) per plate in 10 ml medium and the cultures were incubated for 2 days. Cells from 50×100 mm plates were harvested with phosphate-buffered saline by scraping with rubber policemen.

Example 42

Preparation of Nuclear and Cytoplasmic Protein Fractions from A-549 Cells

The A-549 cell pellets were resuspended in low salt buffer (20 mM HEPES, pH 7.9, 10 mM KCl, 1 mM EGTA, 1 mM EDTA, 0.2% Nonidet P-40, 10% Glycerol, 1 mM phenylmethylsulfonyl fluoride and 1 ug/ml of protease inhibitor mix (Sigma), incubated on ice for 10 min, and centrifuged (8000× g, 2 min, 4° C.). Supernatants (cytoplasmic fraction) were collected for further analysis. The nuclear pellets were suspended in high salt buffer (low salt buffer with 600 mM KCl, 20% glycerol), incubated on ice for 30 min and centrifuged as before. Supernatants were collected as the nuclear fraction. Both cytoplasmic and nuclear fractions were aloquted and stored frozen at −20° C. until further use.

Example 43

Purification of Recombinant LMP-1 from Cellular Extracts

Size-exclusion chromatography of the cellular proteins was carried out on a Sephacryl S-300 column connected to the AKTA FPLC System (Amersham Biosciences, Piscataway, N.J.). The column was pre-calibrated with known low- and high-molecular weight protein markers from gel filtration calibration kits (Amersham Biosciences, Piscataway, N.J.) in 50 mM sodium phosphate, 150 mM NaCl, pH 7.0 buffer. The marker proteins were thyroglobulin (molecular weight (Mw) 669 kDa), ferritin (Mw 440 kDa), catalase (Mw 232 kDa), aldolase (Mw 158 kDa), albumin (Mw 67 kDa), ovalbumin (Mw 43 kDa), chymotrypsinogen A (,Mw 25 kDa), and ribonuclease A (Mw 13.7 kDa).

The cell pellets were suspended in 100 ml of ice-cold lysis buffer (20 mM phosphate buffer, pH 7.0 containing 50 mM Tris-HCl, pH 7.5 and 5 M NaCl). The uniform cell suspension was centrifuged at 10,000 g (Beckman #17 Rotor, 13,000 RPM) at 4° C. and the supernatant was applied onto a Sephacryl S-300 column (HiPrep 16×60) using AKTA FPLC system with Unicorn 3.1 software (Amersham Pharmacia Biotech) at a flow rate of 1 ml/min. Fractions (4 ml) were collected immediately after the void volume ($V_o$) (35 ml).

The proteins were applied onto $Ni^{++}$-affinity column (5 ml resin) previously equilibrated with 4×5 ml of buffer. Non-specific and low-affinity proteins were washed off the column with 3×10 ml of 20 mM phosphate buffer, pH 6.0 containing urea (8 M), NaCl (50 mM) and imidazole (20 mM). Affinity-bound proteins were eluted using 3×10 ml washes with 20 mM phosphate buffer, pH 4.0 containing urea (8 M), NaCl (50 mM). The eluates were combined and concentrated by spinning at 2000 g using a centriprep YM 50 ultrafiltration device. Flow-thru, washes and eluate were concentrated using a centriprep device and analysed by SDS-PAGE and western blotting. LMP-1 antibodies raised in rabbit for the peptide epitope from the osteogenic region of LMP-1: ADPPRYTFAPS-VSLNKTARPFGAPPP (the unique central region of LMP-1) (SEQ ID NO: 43) were used for western blotting. Affinity eluted fractions were dialyzed against 20 mM Tris-HCl pH 7.5 (Buffer A) over night at 4° C. using a 10 kDa cut-off membrane for cation-exchange chromatography.

A HiTrap SP Sepharose (FF) cation exchange column, 1 ml (Pharmacia) was equilibrated in buffer A. Protein sample was syringe filtered using a 0.2u membrane and applied onto the column in buffer A. The bound proteins were eluted using the AKTA-FPLC system (Amersham-Pharmacia Biotech) by generating a linear gradient of NaCl from 0 to 1.0 M over 20 min at a flow rate of 1 ml/min. Finally the column was washed with 20% ethanol and stored until further use at 4° C. Fractions (1 ml) were diluted 3-fold (5 ul of sample plus 10 ul of water to reduce the salt concentration) and analysed by SDS-PAGE followed by western blotting using specific primary antibodies and horse radish peroxidase labeled secondary antibodies. Fractions containing recombinant protein (based on western blot) were pooled, concentrated and de-salted using the centriprep devices (Amicon). Protein samples were stored at −70° C., until further use, at this stage. Fractions containing unwanted contaminant proteins were discarded.

Protein quantitation was performed with protein assay reagent (BioRad) using BSA as standard. Due to poor dye binding by LMP-1 (abundance of Pro, Gly, Ser and Cys residues), more accurate protein amounts were determined from the overall yield of peptides from trypsin digestion and mass spectrometric analysis. The collective yield of the recombinant LMP-1 protein was about 75-100 ug from 120× 100 mm cell culture plates from three batches of 40 plates each).

Example 44

SDS-PAGE and Western Blotting

SDS-PAGE is performed using 10% gels according to Laemmli et al and the electrophoresed proteins were transferred from the gel to a nitrocellulose membrane at 50 volts (constant) for 2 hrs. The membranes were blocked with 25 ml 5% milk protein for 1 hour at room temperature. Membranes were incubated with LMP-1 antibody at a dilution of 1:5000 (5 ul/25 ml of Tris-buffered saline containing 0.1% Tween 20) gently shaking for 2 hours at room temperature. Membranes were washed with 25 ml of TBST for 5 min. The washes were repeated two times. Membranes were incubated with anti-rabbit goat IgG-linked to horse radish peroxidase (NEF 812, NEN, Boston) diluted 1:5000 in 25 ml TBST for 1 hour. Membranes were washed three times, 5-min each with 25 ml of TBST as before. Chemiluminescent substrate reagent A (2 ml) and reagent B (2 ml) were mixed and applied to the membrane. The damp-dried membrane was exposed to X-ray film for signal detection.

Example 45

Sugar Composition Analysis

Sugar compositions were determined as described previously (Yasuno, S., Murata) (Sangadala et al 2001). Briefly, the purified protein (100 µg) was dissolved in 20 µl distilled water in a test tube to which 4 M TFA (20 µl, for neutral sugars) or 8 M HCl (20 µl, for amino sugars) was added. The test tube was incubated at 100° C. in a hot block bath. After 4 hr (neutral sugars) or 6 hr (amino sugars), the tube was cooled to room temperature and the acid was removed by using a centrifugal concentrator at 35° C. The dried sample was derivatized with ABEE in the presence of borane-pyridine complex at 80° C. After 1 hr, the reaction mixture was cooled to room temperature. Distilled water (200 µl) and an equal volume of chloroform were added to the reaction mixture. After vigorous vortexing, the sample was centrifuged (6000×g, 1 min). The upper aqueous layer was analyzed by reversed-phase HPLC under the following conditions: column, Wakosil-II 5C18HG (4.6×150 mm); solvent, A 0.02% TFA/$CH_3CN$ (90/10), B 0.02% TFA/$CH_3CN$ (50/50); program, 0-45 min (B conc. 0%), 45-55 min (B conc. 100%), 55-70 min (B conc. 0%); flow rate, 1 ml/min; temp., 45° C.; detection, absorbance at 305 nm. The monosaccharide and amino monosaccharide standards used were N-acetyl glucosamine, N-acetyl galactosamine, glucose, galactose, mannose, xylose, and L-fucose.

Example 46

In-Gel Digestion of LMP-1 by Trypsin

SDS-PAGE gels were stained with 0.25% Coomassie brilliant blue in 45% methanol and 10% acetic acid and destained in 35% methanol with 10% acetic acid. The protein bands corresponding to a positive signal on western blots were sliced from the gel, soaked in 50% methanol with 0.1 M $NH_4HCO_3$ and mixed vigorously overnight. The wash solution was changed once and incubated for 2 hr. The clear gel bands were then soaked in water for 2 hr followed by soaking in 25 mM $NH_4HCO_3$ for 5 min. The wet gel pieces were smashed into fine pieces in Eppendorf tubes (0.5 ml). Trypsin (Promega) digestion was performed in 25 mM $NH_4HCO_3$ (pH 8.0) overnight at 37° C. Following digestion, peptides were extracted twice with acetonitrile and aliquots were lyophilyzed. (Bernardo et al, Wilkins et al, Winters et al).

Example 47

Preparation of Peptide Samples for Mass Spectrometry Analysis

Peptide samples were purified and concentrated using a Zip Tip (Millipore) which has $C_{18}$ resin fixed at its end. The resin was rinsed according to the manufacturer's instructions with 10 µl of 0.1% trifluoroacetic acid (TFA) and 50% acetonitrile (ACN). Peptides were eluted in 10 µl 1:1 ACN-0.1% TFA. A 0.5 µl volume of the concentrated peptide-containing sample was mixed with 0.5 µl of a saturated solution of α-cyano-4-hydroxycinnamic acid. Each sample (0.5 ul) was spotted on the mass spectrometer sample plate (Tremoulet et al).

Example 48

Separation of Peptides by HPLC

After trypsin digestion, the mixture (85%) of LMP-1 peptides were separated by capillary reversed-phase HPLC using the method described before [Hubalek, F., Edmondson]. The peptide fragments were separated by small bore reverse phase HPLC on a Vydac $C_{18}$ column (4.6×250 mm) using a gradient HPLC system (Waters). The chromatographic run was performed with an aqueous phase containing 0.1% trifluoroacetic acid and organic phase containing 0.085% trifluoroacetic acid in acetonitrile with a flow rate of 0.5 ml/min. The gradient used for separation was 2-60% of acetonitrile for 40 min; the total run time was 60 min. The collected peptides were subjected to internal fragment N-terminal sequence analysis by standard Edman degradation (Procise 494 HT protein sequencer, Applied Biosystems, Foster City, Calif.). The eluate absorbing at 210 nm was manually collected for sequence analysis.

Example 49

Protein Identification and Amino Acid Sequence Analysis

In order to increase sequence coverage of LMP-1, aliquots of HPLC fractions of the digest also were analyzed by MALDITOF/TOF MS/MS using a model 4700 Proteomics Analyzer (Applied Biosystems). For each fraction, an MS spectrum was initially collected. For post source decay analysis, the HPLC-purified peptide was subjected to ion generation by post-source decay (Chaurand P 1999). A matrix-assisted laser desorption ionization-post-source decay (MALDI-PSD) time-of-flight spectrum was recorded using alpha-cyano-4-hydroxy cinnamic acid as a matrix; acquisition was at 27.5 kV under continuous extraction conditions; reflector voltage was stepped from 30 to 1.27 kV, and the spectrum was constructed using the FAST™ method from Bruker-Daltonic (Bremen, Germany). Using the manufacturer's GPS Explorer 2.0 software, the MS and MS/MS data were submitted to a MASCOT search engine (www.matrix-science.com) for positive identification. The NCBI non-redundant database and the Mammalia taxonomy were used for these and all other searches.

Example 50

Database Searches for Protein Identification

Monoisotopic peptide masses obtained from mass spectra were searched against the SWISS-PROT, NCBInr and MSDB databases using the MASCOT search program. The following parameters were used in the searches: mammalian, human, MS/MS Ion Search, protein mass of 50 kDa, trypsin digest with two missed cleavages, fragment ion mass tolerance of ±75 ppm and possible oxidation of methionine. The resulting protein hits were scored using a probability based Mowse score. The score is $-10*Log (P)$, where P is the probability that the observed match is a random event.

Example 51

Gene Therapy in Lumbar Spine Fusion Mediated by Low Dose Adenovirus

This study determined the optimal dose of adenoviral delivery of the LMP-1 cDNA (SEQ. ID NO: 2) to promote spine fusion in normal, that is, immune competent, rabbits.

A replication-deficient human recombinant adenovirus was constructed with the LMP-1 cDNA (SEQ. ID NO: 2) driven by a CMV promoter using the Adeno-Quest™. Kit (Quantum Biotechnologies, Inc., Montreal). A commercially available (Quantum Biotechnologies, Inc., Montreal) recombinant adenovirus containing the beta-galactosidase gene was used as a control.

Initially, an in vitro dose response experiment was performed to determine the optimal concentration of adenovirus-delivered LMP-1 ("AdV-LMP-1") to induce bone differentiation in rat calvarial osteoblast cultures using a 60-minute transduction with a multiplicity of infection ("MOI") of 0.025, 0.25, 2.5, or plaque-forming units (pfu) of virus per cell. Positive control cultures were differentiated by a 7-day exposure to $10^9$ M glucocorticoid ("GC"). Negative control cultures were left untreated. On day 14, the number of mineralized bone nodules was counted after von Kossa staining of the cultures, and the level of osteocalcin secreted into the medium (pmol/mL) was measured by radioimmunoassay (mean±SEM).

The results of this experiment are shown in Table 1. Essentially no spontaneous nodules formed in the untreated negative control cultures. The data show that a MOI equal to 0.25 pfu/cell is most effective for osteoinducing bone nodules, achieving a level comparable to the positive control (GC). Lower and higher doses of adenovirus were less effective.

TABLE 1

| Outcome | Neg Ctrl. | GC | Adv-LMP-Dose (MOI) 0.025 | 0.25 | 2.5 | 25 |
|---|---|---|---|---|---|---|
| Bone Nodules | 0.5 ± 0.2 | 188 ± 35 | 79.8 ± 13 | 145.1 ± 13 | 26.4 ± 15 | 87.6 ± 2 |
| Osteoclacin | 1.0 ± 0.1 | 57.8 ± 9 | 28.6 ± 11 | 22.8 ± 1 | 18.3 ± 3 | 26.0 ± 2 |

In vivo experiments were then performed to determine if the optimal in vitro dose was capable of promoting intertransverse process spine fusions in skeletally mature New Zealand white rabbits. Nine rabbits were anesthetized and 3 cc of bone marrow was aspirated from the distal femur through the intercondylar notch using an 18 gauge needle. The buffy coat was then isolated, a 10-minute transduction with AdV-LMP-1 was performed, and the cells were returned to the operating room for implantation. Single level posterolateral lumbar spine arthrodesis was performed with decortication of transverse processes and insertion of carrier (either rabbit devitalized bone matrix or a collagen sponge) containing 8-15 million autologous nucleated buffy coat cells transduced with either AdV-LMP-1 (MOI=0.4) or AdV-BGal (MOI=0.4). Rabbits were euthanized after 5 weeks and spine fusions were assessed by manual palpation, plain x-rays, CT scans, and undecalcified histology.

The spine fusion sites that received AdV-LMP-1 induced solid, continuous spine fusion masses in all nine rabbits. In contrast, the sites receiving AdV-BGal, or a lower dose of AdV-LMP-1 (MOI=0.04) made little or no bone and resulted in spine fusion at a rate comparable to the carrier alone (<40%). These results were consistent as evaluated by manual palpation, CT scan, and histology. Plain radiographs, however, sometimes overestimated the amount of bone that was present, especially in the control sites. LMP-1 cDNA delivery and bone induction was successful with both of the carrier materials tested. There was no evidence of systemic or local immune response to the adenovirus vector.

These data demonstrate consistent bone induction in a previously validated rabbit spine fusion model which is quite challenging. Furthermore, the protocol of using autogenous bone marrow cells with intraoperative ex vivo gene transduction (10 minutes) is a more clinically feasible procedure than other methods that call for overnight transduction or cell expansion for weeks in culture. In addition, the most effective dose of recombinant adenovirus (MOI=0.25) was substantially lower than doses reported in other gene therapy applications (MOI 40-500). We believe this is due to the fact that LMP-1 is an intracellular signaling molecule and may have powerful signal amplification cascades. Moreover, the observation that the same concentration of AdV-LMP-1 that induced bone in cell culture was effective in vivo was also surprising given the usual required increase in dose of other growth factors when translating from cell culture to animal experiments. Taken together, these observations indicate that local gene therapy using adenovirus to deliver the LMP-1 cDNA is possible and the low dose required will likely minimize the negative effects of immune response to the adenovirus vector.

Example 52

Use of Peripheral Venous Blood Nucleated Cells (Buffy Coat) for Gene Therapy with LMP-1 cDNA to Make Bone In four rabbits we performed spine fusion surgery as above (Example 38) except the transduced cells were the buffy coat from venous blood rather than bone marrow. These cells were transfected with Adeno-LMP or pHIS-LMP plasmid and had equivalent successful results as when bone marrow cells were used. This discovery of using ordinary venous blood cells for gene delivery makes gene therapy more feasible clinically since it avoids painful marrow harvest under general anesthesia and yields two times more cells per mL of starting material.

Example 53

Isolation of Human LMP-1 Splice Variants

Intron/Exon mRNA transcript splice variants are a relatively common regulatory mechanism in signal-transduction and cellular/tissue development. Splice variants of various genes have been shown to alter protein-protein, protein-DNA, protein-RNA, and protein-substrate interactions. Splice variants may also control tissue specificity for gene expression allowing different forms (and therefore functions) to be expressed in various tissues. Splice variants are a common regulatory phenomenon in cells. It is possible that the LMP splice variants may result in effects in other tissues such as nerve regeneration, muscle regeneration, or development of other tissues.

To screen a human heart cDNA library for splice variants of the HLMP-1 sequence, a pair of PCR primer corresponding to sections of SEQ. ID NO: 22 was prepared. The forward PCR primer, which was synthesized using standard techniques, corresponds to nucleotides 35-54 of SEQ. ID NO: 22. It has the following sequence:

5' GAGCCGGCATCATGGATTCC 3' (SEQ. ID NO: 35)

The reverse PCR primer, which is the reverse complement of nucleotides 820-839 in SEQ. ID NO: 22, has the following sequence:

5' GCTGCCTGCACAATGGAGGT 3' (SEQ. ID NO: 36)

The forward and reverse PCR primers were used to screen human heart cDNA (ClonTech, Cat No. 7404-1) for sequences similar to HLMP-1 by standard techniques, using a cycling protocol of 94° C. for 30 seconds, 64° C. for 30 seconds, and 72° C. for 1 minute, repeated 30 times and followed by a 10 minute incubation at 72° C. The amplification cDNA sequences were gel-purified and submitted to the Emory DNA Sequence Core Facility for sequencing. The clones were sequenced using standard techniques and the sequences were examined with PCGENE (intelligenetics; Programs SEQUIN and NALIGN) to determine homology to SEQ. ID NO: 22. Two homologous nucleotide sequences with putative alternative splice sites compared to SEQ. ID NO: were then translated to their respective protein products with Intelligenetic's program TRANSL.

One of these two novel human cDNA sequences (SEQ. ID NO: 37) comprises 1456 bp:

```
CGACGCAGAG CAGCGCCCTG GCCGGGCCAA GCAGGAGCCG GCATCATGGA TTCCTTCAAG    60
GTAGTGCTGG AGGGGCCAGC ACCTTGGGGC TTCCGGCTGC AAGGGGGCAA GGACTTCAAT   120
GPGCCCCTCT CCATTTCCCG GCTCACTCCT GGGGGCAAAG CGGCGCAGGC CGGAGTGGCC   180
GTGGGTGACT GGGTGCTGAG CATCGATGGC GAGAATCCGG GTAGCCTCAC ACACATCGAA   240
GCTCAGAACA AGATCCGGGC CTGCGGGGAG CGCCTCAGCC TGGGCCTCAG CAGGGCCCAG   300
                                x                  x
CCGGTTCAGA GCAAACCGCA GAAGGTGCAG ACCCCTGACA AACAGCCGCT CCGACCGCTG   360
GTCCCAGATG CCAGCAAGCA GCGGCTGATG GAGAACACAG AGGACTGGCG GCCGCGGCCG   420
GGGACAGGCC AGTCGCGTTC CTTCCGCATC CTTGCCCACC TCACAGGCAC CGAGTTCATG   480
CAAGACCCGG ATGAGGAGCA CCTGAAGAAA TCAAGCCAGG TGCCCAGGAC AGAAGCCCCA   540
GCCCCAGCCT CATCTACACC CCAGGAGCCC TGGCCTGGCC CTACCGCCCC CAGCCCTACC   600
AGCCGCCCGC CCTGGGCTGT GGACCCTGCG TTTGCCGAGC GCTATGCCCC GGACAAAACG   660
AGCACAGTGC TGACCCGGCA CAGCCAGCCG GCCACGCCCA CGCCGCTGCA GAGCCGCACC   720
TCCATTGTGC AGGCAGCTGC CGGAGGGGTG CCAGGAGGGG GCAGCAACAA CGGCAAGACT   780
CCCGTGTGTC ACCAGTGCCA CAAGGTCATC CGGGGCCGCT ACCTGGTGGC GTTGGGCCAC   840
GCGTACCACC CGGAGGAGTT TGTGTGTAGC CAGTGTGGGA AGGTCCTGGA AGAGGGTGGC   900
TTCTTTGAGG AGAAGGGCGC CATCTTCTGC CCACCATGCT ATGACGTGCG CTATGCACCC   960
AGCTGTGCCA AGTGCAAGAA GAAGATTACA GGCGAGATCA TGCACGCCCT GAAGATGACC  1020
TGGCACGTGC ACTGCTTTAC CTGTGCTGCC TGCAAGACGC CCATCCGGAA CAGGGCCTTC  1080
TACATGGAGG AGGGCGTGCC CTATTGCGAG CGAGACTATC AGAAGATGTT TGGCACGAAA  1140
TGCCATGGCT GTGACTTCAA GATCGACGCT GGGGACCGCT TCCTGGAGGC CCTGGGCTTC  1200
AGCTGGCATG ACACCTGCTT CGTCTGTGCG ATATGTCAGA TCAACCTGGA AGGAAAGACC  1260
TTCTACTCCA AGAAGGACAG GCCTCTCTGC AAGAGCCATC CCTTCTCTCA TGTGTGAGCC  1320
CCTTCTGCCC ACAGCTCCCG CGGTGGCCCC TAGCCTGAGG GGCCTGGAGT CGTGGCCCTG  1380
CATTTCTGGG TAGGGCTGGC AATGGTTGCC TTAACCCTGG CTCCTGGCCC GAGCCTGGGC  1440
TCCCGGGCCC TGCCCA                                                 1456
```

Reading frame shifts caused by the deletion of a 119 by fragment (between X) and the addition of a 17 by fragment (underlined) results in a truncated gene product having the following derived amino acid sequence (SEQ. ID NO: 38):

```
Met Asp Ser Phe Lys Val Val Leu Glu Gly Pro Ala Pro Trp Gly Phe
 1               5                  10                  15
Arg Leu Gln Gly Gly Lys Asp Phe Asn Val Pro Leu Ser Ile Ser Arg
                20                  25                  30
Leu Thr Pro Gly Gly Lys Ala Ala Gln Ala Gly Val Ala Val Gly Asp
                35                  40                  45
Trp Val Leu Ser Ile Asp Gly Glu Asn Ala Gly Ser Leu Thr His Ile
                50                  55                  60
Glu Ala Gln Asn Lys Tie Arg Ala Cys Gly Glu Arg Leu Ser Leu Gly
65                  70                  75                  80
Leu Ser Arg Ala Gln Pro Val Gln Asn Lys Pro Gln Lys Val Gln Thr
                85                  90                  95
Pro Asp Lys Gln Pro Leu Arq Pro Leu Val Pro Asp Ala Ser Lys Gln
                100                 105                 110
Arg Leu Met Glu Asn Thr Glu Asp Trp Arg Pro Arg Pro Gly Thr Gly
                115                 120                 125
```

-continued

```
Gln Ser Arg Ser Phe Arg Ile Leu Ala His Leu Thr Gly Thr Glu Phe
    130                 135                 140
Met Gln Asp Pro Asp Glu Glu His Leu Lys Lys Ser Ser Gln Val Pro
145                 150                 155                 160
Arg Thr Glu Ala Pro Ala Pro Ala Ser Ser Thr Pro Gln Glu Pro Trp
                165                 170                 175
Pro Gly Pro Thr Ala Pro Ser Pro Thr Ser Arg Pro Pro Trp Ala Val
                180                 185                 190
Asp Pro Ala Phe Ala Glu Arg Tyr Ala Pro Asp Lys Thr Ser Thr Val
                195                 200                 205
Leu Thr Arg His Ser Gln Pro Ala Thr Pro Thr Pro Leu Gln Ser Arg
    210                 21                  220
Thr Ser Ile Val Gln Ala Ala Gly Val Pro Gly Gly Gly Ser
225                 230                 235                 240
Asn Asn Gly Lys Thr Pro Val Cys His Gln Cys His Gln Val Ile Arg
                245                 250                 255
Ala Arg Tyr Leu Val Ala Leu Gly His Ala Tyr His Pro Glu Glu Phe
                260                 265                 270
Val Cys Ser Gln Cys Gly Lys Val Leu Glu Glu Gly Gly Phe Phe Glu
                275                 280                 285
Glu Lys Gly Ala Ile Phe Cys Pro Pro Cys Tyr Asp Val Arg Tyr Ala
    290                 295                 300
Pro Ser Cys Ala Lys Cys Lys Lys Ile Thr Gly Glu Ile Met His
305                 310                 315                 320
Ala Leu Lys Met Thr Trp His Val Leu Cys Phe Thr Cys Ala Ala Cys
                325                 330                 335
Lys Thr Pro Ile AEg Asn Arg Ala Phe Tyr Met Glu Glu Gly Val Pro
                340                 345                 350
Tyr Cys Glu Arg Asp Tyr Glu Lys Met Phe Gly Thr Lys Cys Gln Trp
    355                 360                 365
Cys Asp Phe Lys Ile Asp Ala Gly Asp Arg Phe Leu Glu Ala Leu Gly
    370                 375                 380
Phe Ser Trp His Asp Thr Cys Phe Val Cys Ala Ile Cys Gln Ile Asn
385                 390                 395                 400
Leu Glu Gly Lys Thr Phe Tyr Ser Lys Lys Asp Arg Pro Leu Cys Lys
                405                 410                 415
Ser His Ala Phe Ser His Val
                420
```

This 423 amino acid protein demonstrates 100% homology to the protein shown in SEQ. ID NO. 10, except for the sequence in the highlighted area (amino acids 94-99), which are due to the nucleotide changes depicted above.

The second novel human heart cDNA sequence (SEQ. ID NO: 39) comprises 1575 bp:

```
CGACGCAGAG CAGCGCCCTG GCCGGGCCAA GCAGGAGCCG GCATCATGGA TTCCTTCAAG      60

GTAGTGCTGG AGGGGCCAGC ACCTTGGGGC TTCCGGCTGC AAGGGGGCAA GGACTTCAAT     120

GTGCCCCTCT CCATTTCCCG GCTCACTCCT GGGGGCAAAG CGGCGCAGGC CGGAGTGGCC     180

GTGGGTGACT GGGTGCTGAG CATCGATGGC GAGAATGCGG GTAGGCTCAC ACACATCGAA     240

GCTCAGAACA AGATCCGGGC CTGCGGGGAG CGCCTCAGCC TGGGCCTCAG CAGGGCCCAG     300
```

```
                    -continued
CCGGTTCAGA GCAAACCGCA GAAGGCCTCC GCCCCCGCCG CGGACCCTCC GCGGTACACC    360

TTTGCACCCA GCGTCTCCCT CAACAAGACG GCCCGGCCCT TTGGGGCGCC CCCGCCCGCT    420

GACAGCGCCC CGCAACAGAA TGGGTGCAGA CCCCTGACAAACAGCCGCTC CGACCGCTGG    480

TCCCAGATGC CAGCAAGCAG CGGCTGATGG AGAACACAGA GGACTGGCGG CCGCGGCCGG    540

GGACAGGCCA GTCGCGTTCC TTCCGCATCC TTGCCCACCT CACAGGCACC GAGTTCATGC    600

AAGACCCGGA TGAGGAGCAC CTGAAGAAAT CAAGCCAGGT GCCCAGGACA GAAGCCCCAG    660

CCCCAGCCTC ATCTACACCC CAGGAGCCCT GGCCTGGCCC TACCGCCCCC AGCCCTACCA    720

GCCGCCCGCC CTGGGCTGTG GACCCTGCGT TTGCCGAGCG CTATGCCCCG GACAAAACGA    780

GCACAGTGCT GACCCGGCAC AGCCAGCCGG CCACGCCCAC GCCGCTGCAG AGCCGCACCT    840

CCATTGTGCA GGCAGCTGCC GGAGGGGTGC CAGGAGGGGG CAGCAACAAC GGCAAGACTC    900

CCGTGTGTCA CCAGTGCCAC AAGGTCATCC GGGGCCGCTA CCTGGTGGCG TTGGGCCACG    960

CGTACCACCC GGAGGAGTTT GTGTGTAGCC AGTGTGGGAA GGTCCTGGAA GAGGGTGGCT    1020

TCTTTGAGGA GAAGGGCGCC ATCTTCTGCC CACCATGCTA TGACGTGCGC TATGCACCCA    1080

GCTGTGCCAA GTGCAAGAAG AAGATTACAG GCGAGATCAT GCACGCCCTG AAGATGACCT    1140

GGCACGTGCA CTGCTTTACC TGTGCTGCCT GCAAGACGCC CATCCGGAAC AGGGCCTTCT    1200

ACATGGAGGA GGGCGTGCCC TATTGCGAGC GAGACTATGA GAAGATGTTT GGCACGAAAT    1260

GCCATGGCTG TGACTTCAAG ATCGACGCTG GGGACCGCTT CCTGGAGGCC CTGGGCTTCA    1320

GCTGGCATGA CACCTGCTTC GTCTGTGCGA TATGTCAGAT CAACCTGGAA GGAAAGACCT    1380

TCTACTCCAA GAAGGACAGG CCTCTCTGCA AGAGCCATGC CTTCTCTCAT GTGTGAGCCC    1440

CTTCTGCCCA CAGCTGCCGC GGTGGCCCCT AGCCTGAGGG GCCTGGAGTC GTGGCCCTGC    1500

ATTTCTGGGT AGGGCTGGCA ATGGTTGCCT TAACCCTGGC TCCTGGCCCG AGCCTGGGCT    1560

CCCGGGCCCT GCCCA                                                    1575
```

Reading frame shifts caused by the addition of a 17 by fragment (bolded, italicized and underlined) results in an early translation stop codon at position 565-567 (underlined). The derived amino acid sequence (SEQ. ID NO: 40) consists of 153 amino acids:

```
Met Asp Ser Phe Lys Val Val Leu Glu Gly Pro Ala Pro Trp Gly Phe
 1               5                  10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
        115                 120                 125
```

-continued

<u>Pro Gln Gln Asn Gly Cys Arg Pro Leu Thr Asn Ser Arg Ser Asp Arg</u>
130                     135                     140

<u>Trp Ser Gln Met Pro Ala Ser Ser Gly</u>
145                 150

This protein demonstrates 100% homology to SEQ. ID NO: 10 until amino acid 94, where the addition of the 17 by fragment depicted in the nucleotide sequence results in a frame shift. Over amino acids 94-153, the protein is not homologous to SEQ. ID NO: 10. Amino acids 154-457 in SEQ. ID NO: 10 are not present due to the early stop codon depicted in nucleotide sequence.

Example 54

Genomic HLMP-1 Nucleotide Sequence

Applicants have identified the genomic DNA sequence encoding HLMP-1, including putative regulatory elements associated with HLMP-1 expression. The entire genomic sequence is shown in SEQ. ID. NO: 41. This sequence was derived from ACO23788 (clone RP11-564G9), Genome Sequencing Center, Washington University School of Medicine, St. Louis, Mo.

The putative promoter region for HLMP-1 spans nucleotides 2,660-8,733 in SEQ. ID NO: 41. This region comprises, among other things, at least ten potential glucocorticoid response elements ("GREs") (nucleotides 6148-6153, 6226-6231, 6247-6252, 6336-6341, 6510-6515, 6552-6557, 6727-6732, 6752-6757, 7738-7743, and 8255-8260), twelve potential Sma-2 homologues to Mothers against Drosophila decapentaplegic ("SMAD") binding element sites (nucleotides 3569-3575, 4552-4558, 4582-4588, 5226-5232, 6228-6234, 6649-6655, 6725-6731, 6930-6936, 7379-7384, 7738-7742, 8073-8079, and 8378-8384), and three TATA boxes (nucleotides 5910-5913, 6932-6935, and 7380-7383). The three TATA boxes, all of the GREs, and eight of the SMAD binding elements ("SBEs") are grouped in the region spanning nucleotides 5,841-8,733 in SEQ. ID NO: 41. These regulatory elements can be used, for example, to regulate expression of exogenous nucleotide sequences encoding proteins involved in the process of bone formation. This would permit systemic administration of therapeutic factors or genes relating to bone formation and repair, as well as factors or genes associated with tissue differentiation and development.

In addition to the putative regulatory elements, 13 exons corresponding to the nucleotide sequence encoding HLMP-1 have been identified. These exons span the following nucleotides in SEQ. ID NO: 41:

7 Exon 1 8733-8767 Exon 2 9790-9895 Exon 3 13635-13787 Exon 4 13877-13907 Exon 5 14387-14502 Exon 6 15161-15297 Exon 7 15401-15437 Exon 8 16483-16545 Exon 9 16689-16923 Exon 10 18068-18248 Exon 11 22117-22240 Exon 12 22323-22440 Exon 13 22575-22911

In HLMP-2 there is another exon (Exon 5A), which spans nucleotides 14887-14904.

Example 55

Expression of HLMP-1 in Intervertebral Disc Cells

LIM mineralization protein-1 (LMP-1) is an intracellular protein that can direct cellular differentiation in osseous and non-osseous tissues. This example demonstrates that expressing human LMP-1 ("HLMP-1") in intervertebral disc cells increases proteoglycan synthesis and promotes a more chondrocytic phenotype. In addition, the effect of HLMP-1 expression on cellular gene expression was demonstrated by measuring Aggrecan and BMP-2 gene expression. Lumbar intervertebral disc cells were harvested from Sprague-Dawley rats by gentle enzymatic digestion and cultured in monolayer in DMEM/F12 supplemented with 10% FBS. These cells were then split into 6 well plates at approximately 200, 000 cells per well and cultured for about 6 days until the cells reached approximately 300,000 cells per well. The culture media was changed to 1% FBS DMEM/F12 and this was considered Day 0.

Replication deficient Type 5 adenovirus comprising a HLMP-1 cDNA operably linked to a cytomegalovirus ("CMV") promoter has been previously described, for example, in U.S. Pat. No. 6,300,127. The negative control adenovirus was identical except the HLMP-1 cDNA was replaced by LacZ cDNA. For a positive control, uninfected cultures were incubated in the continuous presence of BMP-2 at a concentration of 100 nanograms/milliliter.

On Day 0, the cultures were infected with adenovirus for 30 minutes at 37° C. in 300 microliters of media containing 1% FBS. Fluorescence Activated Cell Sorter ("FACS") analysis of cells treated with adenovirus containing the green fluorescent protein ("GFP") gene ("AdGFP") was performed to determine the optimal dose range for expression of transgene. The cells were treated with adenovirus containing the human LMP-1 cDNA (AdHLMP-1) (at MOIs of 0, 100, 300, 1000, or 3000) or with adenovirus containing the LacZ marker gene (AdLacZ MOI of 1000) (negative control). The culture media was changed at day 3 and day 6 after infection.

Proteoglycan production was estimated by measuring the sulfated glycosaminoglycans (sGAG) present in the culture media (at day 0, 3, and 6) using a di-methyl-methylene blue ("DMMB") calorimetric assay.

For quantification of Aggrecan and BMP-2 mRNA, cells were harvested at day 6 and the mRNA extracted by the Trizol technique. The mRNA was converted to cDNA using reverse-transcriptase and used for real-time PCR, which allowed the relative abundance of Aggrecan and BMP-2 message to be determined. Real time primers were designed and tested for Aggrecan and BMP-2 in previous experiments. The Cybergreen technique was used. Standardization curves were used to quantitate mRNA abundance.

For transfected cells, cell morphology was documented with a light microscope. Cells became more rounded with AdHLMP-1 (MOI 1000) treatment, but not with AdLacZ treatment. AdLacZ infection did not significantly change cell morphology.

FACS analysis of rat disc cells infected with ADGFP at MOI of 1000 showed the highest percentage cells infected (45%).

There was a dose dependent increase between sGAG production and AdhLMP-1 MOI. These data are seen in FIG. 1, which shows the production of sGAG after over-expressing HLMP-1 at different MOIs in rat disc cells in monolayer cultures. The results have been normalized to day 0 untreated cells. Error bars represent the standard error of the mean. As shown in FIG. 1, the sGAG production observed at day 3 was relatively minor, indicating a lag time between transfection and cellular production of GAG. Treatment with AdLacZ did not significantly change the sGAG production. As also shown in FIG. 1, the optimal dose of AdhLMP-1 was at a MOI of 1000, resulting in a 260% enhancement of sGAG production over the untreated controls at day 6. Higher or lower doses of AdhLMP-1 lead to a diminished response.

Figure 2:
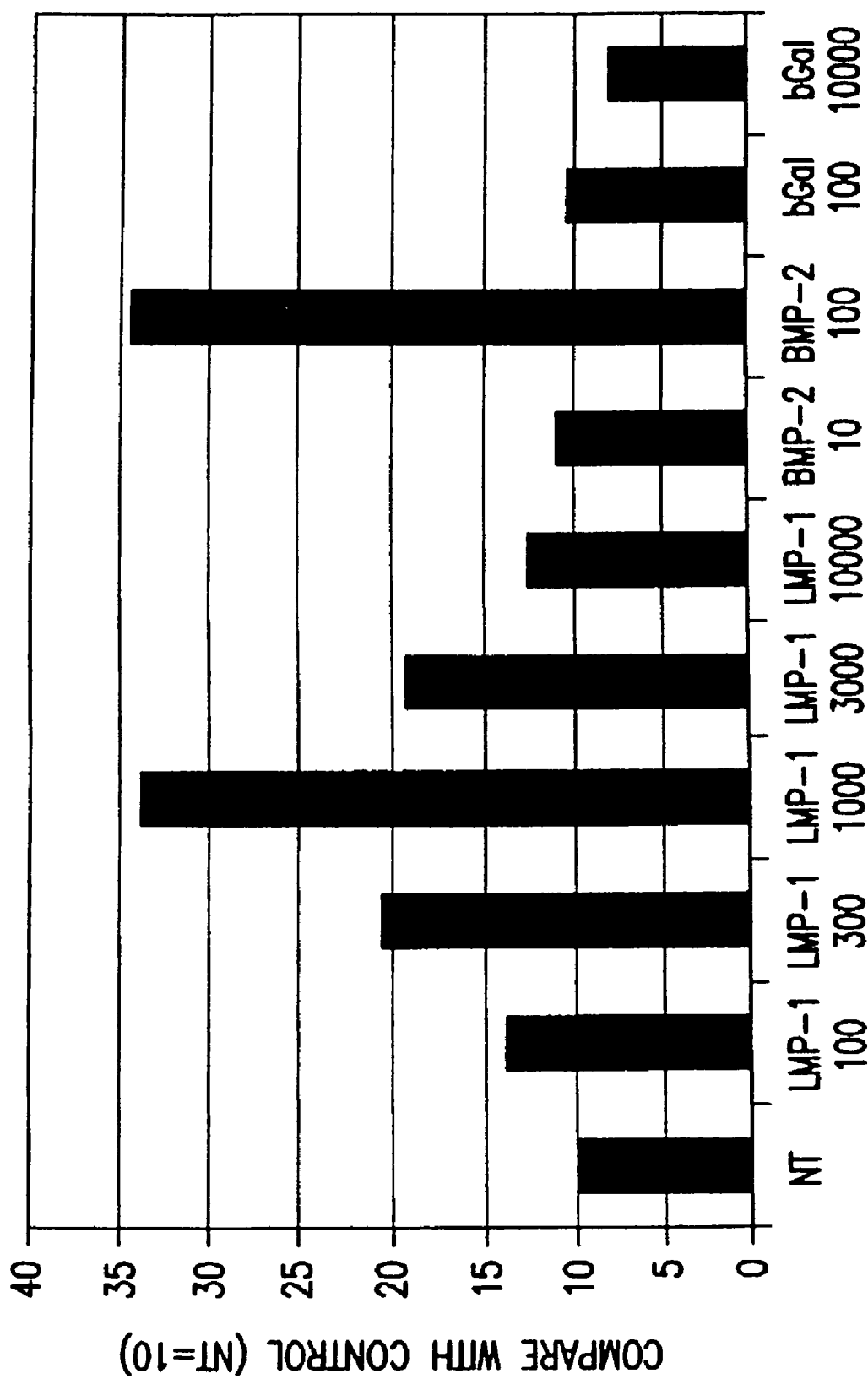
FIG. 2 is a chart showing the dose response of rat intervertebral disc cells six days after infection with different MOI of AdHLMP-1.

The effect of AdhLMP-1 dosage (MOI) on sGAG production is further illustrated in FIG. 2. FIG. 2 is a chart showing rat disc sGAG levels at day 6 after treatment with AdhLMP-1 at different MOIs. As can be seen from FIG. 2, the optimal dose of AdhLMP-1 was at a MOI of 1000.

Figure 3:
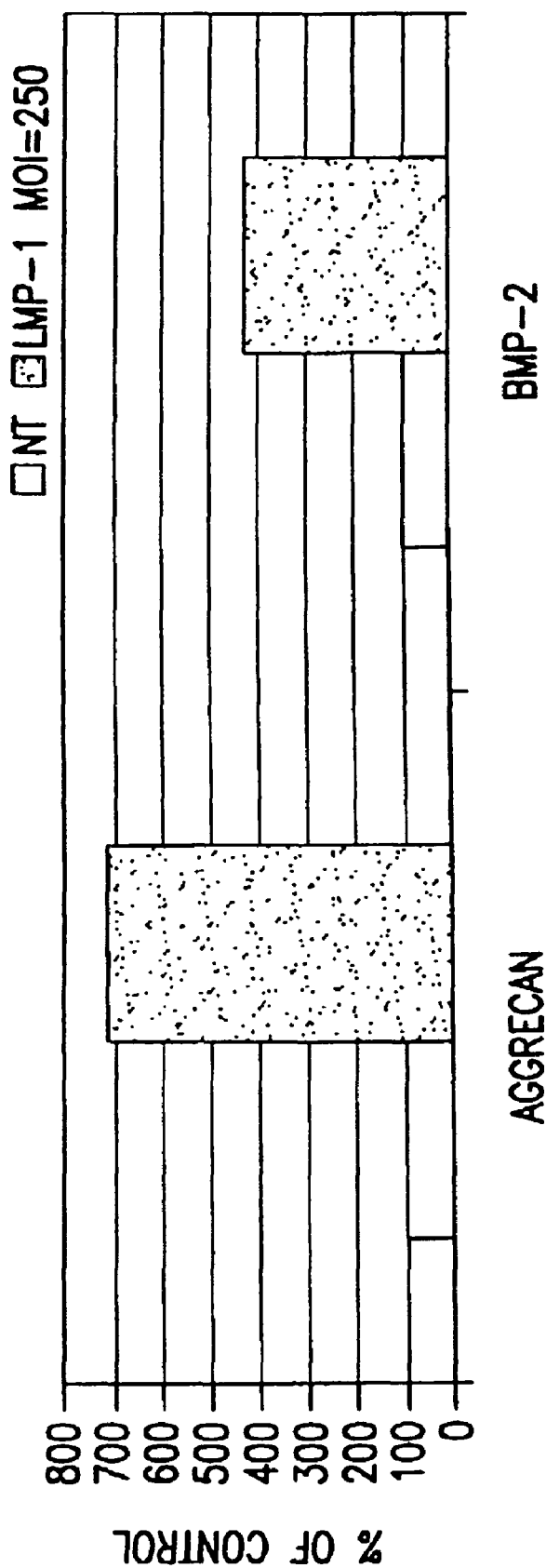
FIG. 3 is a chart showing the expression of Aggrecan and BMP-2 mRNA by AdHLMP-1 transfected rat intervertebral disc cells six days following transfection with an MOI of 250 virions/cell.
Figure 4A:
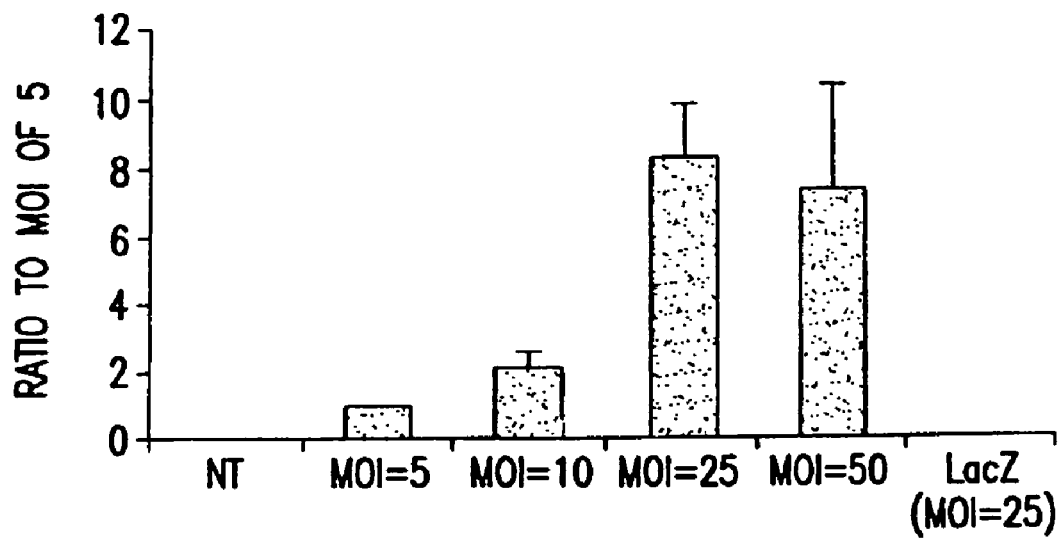
FIG. 4A is a chart showing HLMP-1 mRNA expression 12 hours after infection with Ad-hLMP-1 at different MOIs.
Figure 4B:
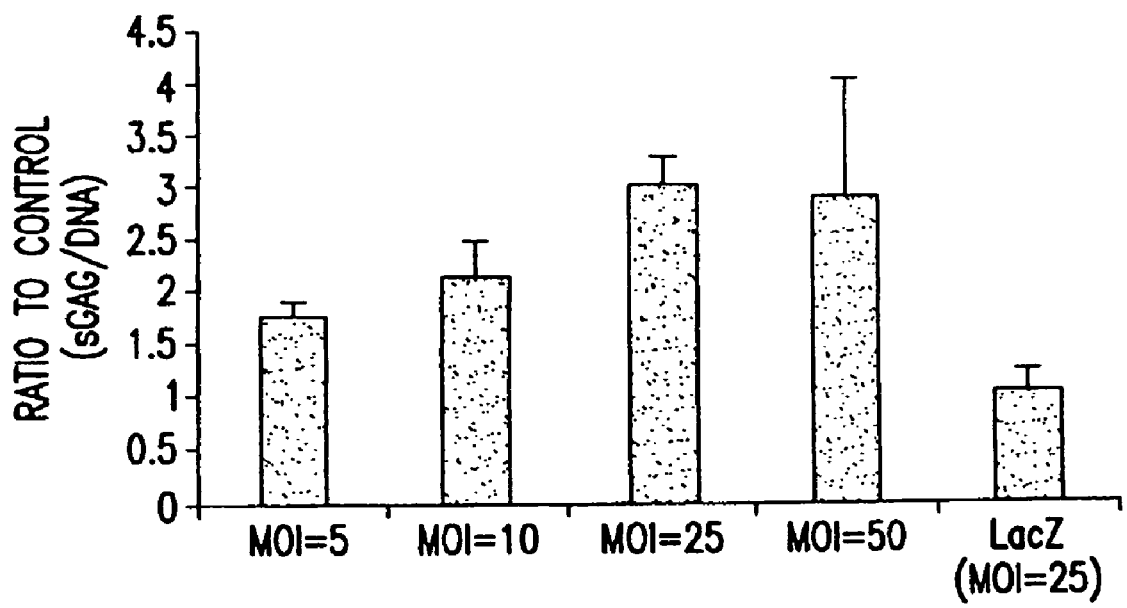
FIG. 4B is a chart showing the production of sGAG in medium from 3 to 6 days after infection. DMMB assay was used to quantitate total sGAG production between days 3 to 6 after infection. The data in FIG. 4B is normalized to the control (i.e., no treatment) group. As can be seen from FIG. 4B, there was a dose dependent increase in sGAG. with the peak of approximately three fold increase above control reached with a MOI of 25 and 50. The negative control, Ad-LacZ at a MOI of 25, lead to no increase in sGAG.
Figure 5:
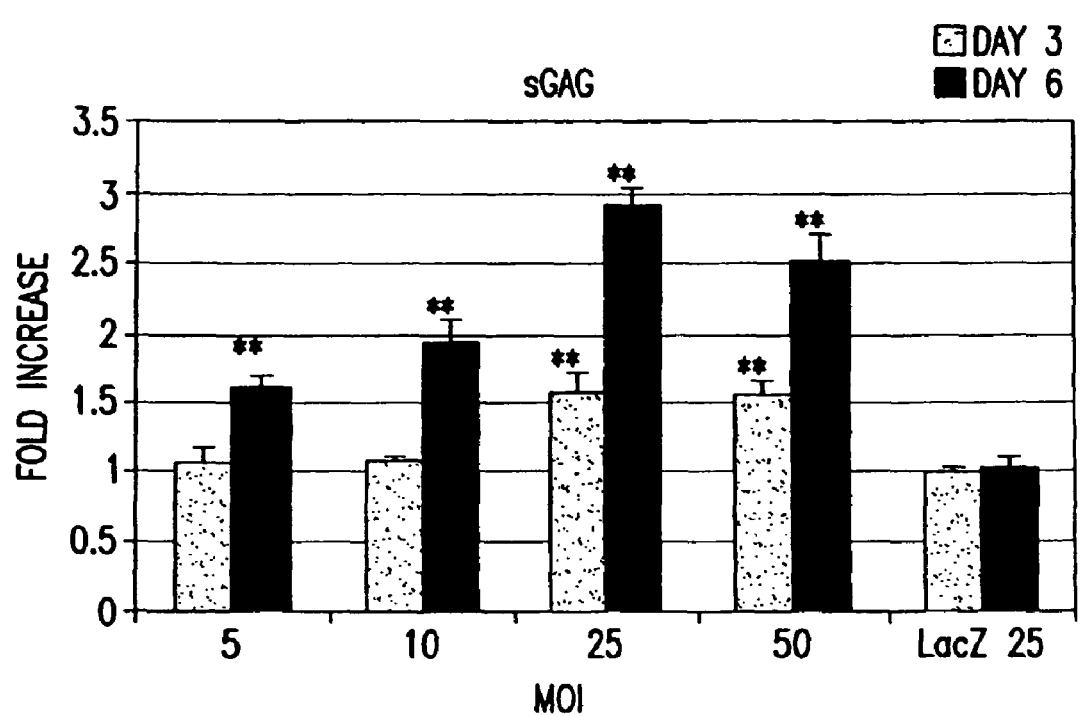
FIG. 5 is a chart showing time course changes of the production of sGAG. As can be seen from FIG. 5, on day 3 sGAG production increased significantly at a MOI of 25 and 50. On day there was a dose dependent increase in sGAG production in response to AdLMP-1. The plateau level of sGAG increase was achieved at a MOI of 25. As can also be seen from FIG. 5, treatment with AdLacZ ("LacZ") did not significantly change the sGAG production. Each result is expressed as mean with SD for six to nine samples.
Figure 6A:
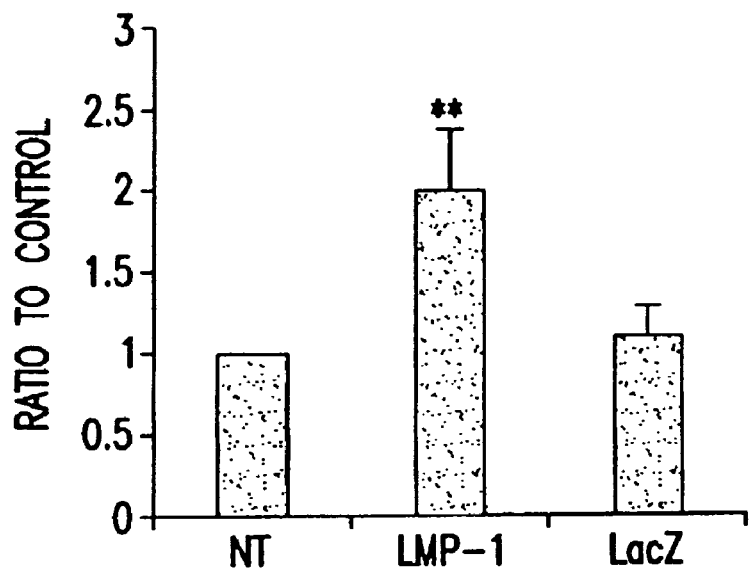
FIGS. 6A and 6B are charts showing gene response to LMP-1 over-expression in rat annulus fibrosus cells for aggrecan and BMP-2, respectively. Quantitative real-time PCR was performed on day 3 after infection with Ad-LMP-1 ("LMP-1") at a MOI of 25. As can be seen from FIGS. 6A and 6B, the gene expression of aggrecan and BMP-2 increased significantly after infection with Ad-LMP-1 compared to the untreated control ("NT"). Further, treatment with AdLacZ ("LacZ") at a MOI of 25 did not significantly change the gene expression of either aggrecan or BMP-2 compared to the untreated control.
Figure 6B:
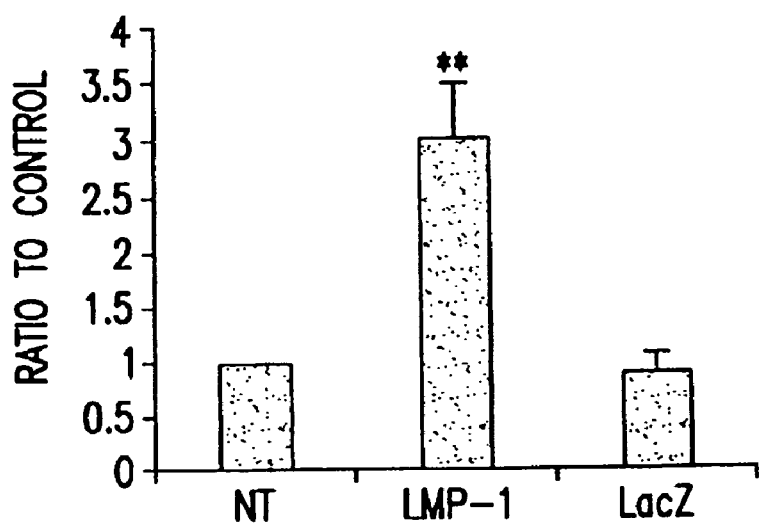
Figure 7:
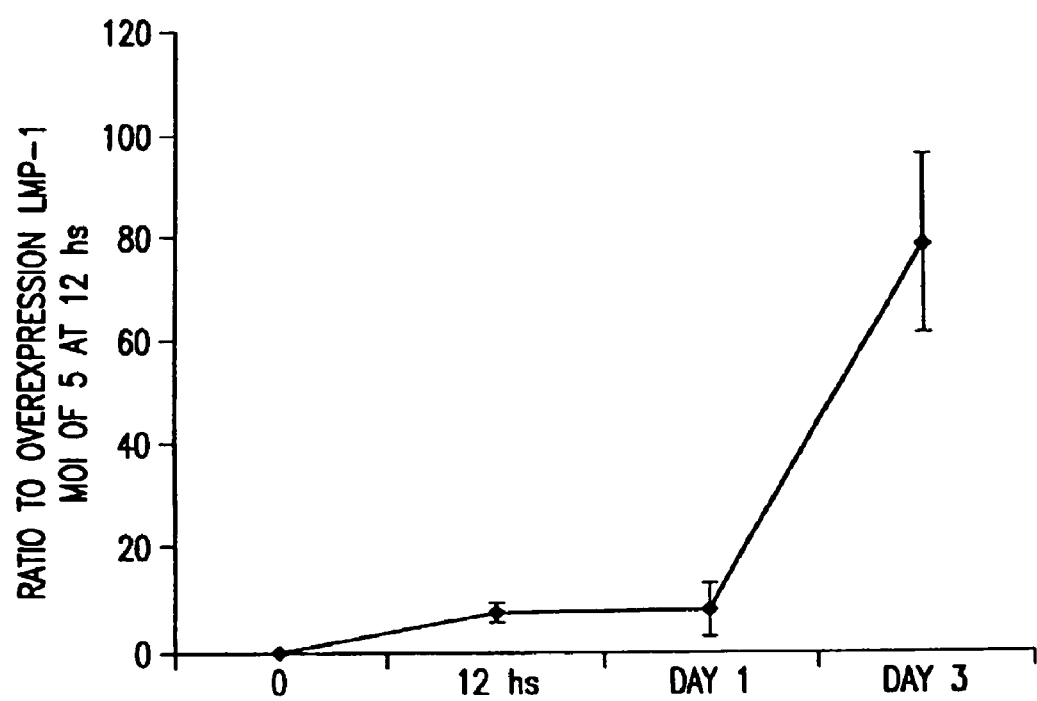
FIG. 7 is a graph showing the time course of HLMP-1 mRNA levels in rat annulus fibrosus cells after infection with AdLMP-1 at a MOI of 25. The data is expressed as a fold increase above a MOI of 5 of AdLMP-1 after standardization using 18 S and replication coefficient of over-expression LMP-1 primer. As can be seen from FIG. 7, HLMP-1 mRNA was upregulated significantly as early as 12 hours after infection. Further, there was a marked increase of expression levels between day 1 and day 3. Each result in FIG. 7 is expressed as mean with SD for six samples.
Figure 8:
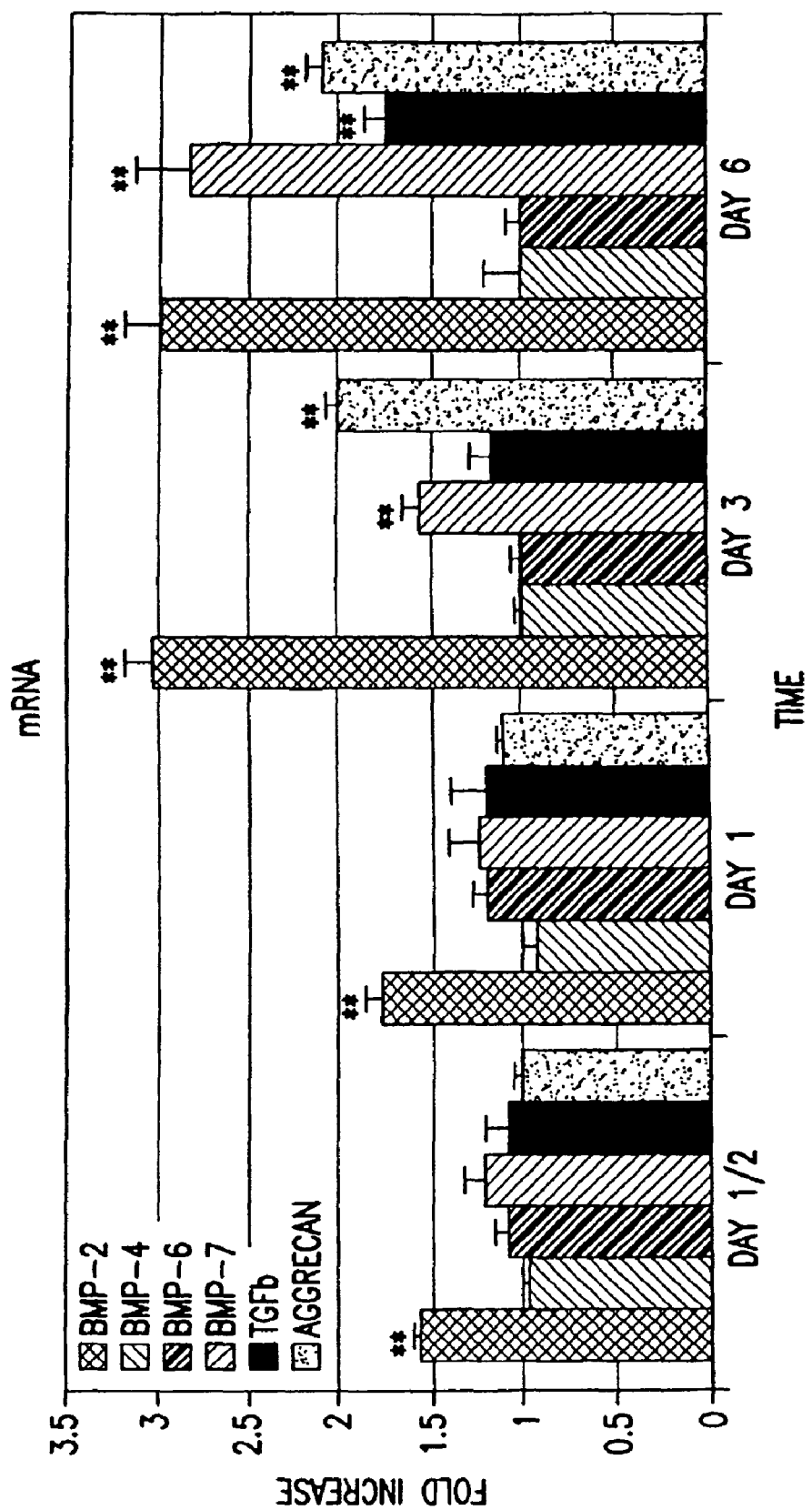
FIG. 8 is a chart showing changes in mRNA levels of BMPs and aggrecan in response to HLMP-1 over-expression. The mRNA levels of BMP-2, BMP-4, BMP-6, BMP-7, and aggrecan were determined with real-time-PCR at different time points after infection with Ad-hLMP-1 at a MOI of 25. As can be seen from FIG. 8, BMP-2 mRNA was upregulated significantly as early as 12 hours after infection with AdLMP-1. On the other hand, Aggrecan mRNA was not upregulated until 3 day after infection. Each result is expressed as mean with SD for six samples.
Figure 9:
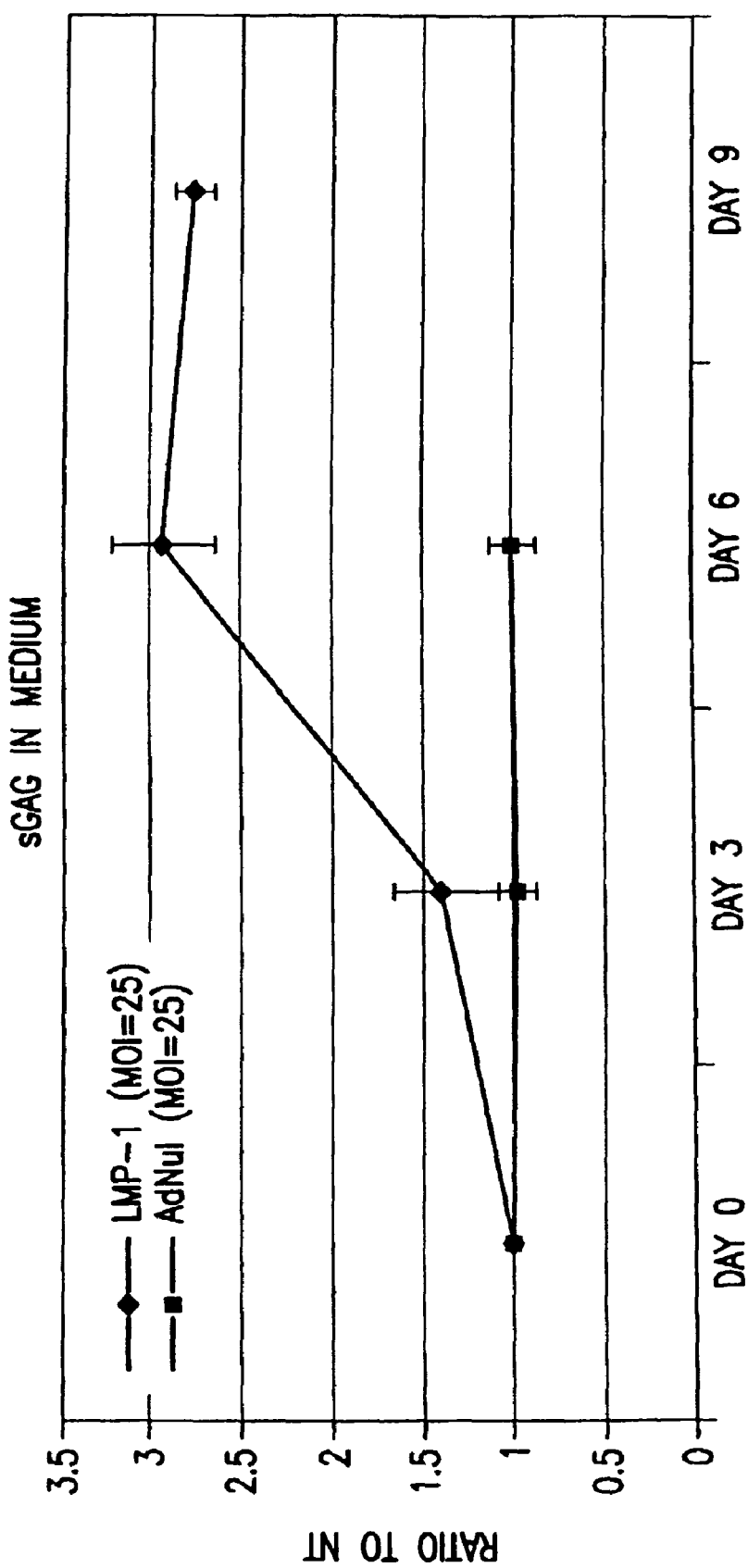
FIG. 9 is a graph showing the time course of sGAG production enhancement in response to HLMP-1 expression. For the data in FIG. 9, rat annulus cells were infected with Ad-hLMP-1 at a MOI of 25. The media was changed every three days after infection and assayed for sGAG with the DMMB assay. This data shows that sGAG production reaches a plateau at day 6 and is substantially maintained at day 9.
Figure 10:
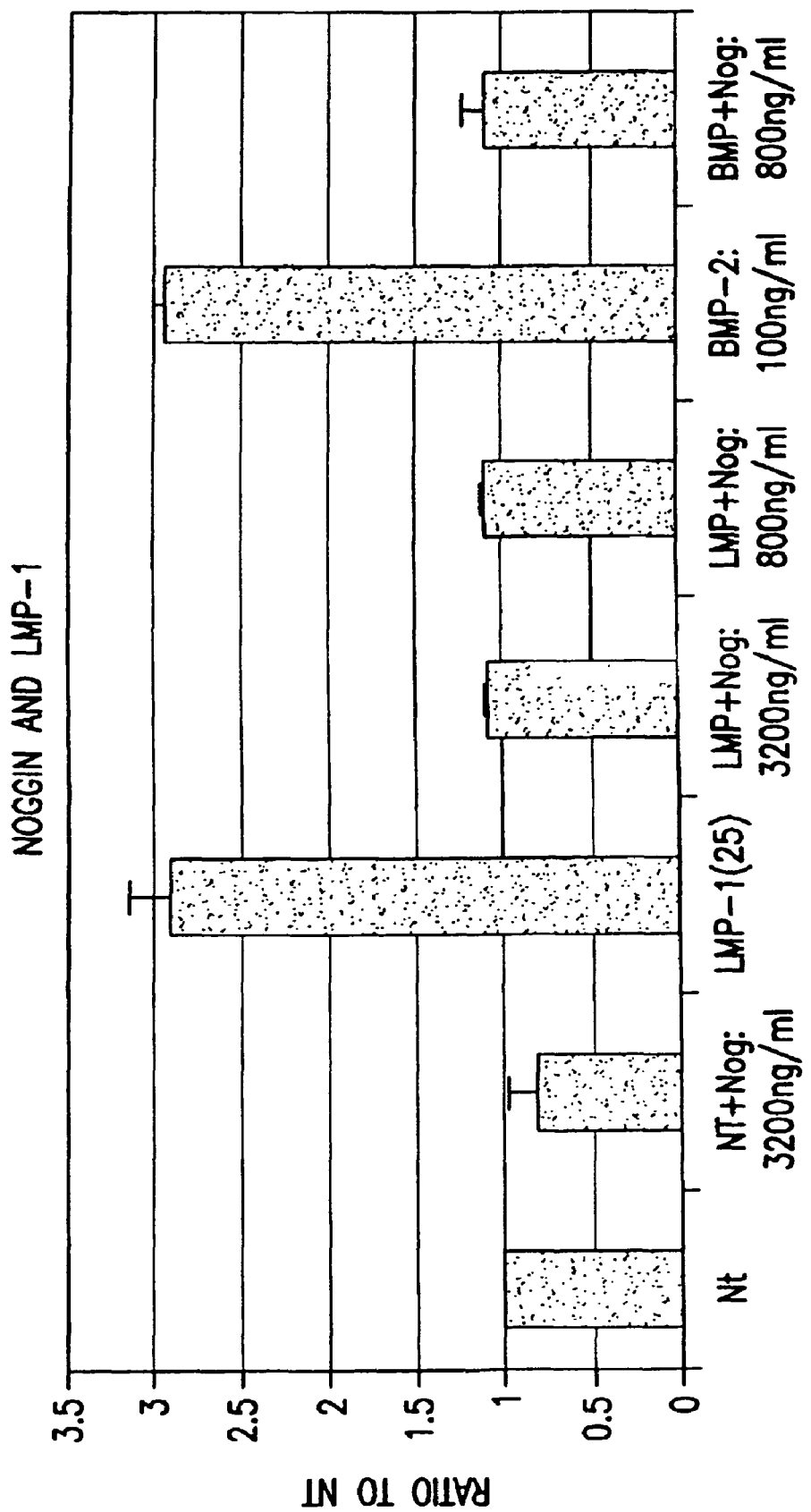
FIG. 10 is a chart showing the effect of noggin (a BMP antagonist) on LMP-1 mediated increase in sGAG production.
Figure 11:
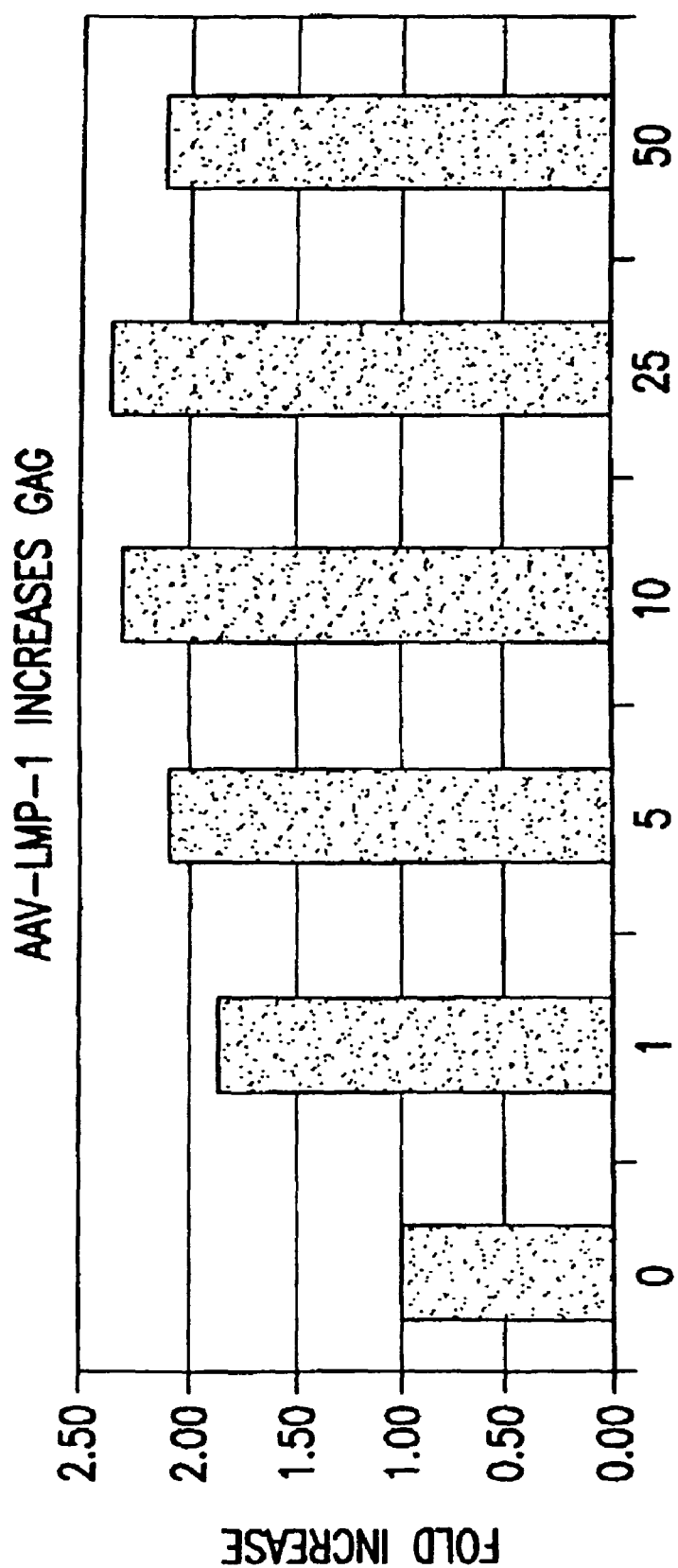
FIG. 11 is a chart showing the effect of LMP-1 on sGAG in media after day 6 of culture in monolayer. The data points are represented as fold increase above untreated cells.
Figure 12:
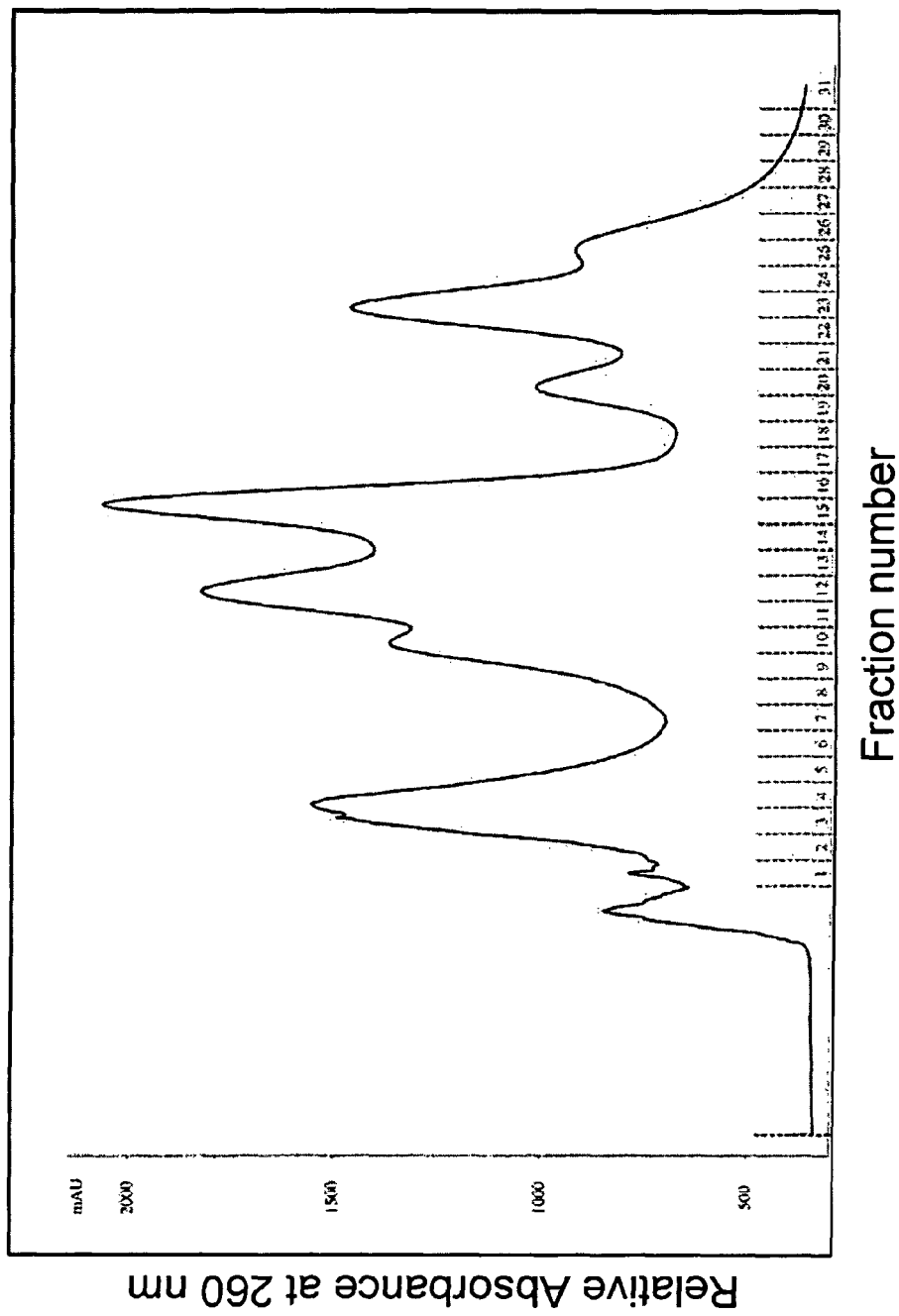
FIG. 12 shows Sephacryl S-300 molecular exclusion chromatographic profile obtained for the crude A549 lysate. The clarified lysate was applied to Sephacryl S-300 column (HiPrep 16×60) using the AKTA FPLC/Unicorn 3.1 System in 50 mM phosphate buffer, pH 7.5 and 5 M NaCl. After the void volume eluted from the column, fractions (6 ml) were collected. Fractions containing fusion proteins were detected by western blots with LMP-1-specific antibody and pooled for $Ni^{++}$-affinity enrichment. Inclusion of 5 M NaCl in buffer avoided non-specific aggregation of recombinant proteins on column resin.
Figure 13:
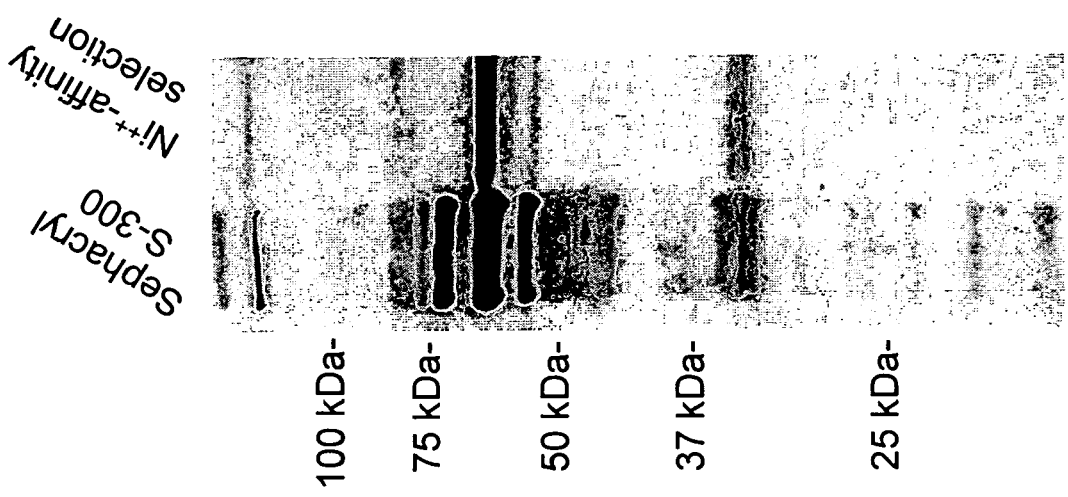
FIG. 13 is a graph showing SDS-PAGE and detection of purified LMP-1. Purified protein fractions were concentrated, dialyzed and a 5 ug aliquot of recombinant protein was loaded. The purity of pooled fractions from Sephacryl S-300 molecular exclusion chromatography and $Ni^{++}$-affinity chromatography were determined by coomassie staining of gels after SDS-PAGE (10% acrylamide). Each of the fusion-protein was the expected size as determined from molecular weight markers as marked.
Figure 14:
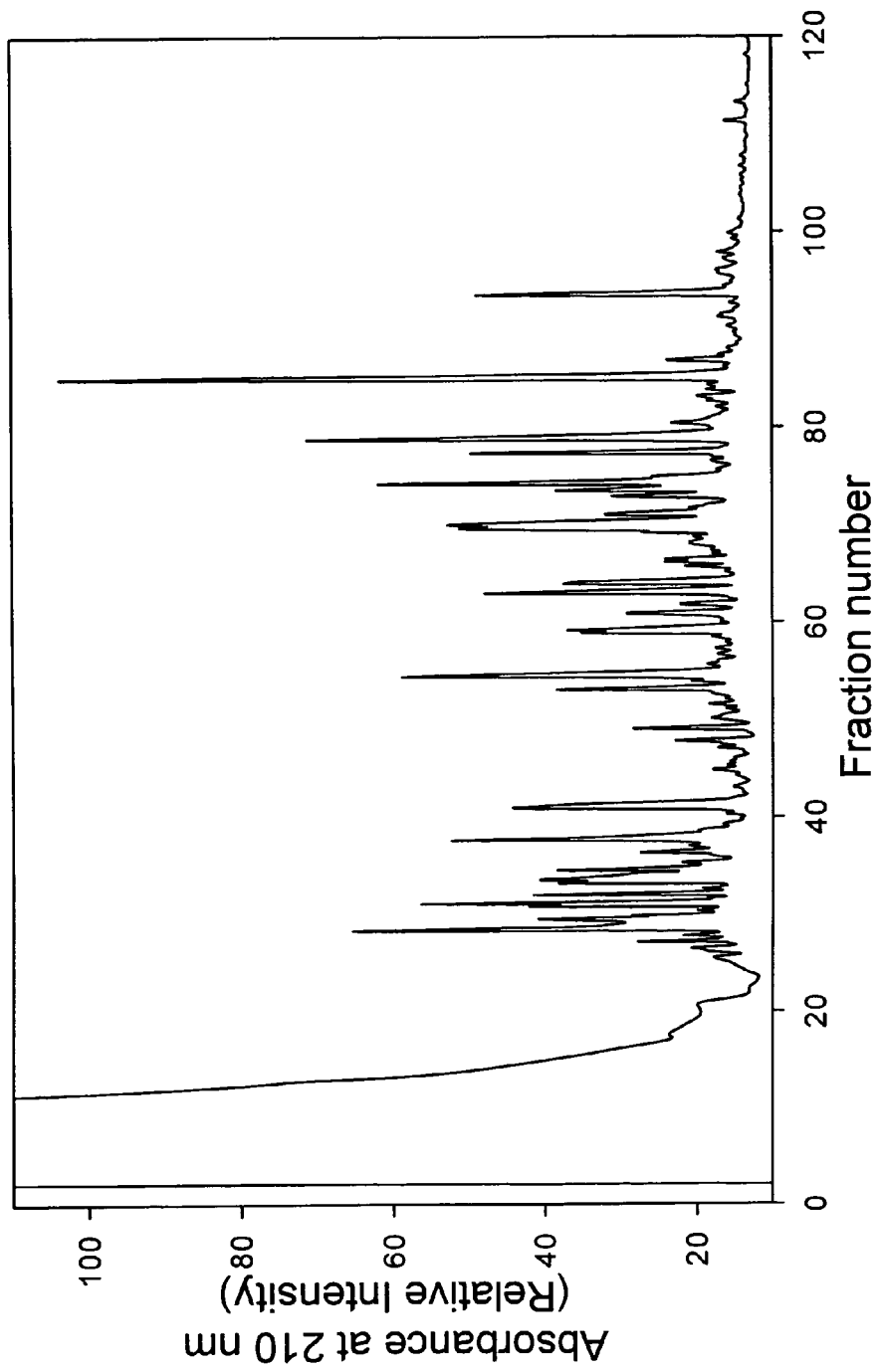
FIG. 14 is a chromatograph showing the tryptic digest (15%) OF LMP-1 purified and concentrated by a Zip Tip (Millipore) column which has $C_{18}$ resin fixed at its end. The column was rinsed in 10 μl of 0.1% trifluoroacetic acid (TFA) in 50% acetonitrile (ACN). Peptides were eluted in 10 μl 1:1 ACN-0.1% TFA. A 0.5 μl volume of the concentrated peptide-containing sample was mixed with 0.5 μl of a saturated solution of alpha-cyano-4-hydroxycinnamic acid. Each sample (0.5 ul) was spotted on the mass spectrometer sample plate for analysis.
Figure 15:
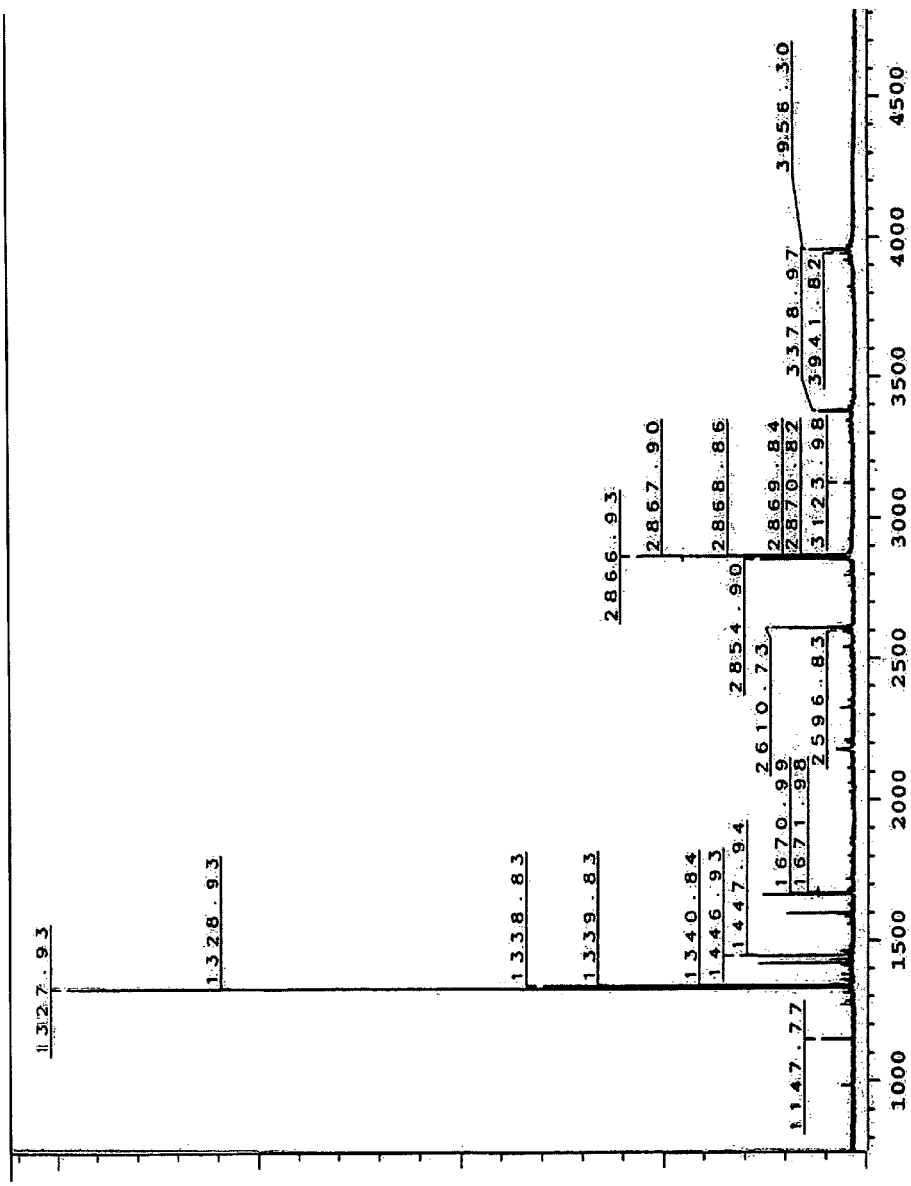
FIG. 15 is a graph showing post source decay (PSD) MALDI MS analysis of a LMP-1 derived molecular ion (m/Z=1328). HPLC-purified peptide was subjected to ion generation by post-source decay using the FAST™ method as described in the methods. A matrix-assisted laser adsorption ionization-post-source decay (MALDI-PSD) time-of-flight spectrum was recorded using α-cyano-4-hydroxy cinnamic acid as a matrix; acquisition was at 27.5 kV under continuous extraction conditions; reflector voltage was stepped from 30 to 1.27 kV, and the spectrum was constructed. A representative analysis on one of the matching molecular ions obtained from tryptic digest of LMP-1 running at m/z=1328 is shown. Indeed, the product ion spectrum of m/z=1328 confirmed the identity of this ion with the a tryptic fragment of LMP-1.
Figure 16:
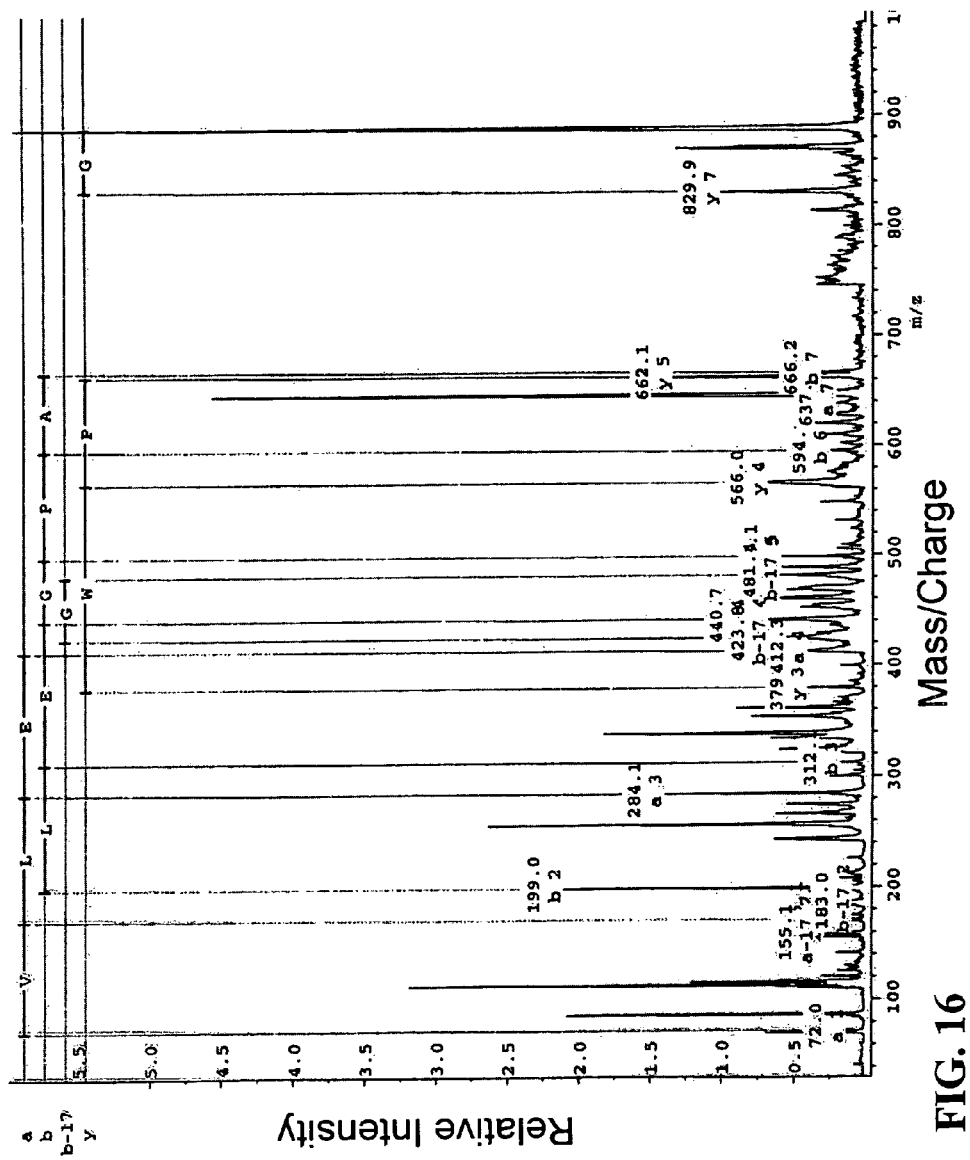
FIG. 16 is a chromatograph of a tryptic peptide mixture (85%) of LMP-1 after digestion was separated by capillary reversed-phase HPLC using the method described before [Hubalek, F., Edmondson]. The peptide fragments were separated by small bore reverse phase HPLC on a Vydac $C_{18}$ column (4.6×250 mm) with a gradient HPLC system (Waters). The chromatographic run was performed with an aqueous phase containing 0.1% trifluoroacetic acid and an organic phase containing 0.085% trifluoroacetic acid in acetonitrile with a flow rate of 0.5 ml/min. The gradient used for separation was 2-60% of acetonitrile during 40 min; the total run time was 60 min.
Figure 17:
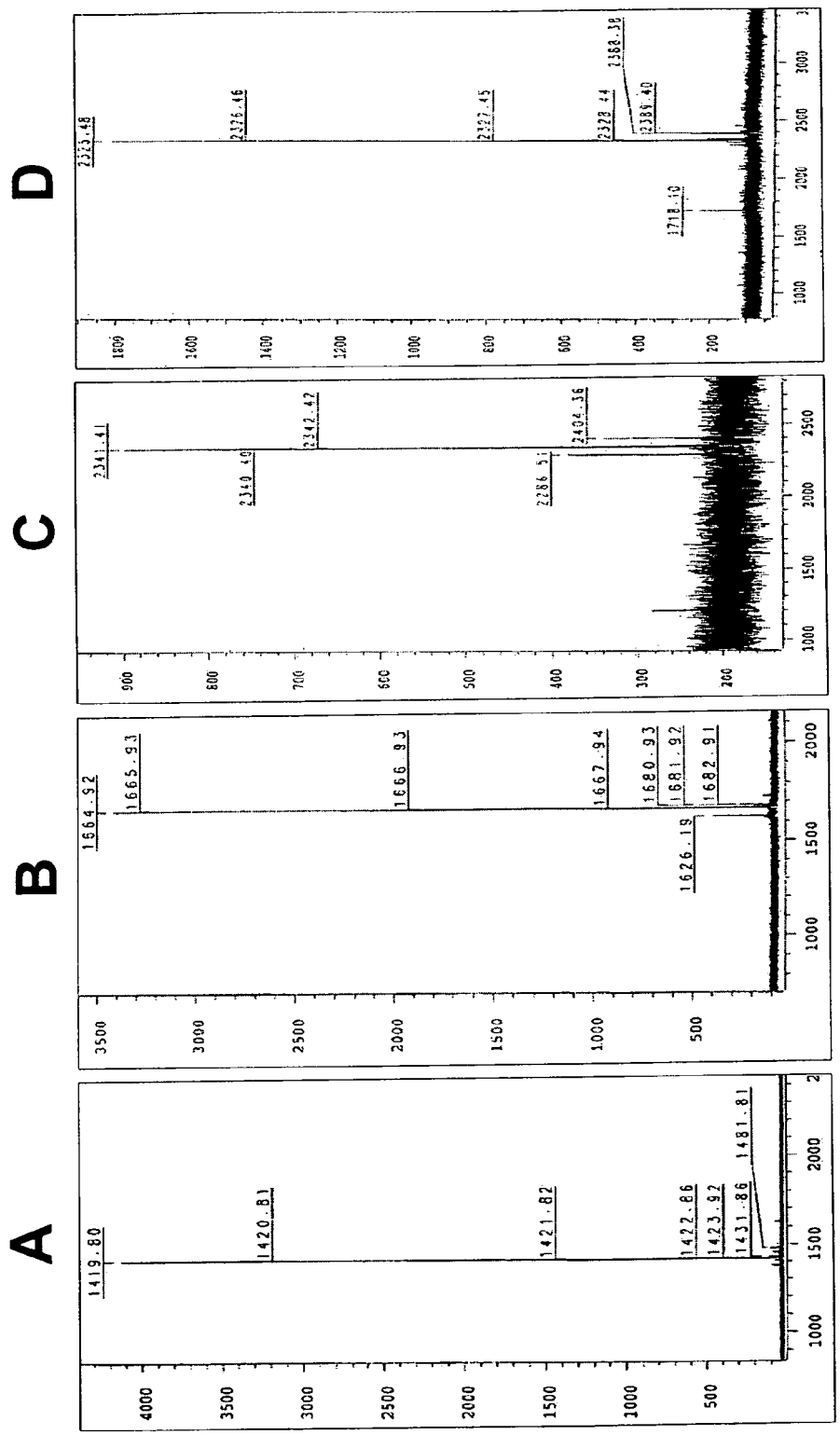
FIG. 17 is a chromatograph showing MALDI-TOF MS analysis of HPLC separated tryptic peptide fractions of LMP-1. A representative data obtained for fractions 33 (A), 35 (B), 48 (C) and 51 (D) is shown. These samples contained an exact match of the expected molecular ions for the corresponding peptide species derived from LMP-1.

Aggrecan and BMP-2 mRNA production is seen in FIG. 3. This figure demonstrates the increase in Aggrecan and BMP-2 mRNA after over-expression of HLMP-1. Real-time PCR of mRNA extracted from rat disc cells at day 6 was performed comparing the no-treatment ("NT") cells with cells treated with AdhLMP-1 at a MOI of 250. The data in FIG. 3 are represented as a percentage increase over the untreated sample. As illustrated in FIG. 3, a significant increase in Aggrecan and BMP-2 mRNA was noted following AdhLMP-1 treatment. The increase in BMP-2 expression suggests that BMP-2 is a down-stream gene that mediates HLMP-1 stimulation of proteoglycan synthesis.

These data demonstrate that transfection with AdhLMP-1 is effective in increasing proteoglycan synthesis of intervertebral disc cells. The dose of virus leading to the highest transgene expression (MOI 1000) also leads to the highest induction of sGAG, suggesting a correlation between HLMP-1 expression and sGAG induction. These data indicate that HLMP-1 gene therapy is a method of increasing proteoglycan synthesis in the intervertebral disc, and that HLMP-1 is a agent for treating disc disease.

TABLE 2

Primer Sequences for RT-PCR & Real-time PCR of SYBR Green

| Primer | Sequence | |
|---|---|---|
| Primer Sequence Aggrecan (forward) | AAGGATGGCTTCCACCAGTGC | (SEQ ID NO: 83) |
| Aggrecan (reverse) | TGCGTAAAAGACCTCACCCTCC | (SEQ ID NO: 46) |
| BMP-2 (forward) | CACAAGTCAGTGGGAGAGC | (SEQ ID NO: 47) |
| BMP-2 (reverse) | GCTTCCGCTGTTTGTGTTTG | (SEQ ID NO: 48) |

TABLE 2-continued

Primer Sequences for RT-PCR & Real-time PCR of SYBR Green

| Primer | Sequence | |
|---|---|---|
| GAPDH (forward) | ACCACAGTCCATGCCATCAC | (SEQ ID NO: 49) |
| GAPDH (reverse) | TCCACCACCCTGTTGCTGTA | (SEQ ID NO: 50) |

GAPDH in Table 2 denotes glyceraldehyde phosphate dehydrogenase.

TABLE 3

Primer and Probe sequences for Real-time PCR of TaqMan ®

| Primer | Sequence | |
|---|---|---|
| Over-expression LMP-1 (forward) | AATACGACTCACTATAGGGCTCGA | (SEQ ID NO: 51) |
| Over-expression LMP-1 (reverse) | GGAAGCCCCAAGGTGCT | (SEQ ID NO: 52) |
| Over-expression LMP-1 (probe) | -FAM-AGCCGGCATCATGGATTCCTTCAA-TA-MPA | (SEQ ID NO: 53) |

TaqMan® Ribosomal RNA Control Reagents (Part number 4308329, Applied Biosystems, Foster City, Calif., U.S.A.) were used for the forward primer, reverse primer and probe of 18 S ribosomal RNA (rRNA) gene.

All publications cited in the specification, both patent publications and non-patent publications, are indicative of the level of skill of those skilled in the art to which this invention pertains. With exception of U.S. patent application Ser. No. 10/806,915 and U.S. Provisional Patent Application 60/456,551, all these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed:

1. An isolated chimeric nucleic acid sequence encoding a polypeptide comprising (a) a nuclear localization signal of a viral protein; and (b) a fragment of an osteogenic factor having osteogenic activity.

2. The nucleic acid sequence of claim 1, wherein the nuclear localization signal encodes a protein transduction domain from the HIV TAT protein.

3. The nucleic acid sequence of claim 2, wherein the nuclear localization signal comprises the nucleotide sequence of (SEQ ID. No. 84).

4. The nucleic acid sequence of claim 1, wherein osteogenic factor is selected from the group consisting bone morphogenic proteins and transforming growth factor-beta superfamily proteins.

5. The nucleic acid sequence of claim 1, wherein the osteogenic factor is selected from a group consisting of LIM mineralization proteins, Dlx protein, Runx and Osterix proteins.

6. The nucleic acid sequence of claim 5, wherein the osteogenic factor is a LIM mineralization protein selected from the group consisting of RLMP, HLMP-1, HLMP-1s, and HLMP-3.

7. The nucleic acid sequence of claim 6, wherein the nucleic acid sequence encodes amino acids 94-133 of HLMP-1 set forth in (SEQ. ID NO: 10).

8. The nucleic acid sequence of claim 3, wherein the nucleic acid sequence encoding an osteogenic factor is selected from the group consisting of nucleic acid sequences encoding amino acids 94-133 of HLMP-1 (SEQ ID NO: 10) and nucleic acid sequences encoding amino acids 94-153 of HLMP-3 (SEQ ID NO: 38).

9. A recombinant expression vector comprising the nucleic acid sequences of any of the claims 1-8.

10. The recombinant expression vector of claim 9, wherein the nucleic acid sequence is operably linked to a genetic control element capable of directing expression of said nucleic acid sequence in a host cell.

11. A host cell comprising the recombinant expression vector of claim 9.

12. The host cell of claim 11, wherein the host cell is prokaryotic.

13. The host cell of claim 11, wherein the host cell is eukaryotic.

14. The host cell of claim 13, wherein the eukaryotic host cell is a mammalian cell.

15. The host cell of claim 11, wherein the host cell is transiently transfected with the recombinant expression vector of claim 9.

16. The host cell of claim 15, wherein the host cell is a mammalian cell.

17. An in vitro method of manufacturing the protein encoded by the isolated chimeric nucleic acid sequence of claim 1, comprising transfecting isolated host cells with an expression vector comprising the isolated chimeric nucleic acid sequence of claim 1, whereby said protein is expressed.

18. An in vitro method of manufacturing the protein encoded by the isolated chimeric nucleic acid sequence of claim 7, comprising transfecting isolated host cells with an expression vector comprising the nucleic acid sequence of claim 7, whereby said protein is expressed.

* * * * *

UNITED STATES PATENT AND TRADEMARK OFFICE
CERTIFICATE OF CORRECTION

| | | |
|---|---|---|
| PATENT NO. | : 7,781,574 B2 | Page 1 of 2 |
| APPLICATION NO. | : 11/602120 | |
| DATED | : August 24, 2010 | |
| INVENTOR(S) | : Boden et al. | |

It is certified that error appears in the above-identified patent and that said Letters Patent is hereby corrected as shown below:

On the Title Page, in Item (73), under "Assignee", in Column 1, Line 1, after "University" insert -- (US) --, therefor.

In Column 5, Line 65, delete "day" and insert -- day 6 --, therefor.

In Column 8, Line 4, delete "5-100" and insert -- S-100 --, therefor.

In Column 17, Line 16, delete "-20C." and insert -- -20°C. --, therefor.

In Column 17, Line 57, delete "about days" and insert -- about 4 days --, therefor.

In Column 18, Line 60, delete "HLPM-1s" and insert -- HLMP-1s --, therefor.

In Column 22, Line 36, delete "25 by" and insert -- 25 bp --, therefor.

In Column 22, Line 62, delete "LMP-antisense" and insert -- LMP-1 antisense --, therefor.

In Column 24, Line 41, delete "(10000xg; min)," and insert -- (10000xg; 20 min), --, therefor.

In Column 24, Line 53, delete "(10 µmol/" and insert -- (10 pmol/ --, therefor.

In Column 25, Line 59, delete "for hours" and insert -- for 18 hours --, therefor.

In Column 26, Line 20, delete "hftp://" and insert -- http:// --, therefor.

In Column 30, Line 62, delete "cycles." and insert -- 30 cycles. --, therefor.

In Column 37, Line 12, delete "million" and insert -- 1 million --, therefor.

Signed and Sealed this
Tenth Day of July, 2012

David J. Kappos
*Director of the United States Patent and Trademark Office*

CERTIFICATE OF CORRECTION (continued)

U.S. Pat. No. 7,781,574 B2

In Column 37, Line 54, delete "(TEST)," and insert -- (TBST), --, therefor.

In Column 41, Line 47, delete "4" and insert -- ~4 --, therefor.

In Column 46, Line 53, after "or" insert -- 25 --.

In Column 48, Line 24, after "are" delete "a".

In Columns 49-50, Line 3, delete "GPGCCCTCT" and insert -- GTGCCCCTCT --, therefor.

In Columns 49-50, Line 4, delete "GAGAATCCGG" and insert -- GAGAATGCGG --, therefor.

In Columns 49-50, Line 19, delete "CGAGACTATC" and insert -- CGAGACTATG --, therefor.

In Columns 49-50, Line 22, delete "AAGAGCCATC" and insert -- AAGAGCCATG --, therefor.

In Columns 49-50, Line 23, delete "ACAGCTCCCG" and insert -- ACAGCTGCCG --, therefor.

In Columns 49-50, Line 24, delete "GAGCCTGGGC" and insert -- GACCCTGGGC --, therefor.

In Column 49, Line 26, delete "119 by" and insert -- 119 bp --, therefor.

In Column 49, Line 27, delete "17 by" and insert -- 17 bp --, therefor.

In Columns 49-50, Line 36, delete "Gln" and insert -- Gln --, therefor.

In Columns 49-50, Line 36, delete "Tie" and insert -- Ile --, therefor.

In Columns 49-50, Line 40, delete "Arq" and insert -- Arg --, therefor.

In Columns 51-52, Line 13, delete "21" and insert -- 215 --, therefor.

In Column 51-52, Line 28, delete "AEg" and insert -- Arg --, therefor.

In Columns 51-52, Line 59, delete "GTAGGCTCAC" and insert -- GTAGCCTCAC --, therefor.

In Columns 53-54, Line 4, delete "CCCCTGACAAACAGCCGCTC" and
insert -- CCCCTGACAA ACAGCCGCTC --, therefor.

In Column 53, Line 39, delete "17 by" and insert -- 17 bp --, therefor.

In Column 55, Line 9, delete "17 by" and insert -- 17 bp --, therefor.

SEQUENCE LISTING

<160> NUMBER OF SEQ ID NOS: 87

<210> SEQ ID NO 1
<211> LENGTH: 457
<212> TYPE: PRT
<213> ORGANISM: Rattus norvegicus

<400> SEQUENCE: 1

-continued

```
Met Asp Ser Phe Lys Val Val Leu Glu Gly Pro Ala Pro Trp Gly Phe
 1               5                  10                 15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Ala Gln Ser Lys Pro Gln Lys Ala Leu Thr
                85                  90                  95

Pro Pro Ala Asp Pro Pro Arg Tyr Thr Phe Ala Pro Ser Ala Ser Leu
            100                 105                 110

Asn Lys Thr Ala Arg Pro Phe Gly Ala Pro Pro Thr Asp Ser Ala
        115                 120                 125

Leu Ser Gln Asn Gly Gln Leu Leu Arg Gln Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu Phe Met Lys Lys Ser Ser Gln
            180                 185                 190

Val Pro Arg Thr Glu Ala Pro Ala Pro Ala Ser Thr Ile Pro Gln Glu
        195                 200                 205

Ser Trp Pro Gly Pro Thr Thr Pro Ser Pro Thr Ser Arg Pro Pro Trp
    210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Asn Arg Thr Ser Ile Val Gln Ala Ala Gly Gly Gly Thr Gly Gly
            260                 265                 270

Gly Ser Asn Asn Gly Lys Thr Pro Val Cys His Gln Cys His Lys Ile
        275                 280                 285

Ile Arg Gly Arg Tyr Leu Val Ala Leu Gly His Ala Tyr His Pro Glu
    290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Ser Cys Tyr Asp Val Arg
                325                 330                 335

Tyr Ala Pro Ser Cys Ala Lys Cys Lys Lys Ile Thr Gly Glu Ile
            340                 345                 350

Met His Ala Leu Lys Met Thr Trp His Val Pro Cys Phe Thr Cys Ala
    355                 360                 365

Ala Cys Lys Thr Pro Ile Arg Asn Arg Ala Phe Tyr Met Glu Glu Gly
370                 375                 380

Ala Pro Tyr Cys Glu Arg Asp Tyr Glu Lys Met Phe Gly Thr Lys Cys
                390                 395                 400
385

Arg Gly Cys Asp Phe Lys Ile Asp Ala Gly Asp Arg Phe Leu Glu Ala
            405                 410                 415
```

```
Leu Gly Phe Ser Trp His Asp Thr Cys Phe Val Cys Ala Ile Cys Gln
        420                 425                 430

Ile Asn Leu Glu Gly Lys Thr Phe Tyr Ser Lys Lys Asp Lys Pro Leu
        435                 440                 445

Cys Lys Ser His Ala Phe Ser His Val
        450                 455

<210> SEQ ID NO 2
<211> LENGTH: 1696
<212> TYPE: DNA
<213> ORGANISM: Rattus norvegicus

<400> SEQUENCE: 2
gcacgaggat cccagcgcgg ctcctggagg ccgccaggca gccgcccagc cgggcattca      60
ggagcaggta ccatggattc cttcaaggta gtgctggagg acctgccccc ttggggcttc     120
cgtctgcaag ggggcaagga cttcaacgtg cccctctcca tctctcggct cactcctgga     180
ggcaaggccg acaggccgg tgtggccgtg ggagactggg tactgagtat cgacggtgag      240
aacgccggaa gcctcacaca cattgaagcc agaacaagga tccgtgcctg tggggagcgc     300
ctcagcctgg gtcttagcag agcccagcct gctcagagca accacagaa ggccctgacc      360 cctcccgccg acccccgag gtacactttt gcaccaagcg cctccctcaa caagacggcc      420
cggcccttcg gggcaccccc acctactgac agcgccctgt cgcagaatgg acagctgctc     480
agacagctgg tccctgatgc cagcaagcag cggctgatgg agaatactga agactggcgc     540
ccgcggccag ggacaggcca gtcccgttcc ttccgcatcc ttgctcacct cacgggcaca     600
gagttcatgc aagacccgga tgaggaattc atgaagaagt caagccaggt gcccaggaca     660 gaagcccag ccccagcctc aaccataccc aggaatcct ggcctggccc caccaccccc      720
agccccacca gccgcccacc ctgggccgta gatcctgcat tgctgagcg ctatgcccca      780 gacaaaacca gcacagtgct gacccgacac agccagccag ccacacctac gcctctgcag     840
aaccgcacct ccatagttca ggctgcagct ggaggggca caggaggag cagcaacaat      900 ggcaagacgc ctgtatgcca ccagtgccac aagatcatcc gcggccgata cctggtagca     960
ctgggccacg cgtaccatcc tgaggaattt gtgtgcagcc agtgtgggaa ggtcctggaa    1020
gagggtggct tcttcgagga aagggagct atcttttgcc cctcctgcta tgatgtgcgc     1080
tatgcaccca gctgtgccaa atgcaagaag aagatcactg agagatcat gcatgcgctg    1140 aagatgacct ggcatgttcc ctgcttcacc tgtgcagcct gcaaaacccc tatccgcaac    1200
agggctttct acatggagga gggggctccc tactgcgagc gagattacga aagatgtttt    1260
ggcacaaagt gtcgcggctg tgacttcaag atcgatgccg ggaccgtttt cctggaagcc    1320 ctgggttca gctggcatga tacgtgtttt gtttgcgcaa tatgtcaaat caacttggaa    1380
ggaaagacct tctactccaa gaaggacaag cccctgtgca agagccatgc cttttcccac    1440
gtatgagcac ctcctcacac tactgccacc ctactctgcc agaagggtga taaaatgaga    1500
gagctctctc tccctcgacc tttctgggtg gggctggcag ccattgtcct agccttggct    1560
cctggccaga tcctgggct ccctcctcac agtcccttt cccacacttc ctccaccacc    1620
accaccgtca ctcacaggtg ctagcctcct agcccagtt cactctggtg tcacaataaa    1680
cctgtatgta gctgtg                                                  1696

<210> SEQ ID NO 3
<211> LENGTH: 260
<212> TYPE: DNA
```

```
<213> ORGANISM: Rattus norvegicus

<400> SEQUENCE: 3
ttctacatgg aggaggggc tccctactgc gagcgagatt acgagaagat gtttggcaca      60
aagtgtcgcg gctgtgactt caagatcgat gccggggacc gtttcctgga agccctgggt    120
ttcagctggc atgatacgtg ttttgtttgc gcaatatgtc aaatcaactt ggaaggaaag    180
accttctact ccaagaagga caagcccctg tgcaagagcc atgcttttc ccacgtatga     240 gcacctcctc acactactgc                                                260

<210> SEQ ID NO 4
<211> LENGTH: 16
<212> TYPE: DNA
<213> ORGANISM: Moloney murine leukemia virus

<400> SEQUENCE: 4 aagcttttt tttttg                                                      16

<210> SEQ ID NO 5
<211> LENGTH: 13
<212> TYPE: DNA
<213> ORGANISM: Moloney murine leukemia virus

<400> SEQUENCE: 5
aagcttggct atg                                                        13

<210> SEQ ID NO 6
<211> LENGTH: 223
<212> TYPE: DNA
<213> ORGANISM: Homo sapiens

<400> SEQUENCE: 6
atccttgctc acctcacggg caccgagttc atgcaagacc cggatgagga gcacctgaag     60
aaatcaagcc aggtgcccag gacagaagcc ccagccccag cctcatctac accccaggag    120
ccctggcctg gcctaccgc ccccagccct accagccgcc cgccctgggc tgtggaccct     180
gcgtttgccg agcgctatgc cccagacaaa accagcacag tgc                      223

<210> SEQ ID NO 7
<211> LENGTH: 717
<212> TYPE: DNA
<213> ORGANISM: Homo sapiens

<400> SEQUENCE: 7
atggattcct tcaaggtagt gctggagggg ccagcacctt ggggcttccg gctgcaaggg     60
ggcaaggact tcaatgtgcc cctctccatt tcccggctca ctcctggggg caaagcggcg    120
caggccggag tggccgtggg tgactgggtg ctgagcatcg atggcgagaa tgcgggtagc    180
ctcacacaca tcgaagctca gaacaagatc cgggcctgcg gggagcgcct cagcctgggc    240
ctcagcaggg cccagccggt tcagagcaaa ccgcagaagg cctccgcccc gccgcggac     300 cctccgcggt acacctttgc acccagcgtc tccctcaaca gacggcccg gccctttggg    360 gcgccccgc ccgctgacag cgccccgcaa cagaatggac agccgctccg accgctggtc     420
ccagatgcca gcaagcagcg gctgatggag aacacagagg actggcggcc gcggccgggg    480
acaggccagt cgcgttcctt ccgcatcctt gcccacctca caggcaccga gttcatgcaa    540
gacccggatg aggagcacct gaagaaatca agccaggtgc ccaggacaga agccccagcc    600
ccagcctcat ctacaccccca ggagccctgg cctggcccta ccgccccag ccctaccagc    660
```

```
cgcccgccct gggctgtgga ccctgcgttt gccgagcgct atgccccgga caaaacg       717

<210> SEQ ID NO 8
<211> LENGTH: 1488
<212> TYPE: DNA
<213> ORGANISM: Homo sapiens

<400> SEQUENCE: 8
atcgatggcg agaatgcggg tagcctcaca cacatcgaag ctcagaacaa gatccgggcc    60
tgcggggagc gcctcagcct gggcctcagc agggcccagc cggttcagag caaaccgcag   120
aaggcctccg ccccgccgc ggaccctccg cggtacacct ttgcacccag cgtctccctc    180
aacaagacgg cccggccctt tggggcgccc ccgcccgctg acagcgcccc gcaacagaat   240
ggacagccgc tccgaccgct ggtcccagat gccagcaagc agcggctgat ggagaacaca   300
gaggactggc ggccgcggcc ggggacaggc cagtcgcgtt ccttccgcat ccttgcccac   360
ctcacaggca ccgagttcat gcaagacccg gatgaggagc acctgaagaa atcaagccag   420
gtgcccagga cagaagcccc agccccagcc tcatctacac cccaggagcc ctggcctggc   480
cctaccgccc ccagccctac cagccgcccg ccctgagctg tggaccctgc gtttgccgag   540
cgctatgccc cggacaaaac gagcacagtg ctgaccccggc acagccagcc ggccacgccc   600
acgccgctgc agagccgcac ctccattgtg caggcagctg ccggagggt gccaggaggg   660 ggcagcaaca acggcaagac tcccgtgtgt caccagtgcc acaaggtcat ccggggccgc   720
tacctggtgg cgttgggcca cgcgtaccac ccggaggagt ttgtgtgtag ccagtgtggg   780
aaggtcctgg aagagggtgg cttctttgag gagaagggcg ccatcttctg cccaccatgc   840
tatgacgtgc gctatgcacc cagctgtgcc aagtgcaaga agaagattac aggcgagatc   900
atgcacgccc tgaagatgac ctggcacgtg cactgcttta cctgtgctgc ctgcaagacg   960
cccatccgga cagggccttt ctacatggag gagggcgtgc cctattgcga gcagactat   1020 gagaagatgt ttggcacgaa atgccatggc tgtgacttca agatcgacgc tggggaccgc   1080
ttcctggagg ccctgggctt cagctggcat gacacctgct tcgtctgtgc gatatgtcag   1140
atcaacctgg aaggaaagac cttctactcc aagaaggaca ggcctctctg caagagccat   1200
gccttctctc atgtgtgagc cccttctgcc cacagctgcc gcggtggccc ctagcctgag   1260
gggcctggag tcgtggccct gcatttctgg gtagggctgg caatggttgc cttaaccctg   1320
gctcctggcc cgagcctggg ctcccgggcc cctgcccacc cacccttatcc tcccacccca  1380 ctccctccac caccacagca caccggtgct ggccacacca gcccccttc acctccagtg   1440 ccacaataaa cctgtaccca gctgaattcc aaaaaatcca aaaaaaa                 1488

<210> SEQ ID NO 9
<211> LENGTH: 1644
<212> TYPE: DNA
<213> ORGANISM: Homo sapiens

<400> SEQUENCE: 9
atggattcct tcaaggtagt gctggagggg ccagcaccct ggggcttccg gctgcaaggg   60
ggcaaggact tcaatgtgcc cctctccatt tcccggctca ctcctggggg caaagcggcg   120
caggccggag tggccgtggg tgactgggtg ctgagcatcg atggcgagaa tgcgggtagc   180
ctcacacaca tcgaagctca gaacaagatc cgggcctgcg gggagcgcct cagcctgggc   240
ctcagcaggg cccagccggt tcagagcaaa ccgcagaagg cctccgcccc cgccgcggac   300
```

-continued

```
cctccgcggt acacctttgc acccagcgtc tccctcaaca agacggcccg gcccttnggg    360
gcgcccccgc ccgctgacag cgccccgcaa cagaatggac agccgctccg accgctggtc    420
ccagatgcca gcaagcagcg gctgatggag aacacagagg actggcggcc gcggccgggg    480
acaggccagt cgcgttcctt ccgcatcctt gcccacctca caggcaccga gttcatgcaa    540
gacccggatg aggagcacct gaagaaatca agccaggtgc ccaggacaga agccccagcc    600
ccagcctcat ctacacccca ggagccctgg cctggcccta ccgcccccag ccctaccagc    660
cgcccgccct gggctgtgga ccctgcgttt gccgagcgct atgccccgga caaaacgagc    720
acagtgctga cccggcacag ccagccgcc acgcccacgc cgctgcagag ccgcacctcc    780
attgtgcagg cagctgccgg aggggtgcca ggaggggca gcaacaacgg caagactccc    840
gtgtgtcacc agtgccacaa ggtcatccgg ggccgctacc tggtggcgtt gggcacgcg    900
taccacccgg aggagtttgt gtgtagccag tgtgggaagg tcctggaaga gggtggcttc    960
tttgaggaga agggcgccat cttctgccca ccatgctatg acgtgcgcta tgcacccagc   1020
tgtgccaagt gcaagaagaa gattacaggc gagatcatgc acgccctgaa gatgacctgg   1080
cacgtgcact gctttacctg tgctgcctgc aagacgccca tccggaacag ggccttctac   1140
atggaggagg gcgtgcccta ttgcgagcga gactatgaga agatgtttgg cacgaaatgc   1200
catggctgtg acttcaagat cgacgctggg gaccgcttcc tggaggccct gggcttcagc   1260
tggcatgaca cctgcttcgt ctgtgcgata tgtcagatca acctggaagg aaagaccttc   1320
tactccaaga aggacaggcc tctctgcaag agccatgcct tctctcatgt gtgagcccct   1380
tctgcccaca gctgccgcgg tggcccctag cctgagggc ctggagtcgt ggccctgcat   1440
ttctgggtag ggctggcaat ggttgccta accctggctc ctggcccgag cctgggctcc   1500
cgggcccctg cccacccacc ttatcctccc accccactcc ctccaccacc acagcacacc   1560
ggtgctggcc acaccagccc cctttcacct ccagtgccac aataaacctg tacccagctg   1620
aattccaaaa aatccaaaaa aaaa                                           1644
```

<210> SEQ ID NO 10
<211> LENGTH: 457
<212> TYPE: PRT
<213> ORGANISM: Homo sapiens

<400> SEQUENCE: 10

```
Met Asp Ser Phe Lys Val Val Leu Glu Gly Pro Ala Pro Trp Gly Phe
 1               5                  10                  15
Arg Leu Gln Gly Gly Lys Asp Phe Asn Val Pro Leu Ser Ile Ser Arg
                20                  25                  30
Leu Thr Pro Gly Gly Lys Ala Ala Gln Ala Gly Val Ala Val Gly Asp
            35                  40                  45
Trp Val Leu Ser Ile Asp Gly Glu Asn Ala Gly Ser Leu Thr His Ile
        50                  55                  60
Glu Ala Gln Asn Lys Ile Arg Ala Cys Gly Glu Arg Leu Ser Leu Gly
 65                  70                  75                  80
Leu Ser Arg Ala Gln Pro Val Gln Ser Lys Pro Gln Lys Ala Ser Ala
                85                  90                  95
Pro Ala Ala Asp Pro Pro Arg Tyr Thr Phe Ala Pro Ser Val Ser Leu
                100                 105                 110
Asn Lys Thr Ala Arg Pro Phe Gly Ala Pro Pro Ala Asp Ser Ala
            115                 120                 125
Pro Gln Gln Asn Gly Gln Pro Leu Arg Pro Leu Val Pro Asp Ala Ser
```

```
            130                 135                 140
Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu His Leu Lys Lys Ser Ser Gln
            180                 185                 190

Val Pro Arg Thr Glu Ala Pro Ala Pro Ala Ser Ser Thr Pro Gln Glu
                195                 200                 205

Pro Trp Pro Gly Pro Thr Ala Pro Ser Pro Thr Ser Arg Pro Pro Trp
210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Ser Arg Thr Ser Ile Val Gln Ala Ala Gly Gly Val Pro Gly Gly
                260                 265                 270

Gly Ser Asn Asn Gly Lys Thr Pro Val Cys His Gln Cys His Lys Val
        275                 280                 285

Ile Arg Gly Arg Tyr Leu Val Ala Leu Gly His Ala Tyr His Pro Glu
    290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
                325                 330                 335

Tyr Ala Pro Ser Cys Ala Lys Cys Lys Lys Ile Thr Gly Glu Ile
                340                 345                 350

Met His Ala Leu Lys Met Thr Trp His Val His Cys Phe Thr Cys Ala
            355                 360                 365

Ala Cys Lys Thr Pro Ile Arg Asn Arg Ala Phe Tyr Met Glu Glu Gly
        370                 375                 380

Val Pro Tyr Cys Glu Arg Asp Tyr Glu Lys Met Phe Gly Thr Lys Cys
385                 390                 395                 400

His Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Lys Asp Arg Pro Leu
        435                 440                 445

Cys Lys Ser His Ala Phe Ser His Val
    450                 455

<210> SEQ ID NO 11
<211> LENGTH: 22
<212> TYPE: DNA
<213> ORGANISM: Rattus norvegicus

<400> SEQUENCE: 11
gccagggttt tcccagtcac ga                                              22

<210> SEQ ID NO 12
<211> LENGTH: 22
<212> TYPE: DNA
<213> ORGANISM: Rattus norvegicus

<400> SEQUENCE: 12
```

```
gccagggttt tcccagtcac ga                                              22

<210> SEQ ID NO 13
<211> LENGTH: 22
<212> TYPE: DNA
<213> ORGANISM: Homo sapiens

<400> SEQUENCE: 13
tcttagcaga gcccagcctg ct                                              22

<210> SEQ ID NO 14
<211> LENGTH: 22
<212> TYPE: DNA
<213> ORGANISM: Homo sapiens

<400> SEQUENCE: 14
gcatgaactc tgtgcccgtg ag                                              22

<210> SEQ ID NO 15
<211> LENGTH: 20
<212> TYPE: DNA
<213> ORGANISM: Rattus norvegicus

<400> SEQUENCE: 15
atccttgctc acctcacggg                                                 20

<210> SEQ ID NO 16
<211> LENGTH: 22
<212> TYPE: DNA
<213> ORGANISM: Rattus norvegicus

<400> SEQUENCE: 16
gcactgtgct ggttttgtct gg                                              22

<210> SEQ ID NO 17
<211> LENGTH: 23
<212> TYPE: DNA
<213> ORGANISM: Homo sapiens

<400> SEQUENCE: 17
catggattcc ttcaaggtag tgc                                             23

<210> SEQ ID NO 18
<211> LENGTH: 20
<212> TYPE: DNA
<213> ORGANISM: Homo sapiens

<400> SEQUENCE: 18
gttttgtctg gggcagagcg                                                 20

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ctaatacgac tcactatagg gctcgagcgg ccgcccgggc aggt                      44

<210> SEQ ID NO 20
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccatcctaat acgactcact atagggc                                              27

<210> SEQ ID NO 21
<211> LENGTH: 765
<212> TYPE: DNA
<213> ORGANISM: Homo sapiens

<400> SEQUENCE: 21
ccgttgtttg taaaacgacg cagagcagcg ccctggccgg gccaagcagg agccggcatc          60
atggattcct tcaaggtagt gctggagggg ccagcacctt ggggcttccg gctgcaaggg         120
ggcaaggact tcaatgtgcc ctcctccatt tcccggctca cctctggggg caaggccgtg         180
caggccggag tggccgtaag tgactgggtg ctgagcatcg atggcgagaa tgcgggtagc         240
ctcacacaca tcgaagctca gaacaagatc cgggcctgcg gggagcgcct cagcctgggc         300
ctcaacaggg cccagccggt tcagaacaaa ccgcaaaagg cctccgcccc cgccgcggac         360
cctccgcggt acacctttgc accaagcgtc tccctcaaca agacgcccg gcccttgggg         420 gcgcccccgc ccgctgacag cgccccgcag cagaatggac agccgctccg accgctggtc         480
ccagatgcca gcaagcagcg gctgatggag aacacagagg actggcggcc gcggccgggg         540
acaggccagt gccgttcctt tcgcatcctt gctcaccta caggcaccga gttcatgcaa         600
gacccggatg aggagcacct gaagaaatca agccaggtgc ccaggacaga gccccagcc         660 ccagcctcat ctacacccca ggagccctgg cctggcccta ccgccccag ccctaccagc          720 cgcccgccct gggctgtgga ccctgcgttt gccgagcgct atgcc                          765

<210> SEQ ID NO 22
<211> LENGTH: 1689
<212> TYPE: DNA
<213> ORGANISM: Homo sapiens

<400> SEQUENCE: 22
cgacgcagag cagcgccctg gccgggccaa gcaggagccg gcatcatgga ttccttcaag          60
gtagtgctgg aggggccagc accttggggc ttccggctgc aaggggcaa ggacttcaat         120 gtgcccctct ccatttcccg gctcactcct ggggcaaag cggcgcaggc cggagtggcc         180
gtgggtgact gggtgctgag catcgatggc gagaatgcgg gtagcctcac acacatcgaa         240
gctcagaaca agatccgggc ctgcggggag cgcctcagcc tgggcctcag cagggcccag         300
ccggttcaga gcaaaccgca gaaggcctcc gccccgccg cggaccctcc gcggtacacc          360
tttgcaccca gcgtctccct caacaagacg gcccggccct tggggcgcc ccgcccgct           420 gacagcgccc cgcaacagaa tggacagccg ctccgaccgc tggtcccaga tgccagcaag         480
cagcggctga tggagaacac agaggactgg cggccgcggc cggggacagg ccagtcgcgt         540
tccttccgca tccttgccca cctcacaggc accgagttca tgcaagaccc ggatgaggag         600
cacctgaaga aatcaagcca ggtgcccagg acagaagccc agccccagc ctcatctaca          660 ccccaggagc cctggcctgg ccctaccgcc ccagcccta ccagccgccc gccctgggct          720
gtggaccctg cgtttgccga gcgctatgcc ccggacaaaa cgagcacagt gctgacccgg         780
cacagccagc cggccacgcc cacgccgctg cagagccgca cctccattgt gcaggcagct         840
```

-continued

```
gccggagggg tgccaggagg gggcagcaac aacggcaaga ctcccgtgtg tcaccagtgc      900
cacaaggtca tccggggccg ctacctggtg gcgttgggcc acgcgtacca cccggaggag      960
tttgtgtgta gccagtgtgg gaaggtcctg aagagggtg gcttctttga ggagaagggc      1020
gccatcttct gcccaccatg ctatgacgtg cgctatgcac ccagctgtgc caagtgcaag      1080
aagaagatta caggcgagat catgcacgcc ctgaagatga cctggcacgt gcactgcttt      1140
acctgtgctg cctgcaagac gcccatccgg aacagggcct tctacatgga ggagggcgtg      1200
ccctattgcg agcgagacta tgagaagatg tttggcacga atgccatgg ctgtgacttc      1260 aagatcgacg ctggggaccg cttcctggag gccctgggct tcagctggca tgacacctgc      1320
ttcgtctgtg cgatatgtca gatcaacctg gaaggaaaga ccttctactc caagaaggac      1380
aggcctctct gcaagagcca tgccttctct catgtgtgag ccccttctgc ccacagctgc      1440
cgcggtggcc cctagcctga ggggcctgga gtcgtggccc tgcatttctg ggtagggctg      1500
gcaatggttg ccttaaccct ggctcctggc ccgagcctgg gctcccgggc cctgcccac      1560 ccaccttatc ctcccacccc actccctcca ccaccacagc acaccggtgc tggccacacc      1620
agcccccttt cacctccagt gccacaataa acctgtaccc agctgaattc caaaaaatcc      1680
aaaaaaaaa                                                              1689
```

<210> SEQ ID NO 23
<211> LENGTH: 22
<212> TYPE: DNA
<213> ORGANISM: Homo sapiens

<400> SEQUENCE: 23
gcactgtgct cgttttgtcc gg                                               22

<210> SEQ ID NO 24
<211> LENGTH: 21
<212> TYPE: DNA
<213> ORGANISM: Homo sapiens

<400> SEQUENCE: 24
tccttgctca cctcacgggc a                                                21

<210> SEQ ID NO 25
<211> LENGTH: 30
<212> TYPE: DNA
<213> ORGANISM: Homo sapiens

<400> SEQUENCE: 25
tcctcatccg ggtcttgcat gaactcggtg                                       30

<210> SEQ ID NO 26
<211> LENGTH: 28
<212> TYPE: DNA
<213> ORGANISM: Homo sapiens

<400> SEQUENCE: 26
gcccccgccc gctgacagcg ccccgcaa                                         28

<210> SEQ ID NO 27
<211> LENGTH: 24
<212> TYPE: DNA
<213> ORGANISM: Homo sapiens

<400> SEQUENCE: 27

-continued

| | |
|---|---|
| tccttgctca cctcacgggc accg | 24 |

<210> SEQ ID NO 28
<211> LENGTH: 22
<212> TYPE: DNA
<213> ORGANISM: Homo sapiens

<400> SEQUENCE: 28

| | |
|---|---|
| gtaatacgac tcactatagg gc | 22 |

<210> SEQ ID NO 29
<211> LENGTH: 23
<212> TYPE: DNA
<213> ORGANISM: Rattus norvegicus

<400> SEQUENCE: 29

| | |
|---|---|
| gcggctgatg gagaatactg aag | 23 |

<210> SEQ ID NO 30
<211> LENGTH: 23
<212> TYPE: DNA
<213> ORGANISM: Rattus norvegicus

<400> SEQUENCE: 30

| | |
|---|---|
| atcttgtggc actggtggca tac | 23 |

<210> SEQ ID NO 31
<211> LENGTH: 22
<212> TYPE: DNA
<213> ORGANISM: Rattus norvegicus

<400> SEQUENCE: 31

| | |
|---|---|
| tgtgtcgggt cagcactgtg ct | 22 |

<210> SEQ ID NO 32
<211> LENGTH: 1620
<212> TYPE: DNA
<213> ORGANISM: Homo sapiens

<400> SEQUENCE: 32

| | |
|---|---|
| atggattcct tcaaggtagt gctggagggg ccagcaccctt ggggcttccg gctgcaaggg | 60 |
| ggcaaggact tcaatgtgcc cctctccatt tcccggctca ctcctggggg caaagcggcg | 120 |
| caggccggag tggccgtggg tgactgggtg ctgagcatcg atggcgagaa tgcgggtagc | 180 |
| ctcacacaca tcgaagctca gaacaagatc cgggcctgcg gggagcgcct cagcctgggc | 240 |
| ctcagcaggg cccagccggt tcagagcaaa ccgcagaagg cctccgcccc cgccgcggac | 300 |
| cctccgcggt acacctttgc acccagcgtc tccctcaaca gacgcccg gccctttggg | 360 |
| gcgcccccgc ccgctgacag cgccccgcaa cagaatggac agccgctccg accgctggtc | 420 |
| ccagatgcca gcaagcagcg gctgatggag aacacagagg actggcggcc gcggccgggg | 480 |
| acaggccagt cgcgttcctt ccgcatcctt gcccacctca caggcaccga gttcatgcaa | 540 |
| gacccggatg aggagcacct gaagaaatca agccaggtgc ccaggacaga agccccagcc | 600 |
| ccagcctcat ctacaccccca ggagccctgg cctggcccta ccgcccccag ccctaccagc | 660 |
| cgccgccct gagctgtgga ccctgcgttt gccgagcgct atgcccgga caaaacgagc | 720 |
| acagtgctga cccggcacag ccagccggcc acgcccacgc cgctgcagag ccgcacctcc | 780 |
| attgtgcagg cagctgccgg aggggtgcca ggagggggca gcaacaacgg caagactccc | 840 |
| gtgtgtcacc agtgccacaa ggtcatccgg ggccgctacc tggtggcgtt gggccacgcg | 900 |

```
taccacccgg aggagtttgt gtgtagccag tgtgggaagg tcctggaaga gggtggcttc    960
tttgaggaga agggcgccat cttctgccca ccatgctatg acgtgcgcta tgcacccagc   1020
tgtgccaagt gcaagaagaa gattacaggc gagatcatgc acgccctgaa gatgacctgg   1080
cacgtgcact gctttacctg tgctgcctgc aagacgccca tccggaacag ggccttctac   1140
atggaggagg cgtgcccta ttgcgagcga gactatgaga gatgtttgg cacgaaatgc     1200 catggctgtg acttcaagat cgacgctggg gaccgcttcc tggaggccct gggcttcagc   1260
tggcatgaca cctgcttcgt ctgtgcgata tgtcagatca acctggaagg aaagaccttc   1320
tactccaaga aggacaggcc tctctgcaag agccatgcct tctctcatgt gtgagcccct   1380
tctgcccaca gctgccgcgg tggccctag cctgaggggc ctggagtcgt ggccctgcat    1440
ttctgggtag ggctggcaat ggttgcctta accctggctc ctggcccgag cctgggctcc   1500
cgggcccctg cccacccacc ttatcctccc accccactcc ctccaccacc acagcacacc   1560
ggtgctggcc acaccagccc cctttcacct ccagtgccac aataaacctg tacccagctg   1620
```

<210> SEQ ID NO 33
<211> LENGTH: 1665
<212> TYPE: DNA
<213> ORGANISM: Homo sapiens

<400> SEQUENCE: 33

```
cgacgcagag cagcgccctg ccgggccaa gcaggagccg gcatcatgga ttccttcaag      60
gtagtgctgg aggggccagc accttgggggc ttccggctgc aaggggggcaa ggacttcaat   120 gtgcccctct ccatttcccg gctcactcct gggggcaaag cggcgcaggc cggagtggcc    180
gtgggtgact gggtgctgag catcgatggc gagaatgcgg gtagcctcac acacatcgaa    240
gctcagaaca agatccgggc ctgcggggag cgcctcagcc tgggcctcag cagggcccag    300
ccggttcaga gcaaaccgca gaaggcctcc gcccccgccg cggaccctcc gcggtacacc    360
tttgcaccca gcgtctccct caacaagacg gcccggccct ttggggcgcc cccgcccgct    420
gacagcgccc cgcaacagaa tggacagccg ctccgaccgc tggtcccaga tgccagcaag    480
cagcggctga tggagaacac agaggactgg cggccgcggc cggggacagg ccagtcgcgt    540
tccttccgca tccttgccca cctcacaggc accgagttca tgcaagaccc ggatgaggag    600
cacctgaaga aatcaagcca ggtgcccagg acagaagccc cagccccagc ctcatctaca    660
ccccaggagc cctggcctgg ccctaccgcc ccagccccta ccagccgccc gccctgagct    720
gtggaccctg cgtttgccga gcgctatgcc ccggacaaaa cgagcacagt gctgacccgg    780
cacagccagc cggccacgcc cacgccgctg cagagccgca cctccattgt gcaggcagct    840
gccggagggg tgccaggagg gggcagcaac aacggcaaga ctcccgtgtg tcaccagtgc    900
cacaaggtca tccggggccg ctacctggtg gcgttgggcc acgcgtacca cccggaggag    960
tttgtgtgta gccagtgtgg aaggtcctg gaagagggtg gcttctttga ggagaagggc     1020
gccatcttct gccaccatg ctatgacgtg cgctatgcac ccagctgtgc caagtgcaag    1080
aagaagatta caggcgagat catgcacgcc ctgaagatga cctggcacgt gcactgcttt   1140
acctgtgctg cctgcaagac gcccatccgg aacaggcct tctacatgga ggagggcgtg    1200
ccctattgcg agcgagacta tgagaagatg tttggcacga aatgccatgg ctgtgacttc    1260
aagatcgacg ctggggaccg cttcctggag gccctgggct tcagctggca tgacacctgc    1320
ttcgtctgtg cgatatgtca gatcaacctg gaaggaaaga ccttctactc caagaaggac   1380
```

-continued

```
aggcctctct gcaagagcca tgccttctct catgtgtgag cccccttctgc ccacagctgc    1440 cgcggtggcc cctagcctga ggggcctgga gtcgtggccc tgcatttctg ggtagggctg    1500
gcaatggttg ccttaaccct ggctcctggc ccgagcctgg gctccgggcc cctgcccac    1560 ccaccttatc ctcccacccc actccctcca ccaccacagc acaccggtgc tggccacacc    1620 agccccttt cacctccagt gccacaataa acctgtaccc agctg                      1665
```

<210> SEQ ID NO 34
<211> LENGTH: 223
<212> TYPE: PRT
<213> ORGANISM: Homo sapiens

<400> SEQUENCE: 34

```
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Pro Ala Asp Ser Ala
        115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu His Leu Lys Lys Ser Ser Gln
            180                 185                 190

Val Pro Arg Thr Glu Ala Pro Ala Pro Ala Ser Ser Thr Pro Gln Glu
        195                 200                 205

Pro Trp Pro Gly Pro Thr Ala Pro Ser Pro Thr Ser Arg Pro Pro
    210                 215                 220
```

<210> SEQ ID NO 35
<211> LENGTH: 20
<212> TYPE: DNA
<213> ORGANISM: Homo sapiens

<400> SEQUENCE: 35

```
gagccggcat catggattcc                                                    20
```

<210> SEQ ID NO 36
<211> LENGTH: 20
<212> TYPE: DNA
<213> ORGANISM: Homo sapiens

<400> SEQUENCE: 36

```
gctgcctgca caatggaggt                                                    20
```

<210> SEQ ID NO 37
<211> LENGTH: 1456
<212> TYPE: DNA
<213> ORGANISM: Homo sapiens

<400> SEQUENCE: 37

```
cgacgcagag cagcgccctg gccgggccaa gcaggagccg gcatcatgga ttccttcaag      60
gtagtgctgg aggggccagc accttggggc ttccggctgc aaggggggcaa ggacttcaat    120
gtgcccctct ccatttcccg gctcactcct gggggcaaag cggcgcaggc cggagtggcc    180
gtgggtgact gggtgctgag catcgatggc gagaatgcgg gtagcctcac acacatcgaa    240
gctcagaaca agatccgggc ctgcggggag cgcctcagcc tgggcctcag cagggcccag    300
ccggttcaga gcaaaccgca gaaggtgcag acccctgaca acagccgct ccgaccgctg     360
gtcccagatg ccagcaagca gcggctgatg gagaacacag aggactggcg gccgcggccg    420
gggacaggcc agtcgcgttc cttccgcatc cttgcccacc tcacaggcac cgagttcatg    480
caagacccgg atgaggagca cctgaagaaa tcaagccagg tgcccaggac agaagcccca    540
gccccagcct catctacacc ccaggagccc tggcctggcc ctaccgcccc cagccctacc    600
agccgcccgc cctgggctgt ggaccctgcg tttgccgagc gctatgcccc ggacaaaacg    660
agcacagtgc tgacccggca cagccagccg gccacgccca cgccgctgca gagccgcacc    720
tccattgtgc aggcagctgc cggagggtg ccaggagggg gcagcaacaa cggcaagact     780
cccgtgtgtc accagtgcca caaggtcatc cggggccgct acctggtggc gttgggccac    840
gcgtaccacc ggaggagtt tgtgtgtagc cagtgtggga aggtcctgga gagggtggc     900
ttctttgagg agaagggcgc catcttctgc ccaccatgct atgacgtgcg ctatgcaccc    960
agctgtgcca agtgcaagaa gaagattaca ggcgagatca tgcacgccct gaagatgacc   1020
tggcacgtgc actgctttac ctgtgctgcc tgcaagacgc ccatccggaa cagggccttc   1080
tacatggagg agggcgtgcc ctattgcgag cgagactatg agaagatgtt tggcacgaaa   1140
tgccatggct gtgacttcaa gatcgacgct ggggaccgct tcctggaggc cctgggcttc   1200
agctggcatg acacctgctt cgtctgtgcg atatgtcaga tcaacctgga aggaaagacc   1260
ttctactcca gaaggacag gcctctctgc aagagccatg ccttctctca tgtgtgagcc   1320
ccttctgccc acagctgccg cggtggcccc tagcctgagg ggcctggagt cgtggccctg   1380
catttctggg tagggctggc aatggttgcc ttaaccctgg ctcctggccc gagcctgggc   1440
tcccgggccc tgccca                                                    1456
```

<210> SEQ ID NO 38
<211> LENGTH: 423
<212> TYPE: PRT
<213> ORGANISM: Homo sapiens

<400> SEQUENCE: 38

```
Met Asp Ser Phe Lys Val Val Leu Glu Gly Pro Ala Pro Trp Gly Phe
 1               5                  10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60
```

-continued

```
Glu Ala Gln Asn Lys Ile Arg Ala Cys Gly Glu Arg Leu Ser Leu Gly
 65                  70                  75                  80

Leu Ser Arg Ala Gln Pro Val Gln Asn Lys Pro Gln Lys Val Gln Thr
                 85                  90                  95

Pro Asp Lys Gln Pro Leu Arg Pro Leu Val Pro Asp Ala Ser Lys Gln
            100                 105                 110

Arg Leu Met Glu Asn Thr Glu Asp Trp Arg Pro Arg Gly Thr Gly
        115                 120                 125

Gln Ser Arg Ser Phe Arg Ile Leu Ala His Leu Thr Gly Thr Glu Phe
    130                 135                 140

Met Gln Asp Pro Asp Glu Glu His Leu Lys Lys Ser Ser Gln Val Pro
145                 150                 155                 160

Arg Thr Glu Ala Pro Ala Pro Ala Ser Ser Thr Pro Gln Glu Pro Trp
                165                 170                 175

Pro Gly Pro Thr Ala Pro Ser Pro Thr Ser Arg Pro Pro Trp Ala Val
            180                 185                 190

Asp Pro Ala Phe Ala Glu Arg Tyr Ala Pro Asp Lys Thr Ser Thr Val
        195                 200                 205

Leu Thr Arg His Ser Gln Pro Ala Thr Pro Thr Pro Leu Gln Ser Arg
    210                 215                 220

Thr Ser Ile Val Gln Ala Ala Gly Val Pro Gly Gly Gly Ser
225                 230                 235                 240

Asn Asn Gly Lys Thr Pro Val Cys His Gln Cys His Gln Val Ile Arg
                245                 250                 255

Ala Arg Tyr Leu Val Ala Leu Gly His Ala Tyr His Pro Glu Glu Phe
            260                 265                 270

Val Cys Ser Gln Cys Gly Lys Val Leu Glu Glu Gly Gly Phe Phe Glu
        275                 280                 285

Glu Lys Gly Ala Ile Phe Cys Pro Pro Cys Tyr Asp Val Arg Tyr Ala
    290                 295                 300

Pro Ser Cys Ala Lys Cys Lys Lys Ile Thr Gly Glu Ile Met His
305                 310                 315                 320

Ala Leu Lys Met Thr Trp His Val Leu Cys Phe Thr Cys Ala Ala Cys
                325                 330                 335

Lys Thr Pro Ile Arg Asn Arg Ala Phe Tyr Met Glu Glu Gly Val Pro
            340                 345                 350

Tyr Cys Glu Arg Asp Tyr Glu Lys Met Phe Gly Thr Lys Cys Gln Trp
        355                 360                 365

Cys Asp Phe Lys Ile Asp Ala Gly Asp Arg Phe Leu Glu Ala Leu Gly
    370                 375                 380

Phe Ser Trp His Asp Thr Cys Phe Val Cys Ala Ile Cys Gln Ile Asn
385                 390                 395                 400

Leu Glu Gly Lys Thr Phe Tyr Ser Lys Lys Asp Arg Pro Leu Cys Lys
                405                 410                 415

Ser His Ala Phe Ser His Val
            420
```

<210> SEQ ID NO 39
<211> LENGTH: 1575
<212> TYPE: DNA
<213> ORGANISM: Homo sapiens

<400> SEQUENCE: 39
cgacgcagag cagcgccctg gccgggccaa gcaggagccg gcatcatgga ttccttcaag    60

-continued

```
gtagtgctgg aggggccagc accttggggc ttccggctgc aagggggcaa ggacttcaat    120
gtgcccctct ccatttcccg gctcactcct ggggcaaag cggcgcaggc cggagtggcc    180
gtgggtgact gggtgctgag catcgatggc gagaatgcgg gtagcctcac acacatcgaa    240
gctcagaaca agatccgggc ctgcggggag cgcctcagcc tgggcctcag cagggcccag    300
ccggttcaga gcaaaccgca gaaggcctcc gcccccgccg cggacccctcc gcggtacacc    360
tttgcaccca gcgtctccct caacaagacg gcccggccct tggggcgcc cccgcccgct    420
gacagcgccc cgcaacagaa tgggtgcaga ccctgacaa acagccgctc cgaccgctgg    480
tcccagatgc cagcaagcag cggctgatgg agaacacaga ggactggcgg ccgcggccgg    540
ggacaggcca gtcgcgttcc ttccgcatcc ttgcccacct cacaggcacc gagttcatgc    600
aagacccgga tgaggagcac ctgaagaaat caagccaggt gcccaggaca gaagcccag    660
ccccagcctc atctacaccc caggagcct ggcctggccc taccgccccc agccctacca    720
gccgcccgcc ctgggctgtg gaccctgcgt ttgccgagcg ctatgccccg gacaaaacga    780
gcacagtgct gacccggcac agccagccgg ccacgcccac gccgctgcag agccgcacct    840
ccattgtgca ggcagctgcc ggaggggtgc caggaggggg cagcaacaac ggcaagactc    900
ccgtgtgtca ccagtgccac aaggtcatcc ggggccgcta cctggtggcg ttgggccacg    960
cgtaccaccc ggaggagttt gtgtgtagcc agtgtgggaa ggtcctggaa gagggtggct   1020
tctttgagga aagggcgcc atcttctgcc caccatgcta tgacgtgcgc tatgcaccca   1080
gctgtgccaa gtgcaagaag aagattacag gcgagatcat gcacgccctg aagatgacct   1140
ggcacgtgca ctgctttacc tgtgctgcct gcaagacgcc catccggaac agggccttct   1200
acatggagga gggcgtgccc tattgcgagc gagactatga aagatgtttt ggcacgaaat   1260
gccatggctg tgacttcaag atcgacgctg gggaccgctt cctggaggcc ctgggcttca   1320
gctggcatga cacctgcttc gtctgtgcga tatgtcagat caacctggaa ggaaagacct   1380
tctactccaa gaaggacagg cctctctgca agagccatgc cttctctcat gtgtgagccc   1440
cttctgccca cagctgccgc ggtggcccct agcctgaggg gcctggagtc gtggccctgc   1500
atttctgggt agggctggca atggttgcct taaccctggc tcctggcccg agcctgggct   1560
cccgggccct gccca                                                   1575
```

<210> SEQ ID NO 40
<211> LENGTH: 153
<212> TYPE: PRT
<213> ORGANISM: Homo sapiens

<400> SEQUENCE: 40

```
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Pro Pro Arg Tyr Thr Phe Ala Pro Ser Val Ser Leu
```

```
                    100                 105                 110
Asn Lys Thr Ala Arg Pro Phe Gly Ala Pro Pro Ala Asp Ser Ala
        115                 120                 125

Pro Gln Gln Asn Gly Cys Arg Pro Leu Thr Asn Ser Arg Ser Asp Arg
    130                 135                 140

Trp Ser Gln Met Pro Ala Ser Ser Gly
145                 150

<210> SEQ ID NO 41
<211> LENGTH: 24740
<212> TYPE: DNA
<213> ORGANISM: Homo sapiens
<220> FEATURE:
<221> NAME/KEY: modified_base
<222> LOCATION: (1)..(6)
<223> OTHER INFORMATION: a, c, g, t, unknown or other
<220> FEATURE:
<221> NAME/KEY: modified_base
<222> LOCATION: (8101)
<223> OTHER INFORMATION: a, c, g, t, unknown or other

<400> SEQUENCE: 41
nnnnnntgta ttttatcata ttttaaaaat caaaaaacaa aaggcagttg aggttaggca      60
tggaggttcg tgcctgtaat cccagcactt tgggaagccg aagcacgtgg atcacctgag     120
gtcaggagtt cgagaccagc ctgcccaata tggtaaaacc ctgtctctac taaaaataca     180
aaaaattagc caggcatggt ggtgggcacc tgtaatccca gctacttggg agactgaggc     240
aggagaatca cttaaacccg ggaggcgggc tgggcgcggt ggctcatgcc tgtaatccca     300
gcactttggg aggccgagac aggcggatca tgaggtcagg agatcgagat catcctggct     360
aacatggtga acccccatct ctactaaaaa tacaaaaaaa attagccagg cctggtggcg     420
ggcacctgta gtcccagcta cttgggaggc tgaggcagga gaatggcgtg aacctgggag     480
gcggcgttgc agtgagccaa gatcgcgcca ctgcactcca gcctgggcga caagagtgag     540
actccatctt aaagaaaaaa aacaaacccg ggaggcggaa attgcagtca gccgagatct     600
cgccattgca ctcaagtatg ggtgacagag caagactcca tgtcaaaaaa aaaggcagtt     660
gacaggagca aggagcctgg tgaggaagct gtggcatttg acccggctgt gttgctatgg     720
gccagggtgg tgctagtaga ggagctgagt gggaaagagc acaggggaca tgctgaaggc     780
ctgggtgtgg ggatgaggca gagattgggg gcaccttgca gggtcatagc aggtggctgt     840
ggtgagatgg aggaagacac ctggggtact gctctaggct gtcagacata cagaagctgg     900
cccagccaag cccaggggct gcaagggaca tccttttgtg tccccagtga tctgcagctc     960
tcagacaccc tcaagcacag tgcctcttgc ccagcccagc actctcagtg gggagccagg    1020
tgggagaaca ggctcggaag gggacctagg cttatgcagc gagccgggca aagctggaac    1080
tggagcccag gccctggat gccccctggc ttgtggagtt ctgggatact gaggggaggg     1140
gacagggcat gggagtgcgg tgctctcacc tttgacttga actcattccc caggggacag    1200
gggaggcctc ctcaggatcc acagatgccc agtctcccaa gaggggcctg gtccccatgg    1260
aggaaaactc catctactcc tcctggcagg aaggtaagtt ggaggacgtg caagggcagc    1320
ctcagccccc cacacccagg gctgggtctt tttgggactg acggagctgt cctgccacc     1380 tgccacagtg ggcgagtttc ccgtggtggt gcagaggact gaggccgcca cccgctgcca    1440
gctgaagggg ccggccctgc tggtgctggg cccagacgcc atccagctga gggaggccaa    1500
ggcacccagg ccctctacag ctggccctac cacttcctgc gcaagttcgg ctccgacaag    1560
```

```
gtgaggtgca ggggtgggaa agggtgaggg gctgacagcc tggaccctcc tgctaatccc    1620
cacccgtgtg ccctgtgccc agggcgtgtt ctcctttgag gccggccgtc gctgccactc    1680
gggtgagggc ctcttttgcct tcagcacccc ctgtgcccct gacctgtgca gggctgtggc   1740
cggggccatc gccgccagcg ggagcggctg ccagagctga ccaggcccca gccctgcccc    1800
ctgccacggg ccacctctct gccctccctg acaccccg gagagcttcg ggagatgcca      1860
ccaggacctg agccacccac gtccaggaaa atgcacctgg ccgagcccgg accccagagc    1920
ctgccgctac tgctaggccc ggagcccaac gatctggcgt ccgggctcta cgcttcagtg    1980
tgcaagcgtg ccagtgggcc cccaggcaat gagcacctct atgagaacct gtgtgtgctg    2040
gaggccagcc ccacgctgca cggtgggaa cctgagccgc acgagggccc cggcagccgc     2100
agccccacaa ccagtcccat ctaccacaac ggccaggact tgagctggcc cggcccggcc   2160
aacgacagta ccctggaggc ccagtaccgg cggctgctgg agctggatca ggtggagggc    2220
acaggccgcc ctgaccctca ggcaggtttc aaggccaagc tggtgaccct gctgagtcgt    2280
gagcggagga agggcccagc cccttgtgac cggccctgaa cgcccagcag agtggtggcc    2340
agaggggaga ggtgctcccc ctgggacagg agggtgggct ggtgggcaaa cattgggccc    2400
atgcagacac acgcctgtgt ccaccctggc ctgcaggaac aaggcaggcc gcctgtggag    2460
gacctcagcc ctgccctgcc ctcctcatga atagtgtgca gactcacaga taataaagct    2520
cagagcagct cccggcaggg gcactcacgg cacacgcccc tgcccacgtt cattgcggcc    2580
aacacaagca ccctgtgccg gttccagggg acaggtgac ctgggcctta cctgccaccc     2640
gtgggctcaa acccactgca gcagacagac gggatggaaa tcattaggac tccatgttgc    2700
tctgcacggc cgagtgacac gaagaggcag gcggagggga ctgtgaggct tacttgtcag    2760
actcaggaag gagcaacatg agggcccaac tggagacccg gaggcccgag ctgggaggag    2820
gcagtggggg cggggtgcag gtggaaggga tttcagagac ccctcgtcc aaaacacttg     2880
ttccctgctg aaactccaac aatttgcaga tacttctggg aaccccaggc gtcagtctcc    2940
tcatctgtaa aggagagaga accgatgacg tatcaggcat aatccttgat gagagtttgc    3000
tgcgtgccta ctcagtgcca ggcgctgggg gacacagccg tgttcaggac agccttggtc    3060
ctgttctccg ggagccgaca ttccagggg agagaagttt cctgaagact tccatgctgc    3120
gttccctcct ctgctcctgc tcctggcgcc atcctaggag ccagccatgc acgcaagcgt    3180
catgcctcca gggctctgac tgcccagccc ctcaccgcaa ctccacctca gctgcacaca    3240
cccttggcac atcctgaacc tcattttcat gacggacaca caattttgc tctctcctgt     3300
ccaagcctca tcctctggcc gccacctcct tccagctcac ttcctttagt gcggccagta    3360
ccgcccctgc ctaggcatgt cgacctgcag ggacccttt ctggctcttc gaggcctctg     3420
cccaccatcc cctctttgtt ctccatagtc ccttcccct gttctctctc gtttcatctt     3480
actggtctgg caaagtcccc ggccttgggc gagccagacc tcctcagtgc ctgcacacag    3540
ctgcccacag ccagagaaat ccatttaagc agactgcctg catccttctt aacagtgcaa    3600
ggcaggcact ccctgccaca agagacctg ttccctagta gggcagcttt tctcctcccc     3660
agaacctcct gtctatcccc acccaatgtc tcctcacagg catattgggg aaacaggtca    3720
ggctctccca ccgtatctgc aagtgtactg gcatccatct gtcttcttcc tacccctaca    3780
gtagaaacag tgtctgtccc cagctgtgct ctgatcccgg ctcctttcac ctcagagctt    3840
ggaaaattga gctgtcccca ctctctcctg cgcccattca tcctaccagc agcttttcca    3900
gccacacgca aacatgctct gtaatttcac atttttaaacc ttcccttgac ctcacattcc   3960
```

```
tcttcggcca cctctgtttc tctgttcctc ttcacagcaa aaactgttca aaagagttgt    4020
tgattacttt catttccact ttctcacccc cattctctcc tcaattaact ctccttcatc    4080
cccatgatgc cattatgtgg cttttattag agtcaccaac cttattctcc aaaacaaaag    4140
caacaaggac tttgacttct cagcagcact cagctctggt tcttgaaaca ccccgttac     4200
ttgctattcc tcctacctca taacaatctc cttcccagcc tctactgctg ccttctctga    4260
gttcttccca gggtcctagg ctcagatgta gtgtagctca accctgctac acaaagaatc    4320
tcctgaaagc ctgtaaaaat gtccatgcat gttctgtgag tgatctacca agaaaataaa    4380
aaattttaaa aatcaaatgc ccatgcctgg gcccacacgc agggctctg atttcatcag     4440
tctggtaggt gggttctggg catccacgct cactggattt ccggatgatt gtagtatgca    4500
gcctaggctg gaaccactg gcctcagcaa gccagtcatt ctccaggtgt cacagaccct     4560
ctaggtgcta atgaccccga aggtctgtct tcagtgcaca cctcccctg agctccagat     4620
ttaggaatcc cactgcacac gagacatctg gatgtggaaa agacatctcc agatcccatg    4680
ggtgaaaggg ggttggggga atggagactc gtgttcttcc aggatgtgtg tggacacaga    4740
atgcaaagcc tggagggatg ctagagccat agggaggaag atttcggctc acttattcat    4800
gcaagcactt cctgatgggt aaggtcttag agcaagctga ggccaagagg cgggcagtcg    4860
aggtgctgct gcaggcaccc ccactcccta cagtggcaag cccaagccca gcccttggca    4920
gctcaaatcc caggacacgc tgaaggtcac ccagagagtc aggggcatgg ctagaaccag    4980
aacccaggac tctggggacc cagcatggca tcctttcctt cattacaaat ctgagctgct    5040
ttgtttccta gggatttctg tgatattcca aggggactgt gggaaagaaa gtccttggaa    5100
accaccagga cgctagaggc ctggcctgga gcctcaggag tctcggccac cagagggcgc    5160
tgggtccttg tccaggtcca gttgctacgc aggggctgcc tgtgctggga ggctccccag    5220
gggacacaga ccagagcctt gcaccagccc aaggaatggg agcctggggt cctctctgct    5280
ggaggactgc caggacccccc aggctgccgc ctcttccttt gctcatttgc tgtttcactt    5340
tgtcaatcct tcctttcttc gtgtgttcat tcacatccac tgtgtgctgg ccctggggaa    5400
atgttagata agacacatta gctgtgtgtc ttcattgtcc taacaaagaa cacaccctgg    5460
aaagagcacc gcagagagtc cccattcccc catctccctc cacacatgga atctggagat    5520
gcctttccca catccagatg tctctggtgc tgtgggattc ttaaataaac aaacatttca    5580
tacagaatgt gagatgatgg agatgctatg gggaaaagta aagcagaggg agggcctagt    5640
gtgtgatgcg ggtgaggcat ccagggattg ctgtttcagc tgtgatcagg aaaggccctg    5700
ggaggaggcc acatctgagc agagacctaa ataaagttgg aaacctgttg ctgagatatc    5760
tggagaagtg tttcaagggc cgggcaccgg gcatggtggc tcacgcctgt aatcccagca    5820
ctttgggagg ccaaggcagg tggatcgctg gaggtcagga gtttgagagc agcctgacca    5880
acatggagaa accccatctc tactaaacat ataaaaatta ccgggcatg gtggttcatg     5940
cctgtagtcc cagctactcg ggaggttgag gcaggagaat cacttgaacg tgggaggcag    6000
aggttgcagc aagccgagat cacaccactg cactccagcc tggatgacag agcgagactc    6060
cgtctcaaaa aaaaaaaga aagaaaaaa gaaaaaaaa gaaagtgtt tcaagcaggg         6120
gaactggcaa gtggagaggc cctgaggcag aaatatgctt ggcctgctgg aggaaatgtg    6180
agtgaggagg tcagggtggc tggagtggag ggagcgagtg gtaggagtca gacccagttt    6240
attcatattc tgtaggtctt aaggacttca gtttatttt gagtgcaata tgagcccact      6300
```

```
ggaatgctaa aagctgagag tgacatggtg ctgtgattct ggctttaaaa atatcacttt    6360
ggctgcttcg tgaagactct ggaaggggca agggtgaaag cagggatgcc cgttaggaga    6420
ccgttacagg ggcgcaggca caaaatggca gtggctggga caatggtggc agcagcggtt    6480
agatgtgaac atgttgaagg tggaatttgc agaatctggg ggaggacaga agagaaagga    6540
taacttcatc gtttctgctg aaccagttgg ataaatgttg gtggcacttc ttgaagtgag    6600
gaaggagtta ggaaggtggg aaaggcacaa gtttgaattg ggccatgatg gtctgagata    6660
cctagtacag tggttcccca accttttttgg cagaagggac cgctttcatg aagacaatt    6720 tttccacaga ctgggggtgg ggtggggatg gtttcagggt ggttcgagtg cagtacattt    6780
atcattagac tctttttttt tttttttttt tgagatagag tctcgctctg tcacccacac    6840
tggagtgcag tggagccatc ttggctcact acaacctctg ctgcccaggt tcaagtcatt    6900
ctcctgcctc agcctctcaa gtagctggga ttataggcat atgcgccacc acgcccagct    6960 aattttttgta ttttttagtag agacggggtt tcaccatatt ggccaggatg gtctcgaact    7020
cctgacctca agtgatcctc ccccgcctca acctcccaaa gtgctggggt tacaggcgtg    7080
aaccactgca cccggcccat ttatcattag attctcataa ggaatgagca acctagatcc    7140
ctcgcatgca cagttcacaa tagggttcac gctcctatgg gagtctaatg ctgccgctgc    7200
actcagcttc tctggcttgc cgctgctcac cttctgctgt gcagcccagt tcctaacagg    7260
ccacaaacgg ggagttgggg acccctgatc tagtaaacat ctaggcaggg ttttggataa    7320
tggagttaga gttcctgggg agaggtcagg ctggccatga acatgggat gcctttgcat     7380 ataggtggtg ttgaaagcca caggacagta cggggtctca gggggtgagc ataaagagag    7440
gcgacatcag atggccaagg ccagaggcag aggaggatgg gaaggagggg ccagtggggc    7500 aggggggaagc tgtgaagcca gggaaaaagg gtgtttcgcg gaaaaggatc aacctggacc    7560
agtgctgccc ctaggcaggg caggatgaaa cttaaccacc acggattcca tggccccatg    7620
gcctccaggc cacaggggac cttgagaaga gagatctcag gggacgggtg cggacaagag    7680
cccgcctggc atggcttcaa gagataactg aaggaaagca agtggagacg cgataaacag    7740
acaactccct ggaggaattt tactctcgag aggagaatta aagggtagta gctggagagg    7800
gatgtggggt caagagaagg tctttaacga cgagaactct cacggcggtt tgtgcagaac    7860
agggtgggtg tgatgactgt ggatggagag gggagaactg cagcgactct gtcctaggag    7920
gaggtgatgg gccgggacca ccaagcgagt ggagggtgga cgccccttcc ctcaccccga    7980
cacccgcatg tgctcagtgt ccgtgccgcc ggccctagtg cctgggctga acgcggggcc    8040
gggactctga ggacgcctcc caggcgcgca gtccgtctgg ccaaggtgga gcgggacggc    8100
ngcttccgac ggtgcgcggg tcggctcggg gttgcaggga catccggcgt ccgctcctgc    8160
cctgttttcc tgccttcgca gagcgttgcg caactctagc tttaaacgcc cctgtccccc    8220
tcaacttgtc tcccccagcc cctctgattt acagattctg cagtccccga gggttgcgcc    8280
tacgataccg acactcgcgg cagcctgcga ggcgagtatg atcgtcccat ttttcggagt    8340
agcaaactaa ggttcagaga ctactatgtc ccaggtcggt ctggtttgaa ggtccgcttt    8400
cctctccctc cgccagcggg cggtgcgagg gactgggcga ggcagcgctt ccctaaggag    8460
gcgaccgcca gccccggccc cctcccgact ccgcccgtt gcaggccg ggtcggcgag    8520 gcctctcagc tctaagcccg acgggacttg gtgattgggc aggacggaag agctgggtgg    8580
ggctttccac cagcggagaa agtctagtgg gcgtggtcgc gacgagggcg tggcctggtg    8640
ccccgccccc gtccgcgcgc tcaaagtgga gggtggctgt gggggcgggg tcagaacact    8700
```

```
ggcggccgat cccaacgagg ctccctggag cccgacgcag agcagcgccc tggccgggcc    8760
aagcaggtat cgacgaccgc gcggggcgtc ttgggctgga ccaggcgggc gcccggggcc    8820
tgctgaggac cacaaagggc actggggtc gtggtccagg ctgtgcttcc tcccgctggc     8880
cctggcccct gcctccgccc ccgcccccgc cttcctgccg ctaagccggc tgcggcgggg    8940
ccgattggcg cctgccggct tcctgcgccg gggccagtct aatgcatggg gcccgggcgg    9000
gggactaagg ggaaactgag tcacgtcggt gtgggagcag ttctgtgtgg gaggcaccac    9060
cccccactgg gctcggggaa ggatcccct ccaagctatg cttgagggtc ccagccccca     9120
tctgtctcca caggggccgc accccactcc cgccttcccc ttcttcagca cccagggtc     9180 ccgcctggc tccagcagc ctcgactggt cccggaatgg ctaggaggat ccgctgcagc      9240
cgcctccctc ccctcccctc ccctcccctc ccctcccctc ccctcccctc ccctcccctc    9300
cccctcgcgt cccaagcccc cgtgtgctcc ctccgctggc tctccgcaca gtgtcagctt    9360
acacgcctta tatagtccga gcaggctcca gccgcggcct gctgccggga cctggggcg     9420 ggggagagga gagccggccc ctgactcacc cggaccgccc gaggctccag gctggcttgg    9480
ggggaggccg cgccagtttta gtccctcggc ccaccccctgg ttgcaaagaa cctcaagcct  9540
ggattcaggc acccctcacc gttccagtcc caagggagg ggggctgctc ctgtctttcc     9600
aaagtgaggt ccgccagcca gcagcccagg ccagcctgac aaaatacctg cctcctatgg    9660
cttgggcgtg ctcaggggct gcccgtgcct gcctggcccc tgtccaaggc tggtatcctg    9720
agctggcccg gcctgcctgc ctgccgccc accatgctgg ccactcacct tctcttctct     9780
cctctcagga gccggcatca tggattcctt caaagtagtg ctggaggggc cagcaccttg    9840
gggcttccgg ctgcaagggg gcaaggactt caatgtgccc ctctccattt cccgggtgag    9900
cctaggtttg ggaggggggc tccccagcg gtctttcggt gcttaggtct ccagagggtg     9960
atggggggag tcctaacagg agctggtcag gggccagcag gccaggagat gtctaggtcc   10020
ggagatgtag tggtacctgc ctgccacaag gactcccaat gaggtggata ctgggaggga   10080
gcacccaggc ttctccagcc ctgcactgta cccgatgctg ttctcccaag ctcctgtggc   10140
cacctctgag ggctggaggg aggctcattg tgcaggatgg gagcctaaca tttcaggagg   10200
tatctaaact tgaggtggca atgcttggag ccaggcccca gcaggacac tgtgactata    10260 ggatttcact tcagcctcac tgccgcccag ggaatagcaa tcctcatccc gttttttccag  10320 atgagagaag aactcatgga gaggtggcgg ggctcgctca tcgagtccat ggtgaagcag   10380
ggattggaat tgaggcacag catggcgtac atttttttgtg ggtagaaggg gtctctcccc   10440
agcctatgta aggacccaca tccactgttc ccattcagga tgtggtggcc tttgacccca    10500
agcagaagtg taggacaggg ctccattcta ggggcttaac ttcagcttcc aagagcctgc   10560
cctggtgtgg gtggagctgg aggctggctc ctccctgtag caggggggatt gccttataag   10620 cccaagaatg cagccccacg ctgggatggc caacagtggc tgcggtctgc agagctgaaa   10680
agggctggcc taggcctggc ccctgaacc ccactggtgg gcctctcagc tggtcaccag     10740
gctgcagctc cagctgtatg gtccagttgt gagacacaac aaattgcctg cccagagtgg   10800
gtgaggccag cctgtcggct ggcatctctg actggcctgg gggtcaggag ggggtgggga   10860
cttcctgccc ctatatccgc ctgccccgag agacccaccc aggcgccggg tggcaggca    10920 gctgttgtca ggaagcccaa ggcaagccca gctggagggg gcccagaggg tcgtggcctg   10980 aggagggct caagctggag tctgtctgta ggagctgggc gtgggggtta gggtgggcag    11040
```

```
gccagcagtg ctcttctcag gggtcctttg atggcattct cctgaacct gccccgccag    11100
cagggtagtg aggcagtggt tgccctatga cacacgtccc actacatagc cctcacacag    11160
ccctgaaacc tacctgacgt cctgctccct gggaaagtgc tggcccagtg tgtctgggga    11220
gcctgaacct cagtttcttc cctgatggag atgactttca gatatggcct gttggggca     11280
ctccgggctc cagctccctg gtcagcatcc ctggcatgtg ggcggggcca ctagctgatc    11340
ccagccctgg agttggacct gggcccacat gggtgggtga ggtgggcttt tctgagttag    11400
gccagccccc tcccctccc ctgacccag aatggaggga ggtgggaggg gcaagggctg      11460
gctgtgggcc caggcctggg agatgaggta acgtctggga ctggggggct gggctgctca    11520
ggctgactca cccccacctc atgcagggtc cagcccctg gcttttcc tccttggttc       11580
ctctggcctt accctgcccc tggcttgagc ccctccctgc ctctctccag ccacccgccc    11640
agcgctgtct tctgctctcc tgctgccctc cccacgctct gaacacccct catcctctgt    11700
gcttcctgcc ctcctcactc tgggaaggga agccgtcccc gccccccacc ccctctccag    11760
gagccagcta gctgcacccc aagaccccca cctcgggctc agcccacagc tcccaggagc    11820
cagccctgtg ggcagggagt ggctgggcca ggtttcccctt ctactgactc accatgacct   11880
tgagtaagtc acttcccctc tggggtgtca cttccccata cacagtataa ggggttgatt    11940
tagttggatt gaactaaagg tgagggagtg gctcagggtg tctccaggtg ggctgacccc    12000
tcagttgggc cccatgctc agcagaggtg gcccacagtg gtggagcctt agggtcagag     12060
acacttcctg gctctgcctc ttactagctg ggtgacttga ggcaagttgt ttaacctctc    12120
tgtgtacatt tgcaagtgca aaatgggtaa aatcccagat tactccacaa ggttgttgga    12180
agattcagtg tcaatatgta gcatagttgg tgctcaataa actgaagcaa gtcttcttat    12240
ttagcgagtg aggaaggggc cgccgagctc tcttagcctt ctgacctcct acgcaagcaa    12300
gaggtcatgt tgagcccagc tcgcctttct ttcccagtg ctgtcaagct ctgtgcctgg     12360
ctgccctgcc ctctgacatc tctctgaaac ctcttgcctc ccctctccct gcctcagctc    12420
agtctgtgca ctgacccacc tgaggagcct cctggggcca ctgcagcct ggaccccccc     12480
agatccccc cacccagtga aattgtcttc cagcactgcc tcacaaaagc ctacttgatg     12540
cagtgccagg cctcttgcca gatggctggg tggtccctta ggcttggacc cagtcaagct    12600
gccctgcctg tgttgctggg gctgggctag aggcctggaa ggggtttatc agggtcaccc    12660
tctcagggcc tgggagatac ccaatcccag acattaaaac tgccagtagc ccctctacct    12720
tcaaagccaa gtcctggtcc cttcccctgg cattcaaagc catcgtaagt gaactctcac    12780
ccgctaggca gcacacgcca ttctcccttta ccgaggccca ccgcttcctc aaagtcattc    12840
ctgatggtct cagctcatgc tggtggcagc catttctccc agcctactgt ctctactcat    12900
tgccacagga accagggact cccagctcaa gagcctgaag gattgggtc agggggaaatt    12960
ggcagtcgag ggcttgggag tgacagccat gtatggccta cgaagtccca gctgtcaact    13020
taggtcccat tcaggcagtg ttcacaggga accgggagat aacagggcct gttcctggct    13080
ctcaaagggt cccagcagac ccctatagat ggccccgac agggtgctgg ggggtgagag     13140
gtccataaga gccccggtg gtttcgggga ggaagctgcc ccctgcatgg gccagagggc     13200
atatctggta ggtggagtgg cctgggcagg aggccagcag gagcctcaaa aggcaatggt    13260
cctcctgaaa cacttgggct ttagcctgag cgtggctgtt tgtggacatc atagcaattt    13320
ctggactgtg ggggagggtg gtggcggtga atagataagc atcgtgactg gggaagctca    13380
ggtgagcacc acctgaggga gagggtctgg cagtgaataa ataagcagtg tgactgggaa    13440
```

```
attgtgaagc tcaggtgagc gccaccacct cctgggttgc tttagtgtcc agcagctgcc   13500
tagaactatg ttgaatgaag agctctctgg gttctggaag tgggacagct ttgggtgggg   13560
cagtgttacc accgtcagcc tggcttgggt ctgcagggtc cagggcctcg gtcactttgc   13620
ttctctctcc acagctcact cctgggggca aagcggcgca ggccggagtg gccgtgggtg   13680
actgggtgct gagcatcgat ggcgagaatg cgggtagcct cacacacatc gaagctcaga   13740
acaagatccg ggcctgcggg gagcgcctca gcctgggcct cagcaggtat gcgggtggac   13800
atggatgggt gcgcccgcgc tggcagtggg gatccctgcg gccggcccg ctgtcacgct   13860 ttccttctcc tccagggccc agccggttca gagcaaaccg cagaaggtac gaggctggcc   13920
gggacatccg ggcggtgggc ggtgtgggct tggacggcca ggcctgctcg ccctcctggc   13980
acattctcgg taccccaatc cctggccggg agtggagggc agaaaccgga gctaaggcgg   14040
gtctagggcc ctggagttga gccagggggct gctgcacggt cctggcacca cgcatgtccg   14100
cctgtctgtc cgcctgtctg tccgcctgct gcctcccgcc gccggcgctg cgtgctcgcc   14160
cgcactcggt cagccctcgg tcctgcgtgg actgagatcg ccactcccaa atgggcccct   14220
tgaaacctga gtcgtcctct ccccgtagcc tccaaataga tgtaggggt ggggtgggg    14280 tgggggggctg gagctgccgc tgtcctctgc tgcaggcgcc ccacttccac ccaggccccc   14340
accttaccct gcccgcccgc cctgcccggc tgtgtctctg cccaggcctc cgcccccgcc   14400
gcggaccctc cgcggtacac ctttgcaccc agcgtctccc tcaacaagac ggcccggcct   14460
ttgggcgccc ccgccgctg acagcgcccc gcagcagaat gggtacgtcg gcccctgccc   14520
gcccgcgccc acgccatcag gcccactgtg gccccacgcc cgctgccgc tgctgctcag    14580 tctgtgctgc gccccagccc ggcggaaccg tgcggcacgc ccctggcgg ccggggtggg    14640 gctgcaggca cagggcccct cccgaggctg tggcgccttg cagggcaccg cctggggagg   14700
ggtctctgaa tgacgccgcg ccccctgctg gcggctgggg gttgggttgt ggtgtcgggc   14760
cagctgagcc ccagacactc agtgccgcct tgtccccggc tgttctgacc cctccccgtc   14820
tttcttcctc tcctgtgtct gtcccttttgt cccttatct gtctgtctgt cttatttcct   14880
tcacaggtgc agaccctga caagtcagtg agccccctc tgcctgtgcc tttcttcttc    14940
cttttggcac tctgggtggc ggccctccc caccctggct gccctcctct ccacttcgcg   15000
ctcctgtcct ctcacctacc cgcccagcag ggctcctggc ctcaccctta cccactccct   15060
cccatcactg taacccaaac ccacatgcac caaatcctgg gaggggctgc ccccaccgcc   15120
cacccccagt gtgggggttct gagccacacc ctccccacag acagccgctc cgaccgctgg   15180
tcccagatgc cagcaagcag cggctgatgg agaacacaga ggactggcgg ccgcggccgg   15240
ggacaggcca gtcgcgttcc ttccgcatcc ttgcccacct cacaggcacc gagttcagta   15300
agtgccagcc cagggcaggg ggtactttcc tcgcccccag cccaggcgtg atccctgacc   15360
ctgtgtcttt tttggtcaat gcctgcctct gctctctcag tgcaagaccc ggatgaggag   15420
cacctgaaga aatcaaggta cagggacggg caccagcccc tctcccacct cctgcctctt   15480
ccattccagc tactgccctg tgtctactcc tgaggctccc agctggggct ctcaattctc   15540
ccttccttcc ttccttcctt ccttccttcc ttccttcctt ccttcctcc ttccttcctt   15600 ccctccctcc ttccttcctt ctttcatttc ttccctccct ccttccttcc ctcctcctc    15660 cctgcctccc ttccatctct ccttcctcc acttcttcct ccctctctct ctgcccctca    15720
gggaaaagta tgtcctggag ctgcagagcc cacgctacac ccgcctccgg gactggcacc   15780
```

```
accagcgctc tgcccacgtg ctcaacgtgc agtcgtagcc cggccctctc cagccggctg    15840
ccctctctgc ctccctcttt ctgttcctcc tgcccagggc acccccttag tgcctccagc    15900
ttctgcctac ctcacccccc ctttcgtgcc cctggcctga gctcctgct ggcctggccc     15960
tggccgccca cctgggttca tctgacactg ccttccctct ttgccctgtg gtactgctgt    16020
ctgccaggtc tgtgctgcct tgggcatgga ataaacattc tcagccctgc ttgctctgcc    16080
tgtcttctat ctttgtggac ctggtttgca tttggggtgt gggggtgttt cgtggttcgg    16140
actgtttggg ccctgccgtc cttgttttca gtgggagggg gtacctggca aaggggccct    16200
gccctgccat cacagatggc ttcctggcat gaggggagcc ccaggagctg cctcagaagc    16260
gggagccctg cctcgtctcc cagctagaga ccgcacacca gctaactgga cattgctagg    16320
agaagctgcc cttcccatcc ctaccccagt gggacctgga atccaactcg gcagtttcca    16380
cgccccagt catctcccgt ggggccagca ggacccaggt tgggggtgg ggccatgtca      16440
ggaagctcag ccatgcaggg ccttgaatgg cagatcttgc agccaggtgc ccaggacaga    16500
agccccagcc ccagcctcat ctacacccca ggagccctgg cctggtgaga gggagtgggc    16560
tcgggcctgg gcaagggtgg gcagcctcca ggggcatggg ggtggtgggc ttctctcagc    16620
tgcctggggc tccacccccg tcctttgggg tccctgggca cccctttaga gtcactttcc    16680
ccggcaggcc ctaccgcccc cagccctacc agccgcccgc cctgggctgt ggaccctgcg    16740
tttgccgagc gctatgcccc ggacaaaacg agcacagtgc tgacccggca cagccagccg    16800
gccacgccca cgccgctgca gagccgcacc tccattgtgc aggcagctgc cggaggggtg    16860
ccaggagggg gcagcaacaa cggcaagact cccgtgtgtc accagtgcca caaggtcatc    16920
cggtgggtgg cctgttcctg tccgaccctg gctttcccat cctgcagccc agccccacct    16980
gtctgcccac ctgtcttgcc tcagctgcga ctgggggaa taaggattca gttctcagct    17040
ggagtaggag tagggacctg gctgggtcc tcccattctt aatcccacgc tacctacccc     17100
agcccaccca caacaactgc tagcagcatc tgccgtggcg aaatagccga agggccaacc    17160
ataggctgaa gctgcacccc tacctttgct gctctctggg caaagagggg cctgcccct    17220
cccagcgcgt ctgccctcc ctcctgctct ctgtctccct ctgctctcag agcatacagg    17280
cctggagcca ctccctctgt gcactgcccc gtgggccaa gcagcatcaa acacccccca     17340
gcatcagcgt gccggattct agagccttcc taattcgcag gcctggcctg ctctcatctc    17400
tgtcagctct ttttttttt ttttgaaac agagtctcac tgtgttgccc acgttggcgt      17460
gcagtggcgc gatctcggct cactgcaacc tctgcctcct gggttcaaga gattctcctg    17520
cctcagcctc ctgagtagct gggattacag gcacccgcca ccatgcctgg ctaattttgt    17580
atttttagta gagacggggt tttaccatgt tggccaggct ggtctcaaac tcctcacctc    17640
aggtgatctc aggcctgcct tggcctccca aagtgctggg actacaggtg tgagccactg    17700
tgcccagccg actctatcag ctcttgccag gtagaacagg caggccagca ggacagggca    17760
gctccagggt ttgcccaggg gcggctcagc ttttatgagg ctccagtcgt cagcccttcc    17820
tcccggggtc ctccctgctc taaagctgcc tctcctgtca ccagcagttc agtgtggcgg    17880
actggctctg taagcttcat ggctgccacg gtcacttccc aagcctgtct tctatcctat    17940
gtggaaaatg gggagaatga actgtccctc ccaaggcctc ctggtgggtg gtcagtcaac    18000
ctgaaggggg ccaagacccc cacctctctg cgtgtgctcc ctctgaccgc tctcgcctcc    18060
ctgcagggc cgctacctgg tggcgctggg ccacgcgtac cacccggagg agtttgtgtg     18120
tagccagtgt gggaaggtcc tggaagaggg tggcttcttt gaggagaagg gcgccatctt    18180
```

```
ctgcccacca tgctatgacg tgcgctatgc acccagctgt gccaagtgca agaagaagat    18240
tacaggcgtg agtagggctg gctggcgggg aggtggtccc aagcctgtca gtgggaacga    18300
gggctgctgg gaaacccaca gtccaggtct ctccccgagt gagcctccgg gtccttacca    18360
gcgtaataaa tgggctgctg tactggcctc accctgcatt agtcaggatg ctcttaacaa    18420
atgaccatgt tcctgctcag aaaccgccca aggctgcaaa gagcaggagg accaagccag    18480
gagaagccct gggccctcct gactcccact ttgggctctc cctgccctgg tgaaatgaca    18540
gaacggccaa cttgacacgc tgaagctgct ctgtctcatg cgtcctcctc atttctggat    18600
ccagagccag ggctgccagg agtagccaga gagctctgtg tggtgatgtt catattagtg    18660
aggtttacct tgaccacgag cagtgggaaa ctcaaaataa tggtggctta tttctcatct    18720
aaaaacatcc cggggtgggt ggtctgggac tgatctggtg gacccaggct ccgccttgtt    18780
gcttgactgt tggcagcacc tgcttactta ccactcatgg tgcaagatga cacttcagcc    18840
tccgccaaaa tgctcacctt ccagccagca ggaagtcgga aggagaagaa aggggacaga    18900
gccccatggc gtccatcctt agaggatgct gccacctgaa cctctgcttt catcctgttg    18960
gtcagaaccc agtcacatga ccacacccag tggcaacgga ggctgggaaa tatagtcttt    19020
attttgggca cccatgtgtc cagcaaaact ggggttcca tcagtcggca agaacgggag     19080
agtggccgat gcagtggctg atgcttgtat cccagcactt tgggaggtcg aggtgggcag    19140
atcacctgag gtcaggagtt caagaccagc ctggccaata tggtgaaacc ctgtctctac    19200
taaaaataaa aaaattagct gggtgtgctg gcgcacctgt agtcccagct acttgggagg    19260
ctgaggcagg agaatcgctt gatcttgaga ggtggaggtt gcagtgagcc aagattgtgc    19320
cactgccttc cagcctggga gacagcaaaa aaaaaaaaaa aaaaaaaaaa aaaagggcc    19380 aggcacggtg gctcacacct gtaatcccag cactttggga ggccgagatg gcggatcac    19440 gaggtcagga gattgagacc atcctggcta acacggtgaa accccatctc tactaaaaat    19500
acaaaaaaat tggccgggca tggtggagta gtcccagcta ctcgggaggc tgaggcagga    19560
gaatggcgtg aacctgggag gcagagcttg cagtgagccg agatcgcgcc actgcactcc    19620
agcctgggca acagagcgag actcttgtct caaaagaaa aaagaaaga gaaatctgcc      19680 tcccagcctt gggctcctgc cctaccagcc cacacccctg gtagagcctc ctctcccacc    19740
agctcaaagc ccaagttcct tcactgtgac cttgtctgct cctctaaaac aggcaacacc    19800
agacagtgag aagagccagc cagacatggg cagaaaacct atttctgtga tctactggct    19860
gtgtgagcag gggctagttg ctctctctgg gcctcactga agagaagggt ggcactatgc    19920
tagggccggc acggttgcaa ggtagatgta agatggggta caggtgttgt ggagggcaga    19980
aatgcaccat ccgaaggcta catgtccccc acacttatgt cttgcttggc ccacactgtt    20040
tcattttaaa atcagtagca aacaatttaa aaaatcagaa gatttgcctg catgatgcag    20100
tggctcatgc ctgtaatccc agcactttgg gaggccaagg tgggaggatt gcttgagccc    20160
aggagttcaa gaccagcatg ggcaccatag caagacccct gtttctacaa aaaaaaaaa     20220 attagaaaat tagccaagtg tggtggcatg cacctgtggt cccagctact tgggaggcag    20280
agggaaagtg agatcctctg cttttttattt ctttatgtat aatgatatggg tcttgctctg   20340 ttgcccaggc tggagtgcag tggcatgatc actgctcact gcagccttga tctcctgggc    20400
tcagaggatc ctcccacctc agcctcccaa atagctagga ctagaggtgc ccaccagcat    20460
gctcagcaga ttttaaatc ttttgtaga gatgaggttt tgctatgttg cccaggctgg     20520
```

```
tctcgaactc ctggcctcga gcgatcctcc caccttggcc tcccaaagca ctgggattac   20580
agacgtgagc cactgcgccc agcagatttc tctttaacac ctagatttca gcctgagcca   20640
ggcaggcatt cctgaatgaa ccagtagtac tgctcccaga agaagaggtc ctcctccgtg   20700
tgacacagtc cccacttggc ccttgcaggg attggatctg ggatccctgg atttaaactc   20760
agggccatcc tcataacagc ctcacaaggc tgggattagc ttcccagttc acaagggaag   20820
aaaccaagac ttgagaaggt caaggtctgg ccagacccac acatcttgga ccctcatacc   20880
gcctcgaggc cccatgctgc cctctgcctg ctccagatgt gaatactgct ggccctggct   20940
ggccccggct ggccccgagg gtcctaggga tgaacagccc agcccaggga gagctcagcc   21000
ccttgtgcct ctgccccttc ccacctcctg cggaggccag tcgactcacc cacaaagggc   21060
caggcactgt ggggatagat cagctaacaa aacagttgat gcttcctgcc cttctgggcc   21120
ttacattttg gctggaagaa gaggggagag gcagactgta agcaataagc gcaataagta   21180
ggttgcctgg aagtaatgtt agatcacgtt acggaaaaca ggaaagagca gagcgacaag   21240
tgctggggtg cgtggtgcag ggaaggcagc tggctgctgc tggtgtggtc agagtgggcc   21300
ctcatggaga agactgcatt cgagcagaaa cttgaagggg gtgaggggtg agcctagaga   21360
tatctggggc agagcagtcc aggcagaggg gacagccggt gtcaagccca ggacaggagt   21420
gtgcctggtg tgccagtttc aggcaagagg ccagtgtgca gaggcaaggt gagaacgcaa   21480
gggagagcag tggcggagac gggtgggaac gaggtcagac ctgctggcct ccagcctctg   21540
catgggcttt ggctcttgct gggagcaatg ggaagcagta cacagtttca tgcaggggga   21600
gaaggcctgt cttgggttgc aggggcacgc tgtggcagct gggatcagag agaggagctt   21660
gtaggccagt tgttatgtgg tcccacgggc cagatggcca tggcttacct cacttcaggg   21720
aggctgtgag aagcactcag aatctggatg tgccttgggg gtgggcccca ctggatttcc   21780
tggtggacct ggtgtggggt gtgagaggag ggtgtgtttg gctgcagcag acaggagaat   21840
ggagttgcca tccgcgtgat ggggatggct gtgggaggag aggtttgggg tgagggaatc   21900
aggaactgag tgctggacat ggcaagtctg aaggcgcagt ggtcgtccac tcagagacct   21960
tggagttgga gatggaggtg tgggagtcct gaacagttag atgtagtgtt taccgcgaga   22020
aggaacaggg cttgcggcca gccctcctgt gttcccgtga cccagggcag ggcaggaggg   22080
gcctgagcct gccgagtgac tgggacctcc ttccaggaga tcatgcacgc cctgaagatg   22140
acctggcacg tgcactgctt tacctgtgct gcctgcaaga cgcccatccg aacagggcc    22200 ttctacatgg aggagggcgt gccctattgc gagcgaggta cccactggcc agtgagggtg   22260 aggaggatg gtgcatgggg caggcatgaa tccaggtcct cttcctctct gcccccattc    22320
tcagactatg agaagatgtt tggcacgaaa tgccatggct gtgacttcaa gatcgacgct   22380
ggggaccgct tcctggaggc cctgggcttc agctggcatg acacctgctt cgtctgtgcg   22440
gtgagagccc cgcccctcga actgagcccc aagcccaccg gccctctgtt cattccccag   22500
gagatgcagg agaagttggg aaggggcctc tcctgctgcc cccaacccca tgtgactggg   22560
cctttgctgt cctagatat gtcagatcaa cctggaagga aagaccttct actccaagaa    22620
ggacaggcct ctctgcaaga gccatgcctt ctctcatgtg tgagccccct ctgcccacag   22680
ctgccgcggt ggccctagc ctgagggcc tggagtcgtg gccctgcatt tctgggtagg     22740
gctggcaatg gttgccttaa ccctggctcc tggcccgagc ctggggctcc ctgggccctg   22800 ccccaccca cttatcctcc caccccactc cctccaccac cacagcacac cgatgctggc    22860
cacaccagcc cccttcacc tccagtgcca caataaacct gtacccagct gtgtcttgtg    22920
```

-continued

```
tgcccttccc ctgtgcatcc ggaggggcag aatttgaggc acgtggcagg gtggagagta    22980
agatggtttt cttgggctgg ccatctgggt ggtcctcgtg atgcagacat ggcgggctca    23040
tggttagtgg aggaggtaca ggcgagaccc catgtgccag gcccggtgcc cacagacatg    23100
aggggagcca ctggtctggc ctggcttgga ggttagagaa gggtagttag gaagggtagt    23160
tagcatggtg gctcatgcct gtgatcccag cactttggaa ggccaaggtg ggcagatcgc    23220
ttgaggtcag gagttcgaga cctcatggcc aacacggtga aacagcgtct ctagtaaaaa    23280
tacaaaaatt agccgagtgt ggtggggcat gcctgtaatc ccagccactc aggaggctga    23340
ggcgggaaaa tcacttgaac ctgggaagtg gaggttgcag tgagctgaga tcacaccact    23400
gcgcgcgagc ctgggtggca gatggcgagc gagaccctg cttcaaaaaa aaaaaaaaaa    23460 aaaaaaaaa gaagggtagt tgtagttggg ggtggatctg cagagatatg gtgtggaaaa    23520
cagcaatggc cacagcaaag tcctggaggg gccagctgcc gtccaaacag aagaaggcag    23580
ggctggagag ggtagccctt aggtcctggg aagccacgag tgccaggcag tagagctggg    23640
gctgtctctt gaggttaggg cagggcaagg cacagcagag tttgaaatag gtttgtgttg    23700
tattgcagaa aagaggcccc agaacactga gggagtgcag gagggaggct gggaggagga    23760
gttgcagcag ggcctagggg cggggccag gcaaggagg ggcagagagt aatatgcag     23820 agatgggacc cagtggcagg tccgggggat gagggatgga gagaaggaca ggagcgttgc    23880
caggcatctg gcctatacca gacatgctca cgctgtctcc cgcgaacctc ctagcaacct    23940
tgcgccgttg tctgcaatca cttatttcat tttttctttt ttaactttaa ttttttttgt    24000
ttttaagaga caggatctcc ctaggttgcc cgggctggtt tcaaactcct gggctcaagc    24060
aattcttcct ccttagcccc aaagtgctgg cattacaggt gtgagccacc atgcctggcc    24120
cacttatttt ctagatgagg cacagaaaga ttgggagact tgaccaaggt cacgctgtca    24180
ttgagccatg agccagacta gaatccaggc ctgaagctgg gtgcgctgtc ccaggactgg    24240
ctggcactga gtaccatttg ccagcgagca tctctctggg aagctgactt ctgcccggta    24300
cctggaggac tgtagacctt ggtggtggcg ccgtcactct ggggcttcct gcctcccact    24360
gatgcccgca ccaccctaga gggactgtca tctctcctgt cccaagcctg gactgaaag    24420 actgaagaga agccttaagt aggccaggac agctcagtgt gccatggctg cccgtccttc    24480
agtggtccct ggcatgagga cctgcaacac atctgttagt cttctcaaca ggcccttggc    24540 ccggtccct ttaagagacg agaagggctg ggcacggtga ctcacacctc taatcccagc    24600
actttggaag gctgaggctg gagaagggct ccagcttagg agttcaggac cagcctgggc    24660
aacatggtga gaccctgttt tgttttgttt tttgttttt tgagatggag tcttgctctg    24720
tcgcccaggc tggagtgcag                                              24740
```

<210> SEQ ID NO 42
<211> LENGTH: 25
<212> TYPE: DNA
<213> ORGANISM: Rattus norvegicus

<400> SEQUENCE: 42

```
gcactacctt gaaggaatcc atggt                                           25
```

<210> SEQ ID NO 43
<211> LENGTH: 26
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 43

Ala Asp Pro Pro Arg Tyr Thr Phe Ala Pro Ser Val Ser Leu Asn Lys
 1               5                  10                  15

Thr Ala Arg Pro Phe Gly Ala Pro Pro Pro
            20                  25

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Asp Pro Asp Glu Glu
 1               5

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aggatggctt ccaccagtgc                                              20

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgcgtaaaag acctcaccct cc                                           22

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cacaagtcag tgggagagc                                               19

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcttccgctg tttgtgtttg                                              20

<210> SEQ ID NO 49

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
accacagtcc atgccatcac                                                20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tccaccaccc tgttgctgta                                                20

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aatacgactc actatagggc tcga                                           24

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggaagcccca aggtgct                                                   17

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agccggcatc atggattcct tcaa                                           24

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Ala Pro Ser Cys Ala Lys
1               5

<210> SEQ ID NO 55
```

-continued

<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Leu Tyr Asp Asp Asp Asp Lys
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr Ala Pro Ser Cys Ala Lys Cys Lys
1               5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Thr Gly Glu Ile Met His Ala Leu Lys
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Phe Asn Val Pro Leu Ser Ile Ser Arg
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Thr Phe Ala Pro Ser Val Ser Leu Asn Lys
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Val Leu Glu Glu Gly Gly Phe Phe Glu Glu Lys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Val Leu Glu Gly Pro Ala Pro Trp Gly Phe Arg
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

His Ser Gln Pro Ala Thr Pro Thr Pro Leu Gln Ser Arg
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Phe Tyr Ser Lys Lys Asp Arg Pro Leu Cys Lys
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Arg Pro Leu Cys Lys Ser His Ala Phe Ser His Val
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ile Arg Ala Cys Gly Glu Arg Leu Ser Leu Gly Leu Ser Arg
1               5                   10

<210> SEQ ID NO 66
<211> LENGTH: 15
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 66

Leu Gln Gly Gly Lys Asp Phe Asn Val Pro Leu Ser Ile Ser Arg
1               5                   10                  15

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Phe Tyr Met Glu Glu Gly Val Pro Tyr Cys Glu Arg
1               5                   10

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Ser Ile Val Gln Ala Ala Gly Gly Val Pro Gly Gly Gly Ser
1               5                   10                  15

Asn Asn Gly Lys
            20

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Leu Ala His Leu Thr Gly Thr Glu Phe Met Gln Asp Pro Asp Glu
1               5                   10                  15

Glu His Leu Lys
            20

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Pro Ile Arg Asn Arg Ala Phe Tyr Met Glu Glu Gly Val Pro Tyr
1               5                   10                  15

Cys Glu Arg

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic

```
            peptide

<400> SEQUENCE: 71

Gln Arg Leu Met Glu Asn Thr Glu Asp Asp Trp Arg Pro Arg Pro Gly
1               5                   10                  15

Thr Gly Gln Ser Arg
            20

<210> SEQ ID NO 72
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Leu Ala His Leu Thr Gly Thr Glu Phe Met Gln Asp Pro Asp Glu
1               5                   10                  15

Glu His Leu Lys Lys
            20

<210> SEQ ID NO 73
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Ala Gln Ala Gly Val Ala Val Gly Asp Trp Val Leu Ser Ile Asp
1               5                   10                  15

Gly Glu Asn Ala Gly Ser Leu Thr His Ile Glu Ala Gln Asn Lys
            20                  25                  30

<210> SEQ ID NO 74
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Glu Ala Pro Ala Pro Ala Ser Ser Thr Pro Gln Glu Pro Trp Pro
1               5                   10                  15

Gly Pro Thr Ala Pro Ser Pro Thr Ser Arg Pro Pro Trp Ala Val Asp
            20                  25                  30

Pro Ala

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 75
ccatggattc cttcaaagta gtgc                                              24

<210> SEQ ID NO 76
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 76
cagggcgggc ggctggtag                                                 19

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 77
ccatggcagg agtgtttgac agaagagt                                       28

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 78
taataaagcg tcccggaggc c                                              21

<210> SEQ ID NO 79
<211> LENGTH: 58
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 79
catggcgtca aacagcctct tcagcgcagt gacaccgtgt cagcaaagct tcttttgg      58

<210> SEQ ID NO 80
<211> LENGTH: 58
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 80
gatcccaaaa gaagctttgc tgacacggtg tcactgcgct gaagaggctg tttgacgc      58

<210> SEQ ID NO 81
<211> LENGTH: 71
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 81
catggcgtcc tctctgcttg aggaagaagc tcactatggc tccagtcccc tggccatgct   60
gactgcagcc g                                                         71

<210> SEQ ID NO 82
```

```
<211> LENGTH: 71
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 82
gatccggctg cagtcagcat ggccagggga ctggagccat agtgagcttc ttcctcaagc    60
agagaggacg c                                                         71

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 83
aaggatggct tccaccagtg c                                              21

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: CDS
<222> LOCATION: (1)..(33)

<400> SEQUENCE: 84 tac ggc cgc aag aaa cgc cgc cag cgc cgc cgc                          33
Tyr Gly Arg Lys Lys Arg Arg Gln Arg Arg Arg
 1               5                  10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide PTD Domain of HIV TAT

<400> SEQUENCE: 85

Tyr Gly Arg Lys Lys Arg Arg Gln Arg Arg Arg
 1               5                  10

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      6-His tag

<400> SEQUENCE: 86

His His His His His His
 1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
```

Peptied PTD Domain of HIV TAT

<400> SEQUENCE: 87

Arg Lys Lys Arg Arg Gln Arg Arg
1               5